United States Patent [19]

Berger et al.

[11] Patent Number: 4,508,717

[45] Date of Patent: Apr. 2, 1985

[54] CEPHALOSPORIN DERIVATIVES, THEIR PREPARATION AND COMPOSITIONS CONTAINING THEM

[75] Inventors: Christian Berger, Ecully; Daniel Farge, Thiais; Claude Moutonnier, Le Plessis Robinson; Jean-Francois Peyronel, Palaiseau; Bernard Plau, Creteil, all of France

[73] Assignee: Rhone-Poulenc Sante, Courbevoie, France

[21] Appl. No.: 522,359

[22] Filed: Aug. 11, 1983

[30] Foreign Application Priority Data

Aug. 13, 1982 [FR] France .................. 82 14092

[51] Int. Cl.³ .................. A61K 31/545; C07D 501/36
[52] U.S. Cl. .................. 514/203; 544/25; 544/24
[58] Field of Search .................. 544/25; 424/246

[56] References Cited

U.S. PATENT DOCUMENTS 4,258,040 3/1981 Christensen et al. .................. 544/25
4,470,983 9/1984 Blumbach et al. .................. 544/21

FOREIGN PATENT DOCUMENTS 2331050 2/1978 France .
2331051 2/1978 France .
2356388 3/1974 Netherlands .

OTHER PUBLICATIONS

Chem. Abst. vol. 81, 1974, Cristensen, 49691n.

Primary Examiner—Donald G. Daus
Assistant Examiner—Cecilia Shen
Attorney, Agent, or Firm—Stevens, Davis, Miller & Mosher

[57] ABSTRACT

Cephalosporin derivatives of the formula:

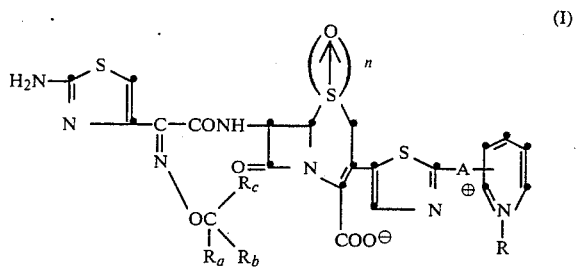

in which A is a single bond or a radical $-CH_2-$, $-NH-$ or $-NHCO-$, attached to the 3-position or 4-position of the pyridinio radical, R is a methyl, carboxymethyl, carbamoylmethyl, benzyl or allyl radical, $R_a$, $R_b$ and $R_c$ are hydrogen atoms, or alternatively $R_a$ is carboxyl and $R_b$ and $R_c$, which are identical or different, are hydrogen atoms or alkyl radicals, or together form an alkylene radical, and n equals 0 or 1, in their syn form, and also their addition salts with acids, metal salts and addition salts with nitrogen-containing bases are antibacterial agents having a broad spectrum of activity.

17 Claims, No Drawings

CEPHALOSPORIN DERIVATIVES, THEIR PREPARATION AND COMPOSITIONS CONTAINING THEM

The present invention relates to new cephalosporin derivatives, to processes for their preparation and to pharmaceutical compositions containing them.

French application No. 2,206,085 describes numerous heterocyclylcephalosporins, in particular 3-thiazolyl-cephalosporins.

The publication by T. Sugawara et al., Chem. Pharm. Bull. 28 (7), 2116 (1980), refers to thiadiazolylcephalosporins whose main advantage is a good activity against Gram-negative germs.

French application Nos. 2,381,050 and 2,381,051 describe 3-thiadiazolylcephalosporins which are active against Gram-positive and Gram-negative germs.

The present invention provides new thiazolylcephalosporin derivatives of the formula:

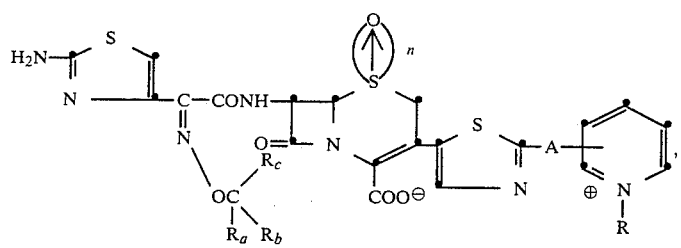

in which the symbol A represents a single bond or a divalent radical chosen from —CH$_2$—, —NH— or —NHCO—, attached to the 3-position or 4-position of the pyridinio radical, the symbol R represents a methyl, a carboxymethyl, carbamoylmethyl, benzyl or allyl radical, and either the symbols $R_a$, $R_b$ and $R_c$ each represent a hydrogen atom, or the symbol $R_a$ represents a carboxyl radical and the symbols $R_b$ and $R_c$, which are identical or different, represent hydrogen atoms or alkyl radicals containing 1 to 4 carbon atoms, or together form an alkylene radical containing 2 to 5 carbon atoms, and n is equal to 0 or 1, and addition salts thereof with acids, and, if appropriate, metal salts thereof and addition salts thereof with nitrogen-containing bases. It is to be understood that alkyl radicals referred to in this specification are linear or branched and, unless otherwise specified, contain 1 to 4 carbon atoms.

It is to be understood that the compounds of the general formula (I) exist in the form of internal salts (betaines; one of the carboxyl groups present in the molecule being in the form of a carboxylato radical) or in the form of acid solvates of these betaines, and that all these forms fall within the scope of the present invention.

It is also to be understood that, in the general formula (I) and in the general formulae used below, the group —O—C—$R_aR_bR_c$ is in the syn position.

Furthermore, if in the general formula (I), the symbols $R_b$ and $R_c$ are different, diastereoisomers exist; it is to be understood that these isomeric forms and mixtures thereof fall within the scope of the present invention.

A/ According to the invention, the compounds of the general formula (I) can be prepared by reacting an acid of the general formula:

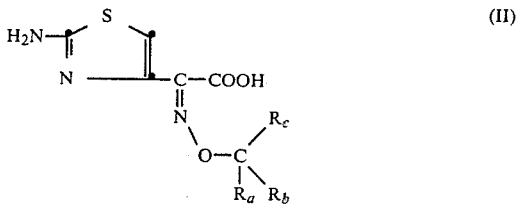

[in which $R_a$, $R_b$ and $R_c$ are as defined above and in which the amine group and, if appropriate, the carboxyl radical represented by $R_a$ have been protected], or a reactive derivative of this acid, with a 7-aminocephalosporin, or one of its salts, of the general formula:

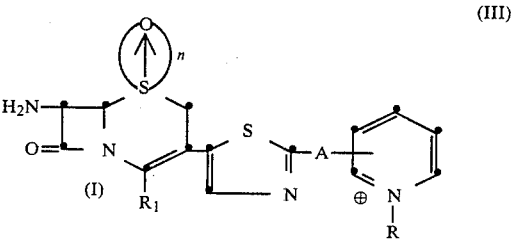

[in which the symbols A and n are as defined above, the symbol R is as defined above or represents a protected carboxymethyl radical and the symbol $R_1$ represents a carboxylato radical or a free or protected carboxyl radical (it being understood that if $R_1$ is other than carboxylato, the compound of the general formula (III) is in the form of a halide or sulphonate)] and then reducing the sulphoxide, if appropriate, and removing the protecting radicals.

The amine group of the acid of the general formula (II) can be protected by any easily removable group used in peptide chemistry which can be introduced and removed without affecting the rest of the molecule.

In particular, it is possible to use groups such as t-butoxycarbonyl, vinyloxycarbonyl, 2,2,2-trichloroethoxycarbonyl, chloroacetyl, trichloroacetyl, trifluoroacetyl, trityl, benzyl, benzyloxycarbonyl, p-nitrobenzyloxycarbonyl, p-methoxybenzyloxycarbonyl or formyl, or alternatively a diphenylphosphinoyl radical or a radical such as defined below by the general formula (XIV), which radicals can be introduced by applying the method described by A. MORIMOTO et al., J. Chem. Soc. Perkin I, 1109 (1980).

If appropriate, the carboxyl radical represented by $R_a$ and the carboxyl radical contained in R can be protected by easily removable acid-protecting groups, e.g. t-butyl, 2,2,2-trichloroethyl, benzhydryl, p-nitrobenzyl or p-methoxybenzyl.

If the symbol $R_1$ in the general formula (III) represents a protected carboxyl radical, the protecting group can be e.g. a group such as mentioned above.

If in the general formula (III), $R_1$ is other than carboxylato, the halide or the sulphonate used can be e.g. the iodide, the bromide or the chloride, an alkylsulphonate [in which the alkyl part, which contains 1 to 4 carbon atoms, can be substituted by one or more halogen atoms] or a phenylsulphonate [in which the phenyl radical can be optionally substituted by one or more substituents chosen from halogen atoms or alkyl or nitro radicals].

Furthermore, if a salt of the 7-aminocephalospor in of the general formula (III) is reacted, the salt used is e.g. a hydrochloride, a hydrobromide, a hydroiodide or a sulphonate defined as above.

If the product of the general formula (II) is used in its acid form, the condensation with the 7-aminocephalosporin of the general formula (III), in which $R_1$ is a protected carboxyl radical or a carboxylato radical, is carried out in the presence of a condensation agent such as a carbodiimide (e.g. dicyclohexylcarbodiimide), N,N′-carbonyldiimicazole or 2-ethoxy-1-ethoxycarbonyl-1,2-dihydroquinoline, at a temperature of between $-20°$ and $40°$ C., and the protecting groups are then removed, if appropriate.

If it is desired to use a reactive derivative of the acid of the general formula (II), it is possible to use the anhydride, a mixed anhydride or a reactive ester of the general formula:

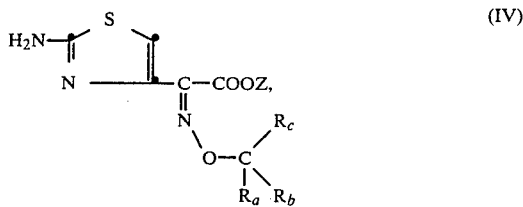

in which $R_a$, $R_b$ and $R_c$ are as defined above and Z represents a succinimido, benzotriazol-1-yl, 4-nitrophenyl, 2,4-dinitrophenyl, pentachlorophenyl or phthalimido radical.

It it also advantageous to use an acid halide. In the latter case, the hydrochloride of the acid chloride can be reacted.

If the anhydride, a mixed anhydride or an acid halide (which can all be prepared in situ) is used, the condensation is carried out in an inert organic solvent such as an ether (e.g. tetrahydrofuran or dioxane), a chlorinated solvent (e.g. chloroform or methylene chloride), an amide (e.g. dimethylformamide or dimethylacetamide) or a ketone (e.g. acetone), or in mixtures of the above solvents, in the presence of an acid acceptor such as an epoxide (e.g. propylene oxide) or such as an organic nitrogen base [e.g. pyridine, dimethylaminopyridine, N-methylmorpholine or a trialkylamine (e.g. triethylamine)], or in the presence of a silylating agent such as bis-trimethylsilylacetamide, or alternatively in an aqueous-organic medium in the presence of an alkaline condensation agent such as sodium bicarbonate, the reaction being carried out at a temperature of between $-40°$ and $40°$ C., and the protecting groups are then replaced by hydrogen atoms.

If a reactive ester of the general formula (IV) is used, the reaction is generally carried out in the presence of a tertiary amine (e.g. triethylamine) or a condensation agent such as mentioned above, in an organic solvent such as dimethylformamide, at a temperature of between $0°$ and $80°$ C., and the protecting groups are then replaced by hydrogen atoms.

If appropriate, the sulphoxide is reduced under the conditions described in German application No. A-2,637,176.

The acid-protecting groups can be removed e.g. by one of the following methods:

in the case of a t-butyl, p-methoxybenzyl or benzhydryl group: by treatment in an acid medium under the conditions described below for the removal of the amino-protecting trityl radical. In the case of the benzhydryl radical the reaction can be carried out in the presence of anisole or by treatment with aluminium chloride under the conditions described by T. Tsuji et al., Tet. Lett., 30, 2793 (1979);

in the case of a 2,2,2-trichloroethyl or p-nitrobenzyl group: by reduction (in particular by treatment with zinc in acetic acid or, in the case of the p-nitrobenzyl group, by hydrogenolysis).

The amine-protecting groups can be removed e.g. by one of the following methods:

in the case of a t-butoxycarbonyl, vinyloxycarbonyl, trityl, p-methoxybenzyloxycarbonyl or formyl radical: by treatment in an acid medium. It is preferred to use trifluoroacetic acid, the reaction being carried out at a temperature of between $0°$ and $20°$ C., or alternatively anhydrous or aqueous formic, phosphoric or polyphosphoric acid is used at a temperature of between $20°$ and $60°$ C., or alternatively para-toluenesulphonic or methanesulphonic acid is used in acetone or acetonitrile, at a temperature of between $20°$ C. and the reflux temperature of the reaction mixture. Under these conditions, the product of the general formula (I) can be obtained in the form of the trifluoroacetate, the solvate with formic acid, the phosphate, the methanesulphonate or the para-toluenesulphonate, from which the amine group can be freed by any method which is in itself known for obtaining an amine from one of its salts without affecting the rest of the molecule. The reaction is carried out, in particular, by bringing the product into contact with an ion exchange resin or by reacting it with an organic base;

in the case of a 2,2,2-trichloroethoxycarbonyl or p-nitrobenzyloxycarbonyl radical or a radical of the general formula (XIV) in which R′ is 2,2,2-trichloroethyl or nitrobenzyl: by reduction (in particular by treatment with zinc in acetic acid);

in the case of a chloroacetyl or trichloroacetyl radical: by application of the method described in French Pat. No. 2,243,199;

in the case of a benzyl or benzyloxycarbonyl radical: by catalytic hydrogenation;

in the case of a trifluoroacetyl radical: by treatment in a basic medium;

in the case of a diphenylphosphinoyl radical: in accordance with the method described by P. Haake et al., J. Am. Chem. Soc. 95, 8073 (1973);

in the case of a radical of the general formula (XIV): in accordance with the method described in Belgian Pat. No. 833,619.

B/ According to the invention, the compounds of the general formula (I) can also be obtained by reacting a halide or a sulphonate of the structure R—X, in which R is as defined above or represents a protected carboxymethyl radical and the symbol X represents a halogen atom chosen from iodine, bromine and chlorine, an alkylsulphonyloxy radical [in which the alkyl part, which contains 1 to 4 carbon atoms, is unsubstituted or substituted by one or more halogen atoms] or a phenylsulphonyloxy radical [in which the phenyl radical is unsubstituted or substituted by one or more substituents chosen from halogen atoms or alkyl or nitro radicals], with a cephalosporin derivative of the general formula:

[in which $R_2$ is a hydrogen atom or an amino-protecting radical, with a cephalosporin derivative of the general formula:

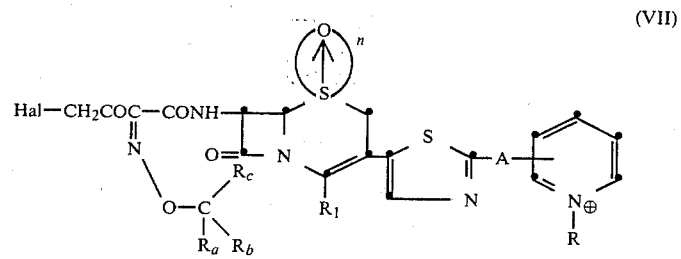

(VII)

[in which the symbols A, R, $R_1$ and n are as defined for the general formula (III) (it being understood that if $R_1$ is other than carboxylato, the product is in the form of a halide or sulphonate as defined above), the symbols $R_a, R_b$ and $R_c$ are as defined above, or $R_a$ represents a protected carboxyl radical, and Hal is a halogen atom]

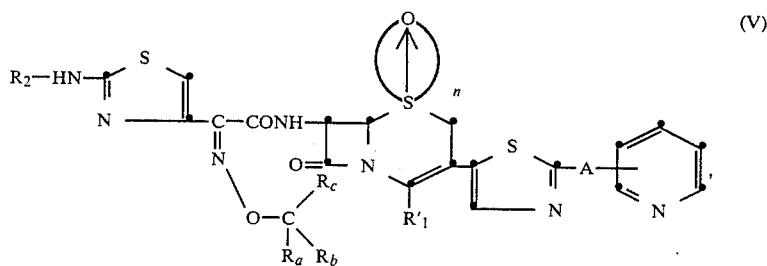

(V)

in which A, $R_a$, $R_b$, $R_c$ and n are as defined above, it being understood that if $R_a$ is a carboxyl radical, it can be free or protected, $R'_1$ is a free or protected carboxyl radical and $R_2$ is a hydrogen atom or an amino-protecting radical, and then reducing the sulphoxide obtained, if appropriate, and removing the protecting radicals.

The amino-protecting radicals represented by $R_2$ can be chosen from amongst the easily removable groups used in peptide chemistry, e.g. such as defined above.

If appropriate, the carboxyl radicals are protected by protecting groups such as defined above.

The reaction is generally carried out in an organic solvent such as an amide (e.g. dimethylformamide, hexamethylphosphorotriamide or dimethylacetamide), a nitrile (e.g. acetonitrile), a ketone (e.g. acetone) or a nitro derivative (e.g. nitromethane or nitrobenzene), or in a mixture of such solvents, at a temperature of between 0° and 80° C.

The reduction of the sulphoxide and the freeing of the protected radicals are carried out under the conditions described above.

C/ According to the invention, the compounds of the general formula (I) can also be obtained by reacting a thiourea of the general formula:

and then reducing the sulphoxide, if appropriate, and removing the protecting radicals, if appropriate.

If $R_2$ is an amino-protecting radical, it can be chosen from amongst the radicals mentioned above, except for chloroacetyl or trichloroacetyl.

It is advantageous to use a product in which the symbol Hal is a halogen atom chosen from chlorine and bromine.

The reaction is generally carried out in an aqueous, organic or aqueous-organic medium, e.g. in solvents such as alcohols (methanol and ethanol), ketones (acetone), chlorinated solvents (chloroform and methylene chloride), nitriles (acetonitrile), amides (dimethylformamide and dimethylacetamide), ethers (tetrahydrofuran and dioxane), esters (ethyl acetate) or acids (acetic acid and formic acid), or mixtures of these solvents, in the presence or absence of a base such as sodium hydroxide, potassium hydroxide, alkali metal carbonates, alkali metal bicarbonates, alkali metal salts of carboxylic acids (sodium formate or sodium acetate) or tertiary amines (triethylamine, trimethylamine or pyridine), at a temperature of between −30° and 60° C.

D/ According to the invention, the compounds of the general formula (I) in which A is a radical —NHCO— can also be obtained by converting thereto the corresponding amine of the general formula:

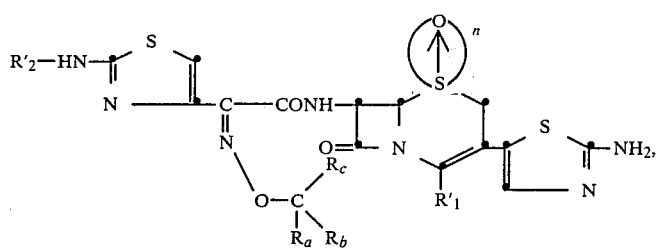

(VIII)

in which $R_a$, $R_b$, $R_c$, $R'_1$ and n are as defined above, it being understood that if $R_a$ is a carboxyl radical, it can be free or protected, and $R'_2$ is an amino-protecting radical, by any method which is known for forming an amide group without affecting the rest of the molecule, and then reducing the sulphoxide obtained, if appropriate, and removing the protecting radicals.

The amino-protecting radical $R'_2$ can be chosen from the groups mentioned above for process A. It can be removed after the reaction in accordance with the methods mentioned above under A/.

The reaction is generally carried out using a nicotinic or isonicotinic acid derivative in which the nitrogen atom is quaternised by a radical R such as defined above, it being understood that if R is carboxymethyl, the carboxyl radical is protected.

The reaction is advantageously carried out using an acid halide under the conditions described above for the reaction of the halide of the acid of the general formula (II) with the 7-aminocephalosporin derivative of the general formula (III).

If appropriate, the protection and freeing of the carboxyl radical and the reduction of the sulphoxide are carried out under the conditions described above.

The products of the general formula (II) can be prepared in accordance with the methods described in European patent application No. 53,961.

The 7-aminocephalosporin derivatives of the general formula (III) can be obtained from a product of the general formula:

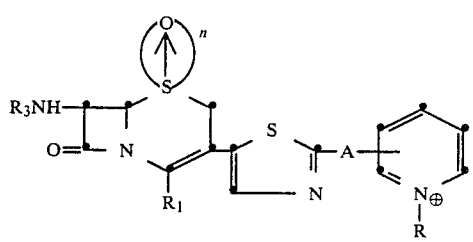

(IX)

[in which A, R, $R_1$ and n are as defined above for the general formula (III) (it being understood that if $R_1$ is other than the carboxylato radical, the product is in the form of a halide or sulphonate) and $R_3$ represents an easily removable radical] by removal of the radical $R_3$ or, if appropriate, successive or simultaneous removal of the radical $R_3$ and the protecting radicals contained in $R_1$ and R.

"Easily removable radical $R_3$" is to be understood as meaning e.g.:

(1) benzhydryl or trityl, (2) an acyl radical of the general formula:

$$R_4CO— \qquad (X),$$

in which $R_4$ represents:

(a) a hydrogen atom, an alkyl radical containing 1 to 7 carbon atoms or a methyl radical substituted by 1 to 3 halogen atoms, (b) a phenyl radical (which can be up to trisubstituted by halogen atoms or hydroxyl, nitro, cyano, trifluoromethyl, alkyl or alkoxy radicals) or a thien-2-yl or thien-3-yl radical, (c) a radical of the general formula:

$$R'_4—Y—CH_2— \qquad (Xa),$$

in which $R'_4$ is a phenyl radical which can be substituted by a halogen atom or by an alkyl, alkoxy or hydroxyl radical and Y is an oxygen or sulphur atom, or (d) an arylalkyl radical of the general formula:

$$R''_4CH_2— \qquad (Xb),$$

in which $R''_4$ is a phenyl radical which can be up to trisubstituted by hydroxyl, alkyl or alkoxy radicals, or a heterocyclic radical such as thien-2-yl or thien-3-yl or furan-2-yl or furan-3-yl, (3) a 5-aminoadipoyl radical in which the amine and acid groups are protected by protecting radicals such as defined above, (4) a radical of the general formula:

$$R_5OCO— \qquad (XI),$$

in which $R_5$ is an unsubstituted branched alkyl radical, a linear or branched alkyl radical carrying one or more substituents [such as halogen atoms, cyano, trialkylsilyl or phenyl radicals or a phenyl radical substituted by one or more halogen atoms or alkyl, alkoxy, nitro or phenyl radicals] or a quinolyl radical, or (5) a radical of the general formula:

$$\underset{(O)_n}{Ar—\overset{|}{S}—} \qquad (XIIa)$$

or $$ArSe—, \qquad (XIIb)$$

in which formulae the radical Ar is a phenyl radical optionally substituted by one or more halogen atoms or nitro or alkyl radicals and n is equal to 0 or 1, or alternatively (6) $R_3NH—$ can be replaced by a dialkylaminomethyleneamino radical or by a radical of the general formula:

$$Ar'—CH=N— \qquad (XIII),$$

in which Ar' is a phenyl radical optionally substituted by one or more radicals such as alkyl, alkoxy, hydroxyl or nitro, or (7) $R_3$ is a diphenylphosphinoyl radical or a radical of the general formula:

(XIV)

in which R' is alkyl, 2,2,2-trichloroethyl, phenyl or benzyl (these last two being optionally substituted by a halogen atom or by an alkyl, alkoxy or nitro radical), or the radicals R' together form an alkylene radical containing 2 or 3 carbon atoms.

The following radicals may be mentioned as examples of radicals $R_3$ which can be used: formyl, acetyl, trichloroacetyl, phenylacetyl, phenoxyacetyl, benzoyl, t-butoxycarbonyl, 2-chloro-1,1-dimethylethoxycarbonyl, 2,2,2-trichloroethoxycarbonyl, 2,2,2-trichloro-1,1-dimethylethoxycarbonyl, 2-cyano-1,1-dimethylethoxycarbonyl, 2-trimethylsilylethoxycarbonyl, benzyloxycarbonyl, p-methoxybenzyloxycarbonyl, 3,5-dimethoxybenzyloxycarbonyl, p-nitrobenzyloxycarbonyl, diphenylmethoxycarbonyl, 2-(bi-phenyl-4-yl)-isopropoxycarbonyl, quinolin-8-yl-oxycarbonyl, o-nitrophenylthio, p-nitrophenylthio, dimethoxyphosphoryl, diethoxyphosphoryl, diphenoxyphosphoryl and dibenzyloxyphosphoryl.

The following may be mentioned as examples of methyleneamino radicals defined above under (6): dimethylaminomethyleneamino, 3,4-dimethoxybenzylideneamino and 4-nitrobenzylideneamino.

The protecting radical can be removed by any known method for freeing an amine group without affecting the rest of the molecule.

The reaction is carried out, in particular, under the conditions described in Belgian Pat. No. 883,415 or described above under A/.

The cephalosporin derivatives of the general formula (IX) can be obtained by analogy with one of the processes B and D used for the preparation of the products according to the invention, namely:
either from a product of the general formula:

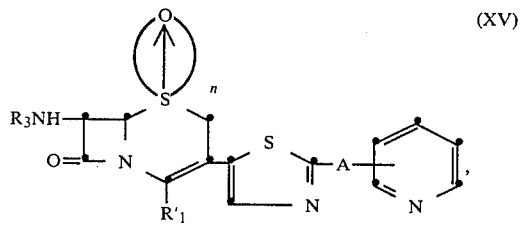

(XV)

in which A, $R'_1$, $R_3$ and n are defined as above, the reaction being carried out by analogy with process B/,
or, if the symbol A represents a radical —NHCO—, from a product of the general formula:

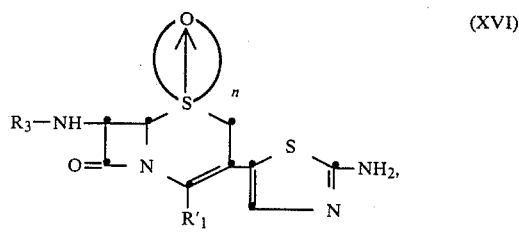

(XVI)

in which $R'_1$, $R_3$ and n are defined as above, the reaction being carried out by analogy with process D/.

The conditions under which these processes are carried out are identical to those used for the preparation of the products of the general formula (I).

The products of the general formulae (XV) and (XVI) can be prepared by reacting a product of the general formula:

$R_6$—CS—NH$_2$ (XVII), in which $R_6$ is an amino radical or a radical of the structure:

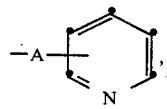

in which A is defined as above, with a cephalosporin derivative of the general formula:

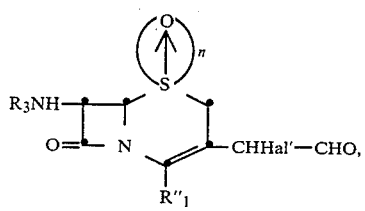

(XVIII)

in which $R_3$ and n are defined as above, R''$_1$ is a protected carboxyl radical such as defined for R'$_1$, and Hal' represents a halogen atom, and then, if appropriate, reacting the product with a dehydrating agent and, if appropriate, reducing the sulphoxide and removing the protecting groups.

The symbol Hal' can represent a chlorine, bromine or iodine atom.

The reaction is generally carried out in an organic or aqueous-organic medium, e.g. in solvents (or mixtures of solvents) such as alcohols (methanol and ethanol), ethers (tetrahydrofuran and dioxane), ketones (acetone), nitriles (acetonitrile), secondary amides (dimethylformamide and dimethylacetamide), esters (ethyl acetate) or acids (acetic acid and formic acid), in the presence or absence of a base (sodium hydroxide, potassium hydroxide, alkali metal carbonates or bicarbonates, alkali metal salts of carboxylic acids, or tertiary amines), at a temperature of between −50° C. and the reflux temperature of the reaction mixture.

It is sometimes preferable to introduce a dehydrating agent.

The following may be mentioned amongst the dehydrating agents which can be used: sulphonyl halides (e.g. tosyl chloride, methanesulphonyl chloride or a halide of the type R''SO$_2$Cl, in which R'' is alkyl, trifluoromethyl (or trichloromethyl) or phenyl optionally substituted by halogen, methyl or nitro), phosphoryl halides (e.g. phosphorus oxychloride) or sulphonyl chloride, in a basic solvent [pyridine or an amide (e.g. dimethylformamide, dimethylacetamide or hexamethylphosphorotriamide)] or in a chlorinated solvent (e.g. chloroform or methylene chloride), an ether (e.g. tetrahydrofuran), an ester, a ketone, a nitrile or an aromatic solvent, in the presence of a tertiary amine (e.g. pyridine, quinoline or triethylamine).

The products of the general formula (XVII) can be prepared by reacting ammonia gas with the corresponding alkyl or aryl isothiocyanate or dithiocarbamate, or by reacting hydrogen sulphide with the corresponding nitrile, in particular in accordance with the method mentioned below:

if $R_6$ represents nicotinoylamino or isonicotinoylamino: in accordance with the method of W. H. PIKE, Chem. Ber. 6, 755 (1873).

The cephalosporin derivatives of the general formula (XVIII) in which n=0 can be prepared by reacting a halogenating agent with an enamine of the general formula:

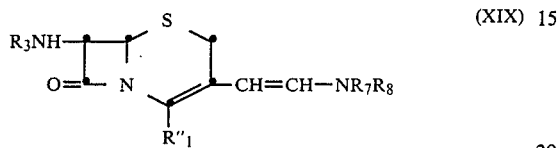

(XIX)

[[in which $R''_1$ and $R_3$ are defined as above and $R_7$ and $R_8$, which are identical or different, represent alkyl radicals (optionally substituted by an alkoxy or dialkylamino radical) or phenyl radicals, or form, together with the nitrogen atom to which they are attached, a 5-membered or 6-membered heterocyclic ring optionally containing another heteroatom chosen from amongst nitrogen, oxygen or sulphur, and optionally substituted by an alkyl radical]] and then hydrolysing the product formed.

By way of example, an enamine of the general formula (XIX) in which $R_7$ and $R_8$ each represent a methyl radical is used.

The following may be mentioned amongst the halogenating agents: halogens, N-halogenoamides [e.g. N-bromosuccinimide (or N-chlorosuccinimide), N-bromoacetamide (or N-chloroacetamide) and dibromohydantoin] and alkyl hypohalites (e.g. t-butyl hypochlorite, t-butyl hypobromite or ethyl hypochlorite).

The reaction is generally carried out in an organic solvent such as an ether (e.g. tetrahydrofuran or dioxane), a chlorinated solvent (e.g. methylene chloride or chloroform), an ester (e.g. ethyl acetate), an alcohol (e.g. methanol or ethanol), an amide (e.g. dimethylformamide or dimethylacetamide), a nitrile (e.g. acetonitrile) or a ketone (e.g. acetone), or in a mixture of these solvents, at a temperature of between −70° and 0° C.

The hydrolysis is carried out at a temperature of between −70° and 20° C.

It is not essential either to isolate or to purify the products of the general formula (XVIII) in order to use them according to the invention.

The cephalosporin derivatives of the general formula (XVIII) in which n=1 can be obtained by oxidising a product of the general formula (XVIII) in which n=0 by applying the methods described in German application No. 2,637,176.

The enamines of the general formula (XIX) can be prepared by applying the method described in Belgian Pat. No. 883,416, starting from cephalosporin derivatives of the general formula:

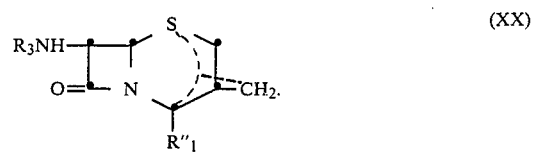

(XX)

The cephalosporin derivatives of the general formula (XX) can be obtained as described in Belgian Pat. No. 883,416 or, if $R_3$ is an easily removable radical such as defined above under (7), by applying the method described by A. MORIMOTO et al., J.C.S. Perkin I, 1109 (1980), starting from the corresponding halide $R_3$-Hal [which can itself be obtained in accordance with one of the methods described by K. SASSE, Methoden der organischen Chemie (Methods of Organic Chemistry), Volume 12, Part 2, page 274, Houben Weyl, Georg Thieme Verlag, Stuttgart (1964)].

The cephalosporin derivatives of the general formulae (V) and (VIII) can be prepared by applying process A described above for the preparation of the products according to the invention, i.e. by acylating a 7-aminocephalosporin of the general formula:

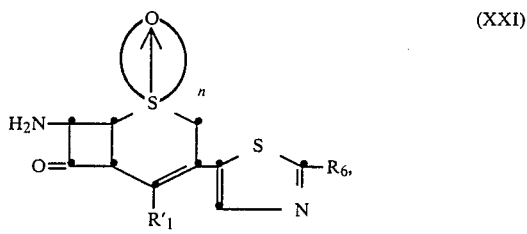

(XXI)

in which $R'_1$ $R_6$ and n are defined as above, and then, if appropriate, removing the protecting radicals.

It is understood that if $R_6$ represents an amino radical, it is preferably protected. The protection is effected by a group such as defined above for $R_2$ in the general formulae (V) and (VIII).

The acylation is carried out under the conditions described above for the preparation of the products according to the invention by process A.

Protecting radicals can be removed under the conditions described above.

The 7-aminocephalosporin of the general formula (XXI) can be obtained from a cephalosporin of the general formula (XV) or (XVI) (depending on the nature of the substituent $R_6$) by applying the methods described for the preparation of the 7-aminocephalosporin of the general formula (III).

It is understood that if $R_6$ represents an amino radical, it is preferably protected; the protection is effected by a group which is different from $R_3$, so that the protecting radical $R_3$ can be removed selectively.

The cephalosporin derivatives of the general formulae (V) and (VIII) can also be prepared from a cephalosporin of the general formula:

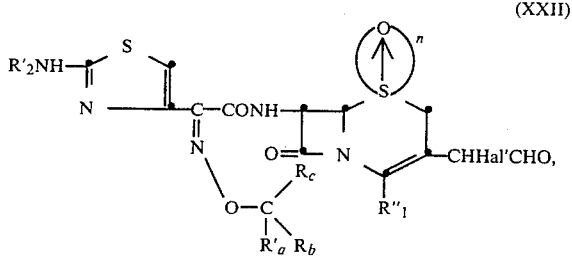

(XXII)

in which R″₁, R′₂, R_b, R_c, n and Hal′ are defined as above and R′_a is a hydrogen atom or a protected carboxyl radical, by analogy with the method described above for the preparation of the products of the general formulae (XV) and (XVI).

The symbol R′₂, which represents an amino-protecting radical, can be e.g. a t-butoxycarbonyl, 2,2,2-trichloroethoxycarbonyl, trityl, benzyl, benzyloxycarbonyl, formyl, trifluoroacetyl, p-nitrobenzyloxycarbonyl, p-methoxybenzyloxycarbonyl or diphenylphosphinoyl radical or a radical of the general formula (XIV).

The products of the general formula (XXII) in which n=0 can be obtained from an enamine of the general formula:

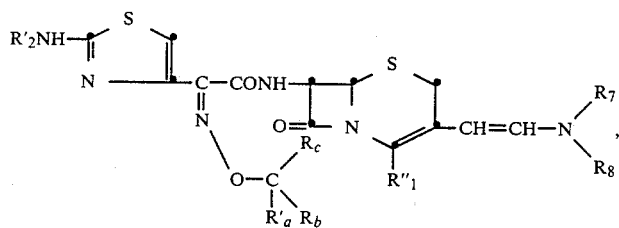

(XXIII)

in which R″₁, R′₂, R′_a, R_b, R_c, R₇ and R₈ are defined as above, the reaction being carried out by analogy with the method described for the preparation of the cephalosporins of the general formula (XVIII).

The products of the general formula (XXII) in which n=1 can be obtained by oxidising the corresponding product of the general formula (XXII) in which n=0, under the conditions described in German application No. 2,637,176.

The enamines of the general formula (XXIII) can be obtained in accordance with the method described in Belgian Pat. No. 883,416 or in European application No. 53,961.

The products of the general formula (VII) can be obtained by reacting an acid halide of the general formula:

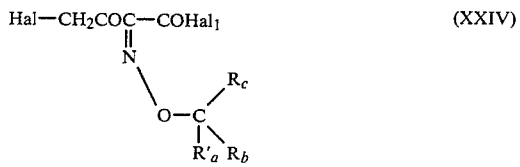

(XXIV)

in which Hal, R_b and R_c are defined as in the general formula (VII), R′_a is defined as in the general formula (XXII) and Hal₁ represents a chlorine or bromine atom, with a 7-aminocephalosporin of the general formula (III) and then, if appropriate, reducing the sulphoxide and removing the protecting radicals.

The reaction is generally carried out in an aqueous-organic medium, e.g. water/ether (tetrahydrofuran or dioxane), water/ketone (acetone) or water/chlorinated solvent (chloroform or methylene chloride), in the presence of an alkaline condensation agent such as an alkali metal bicarbonate (e.g. sodium bicarbonate), at a temperature of between −40° and 40° C.

The reaction can also be carried out by analogy with the method described in French application No. 2,399,418.

It is understood that if the radical R of the 7-aminocephalosporin contains a carboxyl radical, the latter is free or protected.

The products of the general formula (XXIV) can be prepared as described in European application No. 53,961.

The cephalospor n derivatives of the general formulae (V), (VIII), (XV), (XVI) and (XXI) in which n=1 can be obtained by oxidising the corresponding derivatives in which n=0, under the conditions described in German application No. 2,637,176.

The compounds according to the invention can be converted to addition salts with acids, in particular to addition salts with strong acids. These addition salts can be obtained by reacting the product with acids in suitable solvents. Examples of organic solvents used are alcohols, ketones, ethers or chlorinated solvents.

The products according to the present invention in which R_a is a carboxyl radical or R is a carboxymethyl radical can be converted to metal salts or to addition salts with nitrogen-containing bases in accordance with the methods which are in themselves known. These salts can be obtained by reacting a metal base (e.g. an alkali metal or alkaline earth metal base), ammonia gas or an amine with a compound according to the invention, in a suitable solvent such as an alcohol, an ether or water, or by means of an exchange reaction with a salt of an organic acid. The salt formed precipitates, if necessary after concentration of its solution, and is separated off by filtration or decantation. It can also be isolated from its solution by evaporation of the solvent, in particular by lyophilisation.

Examples which may be mentioned of pharmaceutically acceptable salts are the salts with alkali metals (sodium, potassium and lithium) or with alkaline earth metals (magnesium and calcium), the ammonium salts, the salts with nitrogen-containing bases (ethanolamine, diethanolamine, trimethylamine, triethylamine, methylamine, propylamine, diisopropylamine, N,N-dimethylethanolamine, benzylamine, dicyclohexylamine, N-benzyl-β-phenethylamine, N,N′-dibenzylethylenediamine, N-methylglucamine, diphenylenediamine, benzhydrylamine, quinine, choline, arginine, lysine, leucine and dibenzylamine) or the addition salts with mineral acids (the hydrochlorides, hydrobromides, sulphates, nitrates and phosphates) or with organic acids (the succinates, fumarates, maleates and p-toluenesulphonates).

The new products according to the present invention can be purified, if appropriate, by physical methods such as crystallisation, ultrafiltration or chromatography.

The new cephalosporin derivatives according to the present invention, and their pharmaceutically acceptable salts, exhibit particularly valuable antibacterial properties. They show a remarkable activity in vitro and in vivo against Gram-positive and Gram-negative germs.

In vitro, the products of the general formula (I) have been shown to be active at a concentration of between 1 and 30 μg/cc against staphylococcus strains sensitive to penicillin G (Staphylococcus aureus Smith) and at a concentration of between 0.01 and 1 μg/cc against Escherichia coli, NIHJ strain. Furthermore, the products of the general formula (I) in which $R_a$ is a carboxyl radical have been shown to be active at a concentrations of between 2 and 15 μg/cc against Pseudomonas aeruginosa Dalgleish.

In vivo, the products of the general formula (I) have been shown to be active at a dose of between 0.5 and 15 mg/kg per day, administered subcutaneously, against experimental infections caused in mice by Staphylococcus aureus Smith (sensitive to penicillin G).

The products of the general formula (I) have been shown to be non-toxic to mice at a dose of 1 mg/kg, administered subcutaneously.

Of particular value are the compounds of the general formula (I) in which the symbol A represents a single bond or a divalent radical chosen from —CH$_2$—, —NH— or —NHCO—, attached to the 3-position or 4-position of the pyridinio radical, the symbol R represents a methyl, carboxymethyl, carbamoylmethyl or benzyl radical, and either the symbols $R_a$, $R_b$ and $R_c$ each represent a hydrogen atom, or the symbol $R_a$ represents a carboxyl radical and the symbols $R_b$ and $R_c$ represent hydrogen atoms or methyl radicals, and n is equal to 0 or 1, and also their addition salts with acids, and, if appropriate, their metal salts or their addition salts with nitrogen-containing bases.

Amongst these compounds, those which are more especially active are the products of the general formula (I) in which the symbol A is a single bond or a radical —NH—, attached to the 3-position of the pyridinio radical the symbol R represents a methyl, carboxymethyl or carbamoylmethyl radical, and either the symbols $R_a$, $R_b$ and $R_c$ represent hydrogen atoms, or the symbol $R_a$ represents a carboxyl radical and the symbols $R_b$ and $R_c$ represent hydrogen atoms or methyl radicals, and n equals 0, and also their addition salts with acids, and, if appropriate, their metal salts or their addition salts with nitrogen-containing bases.

The examples which follow, which are given without implying a limitation, illustrate the present invention.

EXAMPLE 1

A solution of the syn isomer of 2-benzhydryloxycarbonyl-7-[2-methoxyimino-2-(2-tritylaminothiazol-4-yl)-acetamido]-8-oxo-3-[2-(pyridin-3-yl)-thiazol-5-yl]-5-thia-1-az abicyclo[4.2.0]oct-2-ene 5-oxide (14.9 g) and methyl iodide (1.07 cc) in N,N-dimethylformamide (60 cc) is stirred for 24 hours at 20° C. and filtered, and the filtrate is poured into ethyl acetate (600 cc). The precipitate formed is filtered off and washed with ethyl acetate (4×50 cc) and isopropyl ether (2×50 cc). The solid is crystallised from methylene chloride (70 cc) to give the syn isomer of 2-benzhydryloxycarbonyl-7-[2-methoxyimino-2-(2-tritylaminothiazol-4-yl)-acetamido]-3-[2-(1-methyl-3-pyridinio)-thiazol-5-yl]-8-oxo-5-thia-1- azabicyclo[4.2.0]oct-2-ene 5-oxide iodide (10.4 g) in the form of a yellow crystalline powder.

Infra-red spectrum (KBr, characteristic bands in cm$^{-1}$): 1800, 1740, 1520, 1500, 1450, 1220, 1040, 760, 705, 675.

Proton NMR spectrum (350 MHz, DMSO-d$_6$, δ in ppm, J in Hz): 3.86 (s, 3H, =N—O—CH$_3$); 3.87 and 4.50 (2d, 2H, —S—CH$_2$—); 4.47

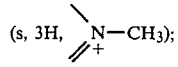

5.13 (d, J=5, 1H, —H in the 6-position); 5.97 (dd, J=7 and 5, 1H, H in the 7-position); 6.72 (s, 1H, H in the 5-position of the thiazole); 6.96 (s, 1H, —COO—CH(C$_6$H$_5$)$_2$); 6.90 to 7.4 (mt, 25H aromatic protons); 8.05 (s, 1H, —H in the 4-position of the thiazole); 8.23 (dd, J=8 and 6, 1H, —H in the 5-position of the pyridinio); 8.73 (d broad, J=8, 1H, H in the 4-position of the pyridinio); 8.79 (s, 1H, —NH—C(C$_6$H$_5$)$_3$); 9.04 (d, J=6, 1H, H in the 6-position of the pyridinio); 9.21 (d, J=7, 1H, —CO—NH—; 9.40 (s broad, 1H, —H in the 2-position of the pyridinio).

A solution of the syn isomer of 2-benzhydryloxycarbonyl-7-[2-methoxyimino-2-(2-tritylaminothiazol-4-yl)-acetamido]-3-[2-(1-methyl-3-pyridinio)-thiazol-5-yl]-8-oxo-5-t hia-1-azabicyclo[4.2.0]oct-2-ene 5-oxide iodide (10.4 g) in a mixture of methylene chloride (200 cc) and N,N-dimethylacetamide (50 cc), cooled to −10° C., is treated with phosphorus trichloride (1.8 cc) and then stirred at −5° C. for 40 minutes and filtered, and the filtrate is poured into ethyl acetate (1 liter). The precipitate is filtered off, washed with ethyl acetate (2×30 cc) and isopropyl ether (2×30 cc), taken up in methylene chloride (50 cc) and reprecipitated with ethyl acetate (250 cc). The solid is filtered off, washed again as above and dried to give the syn isomer of 2-benzhydryloxyc arbonyl-7-[2-methoxyimino-2-(2-tritylaminothiazol-4-yl)-acetamido]-3-[2-(1-methyl-3-pyridinio)-thiazol-5-yl]-8-oxo-5-thia-1-azabicyclo[4.2.0]oct-2-ene iodide (11.7 g) in the form of a yellow solid.

Proton NMR spectrum (250 MHz, DMSO-d$_6$, δ in ppm, J in Hz): 3.9 (s, 3H, =N—OCH$_3$); 3.93 and 4.06 (2d, J=19, 2H, —S—CH$_2$—); 4.47

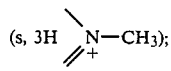

5.32 (d, J=5, 1H, —H in the 6-position); 5.93 (dd, J=8 and 5, 1H, —H in the 7-position; 6.81 (s, 1H, —H in the 5-position of the thiazole); 6.93 (s, 1H, —COO—CH(C$_6$H$_5$)$_2$); 6.90 to 7.4 (mt, 25H aromatic protons); 8.08 (s, 1H, —H in the 4-position of the thiazole); 8.24 (dd, J=8 and 6, 1H, —H in the 5-position of the pyridinio); 8.73 (d, J=8, 1H, H in the 4-position of the pyridinio); 9.09 (d, J=6, 1H, H in the 6-position of the pyridinio); 9.42 (s broad, 1H, —H in the 2-position of the pyridinio); 9.48 (b , 1H, —NH—C(C$_6$H$_5$)$_3$); 9.78 (d, J=8, 1H, —CO—NH—).

A solution of the syn isomer of 2-benzhydryloxycarbonyl-7-[2-methoxyimino-2-(2-tritylaminothiazol-4-yl)- acetamido]-3-[2-(1-methyl-3-pyridinio)-thiazol-5-yl]-8-oxo-5-thia-1-azabicyclo[4.2.0]oct-2-ene iodide (11.6 g) in a mixture of anisole (20 cc) and formic acid (150 cc) is heated for 30 minutes at 50° C. and then diluted with distilled water (50 cc) and heated for a further 30 minutes at 50° C. The solution is concentrated to dryness under reduced pressure (1 mm Hg; 0.13 kPa) at 40° C. The residue is taken up in ethanol (50 cc) and the solution is concentrated to dryness under reduced pressure (30 mm Hg; 4 kPa) at 40° C., this operation being repeated a further 2 times. The residue is solidified with ethanol (50 cc). The solid is filtered off, washed with ethanol (4×20 cc), acetone (3×20 cc), ethyl acetate (2×20 cc) cc) and ethyl ether (2×20 cc) and dried. This gives the crude syn isomer of 7-[2-(2-aminothiazol-4-yl)-2-methoxyiminoacetamido]-2-carboxylato-3-[2-(1-methyl-3-pyridinio)-thiazol-5-yl]-8-oxo-5-thia-1-azabicyclo[4.2.0]-oct-2-ene hydroiodide (7.6 g) in the form of a light brown solid, which is taken up in distilled water (500 cc) and ethyl acetate (250 cc); after filtration and decantation of the aqueous phase, the latter is washed with ethyl acetate (150 cc) and treated with basic IR 45 resin until a pH of 4.7 is reached. The resin is removed by filtration and the aqueous solution is lyophilised. The lyophilisate is solidified with distilled water (50 cc) to give the syn isomer of 7-[2-(2-aminothiazol-4-yl)-2-methoxyiminoacetamido]-2-carboxylato-3-[2-(1-methyl-3-pyridinio-thiazol-5-yl]-8-oxo-5-thia-1-azabicyclo[4.2.0]oct-2-ene (3.15 g) in the form of an orange powder.

Infra-red spectrum (KBr, characteristic bands in cm$^{-1}$): 3600–2500, 1765, 1670, 1610, 1530, 1380, 1030, 770, 675.

Proton NMR spectrum (250 MHz, DMSO-$d_6$, δ in ppm, J in Hz): 3.71 and 3.84 (2d, J=17, 2H, —S—CH$_2$—); 3.86 (s, 3H, =N—OCH$_3$); 4.43

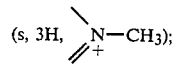
(s, 3H, N—CH$_3$);

5.15 (d, J=5, 1H, —H in the 6-position); 5.65 (dd, J=8 and 5, 1H, —H in the 7-position); 6.76 (s, 1H, —H in the 5-position of the thiazole); 7.27 (b, 2H, —NH$_2$); 8.08 (s, 1H, —H in the 4-position of the thiazole); 8.14 (dd, J=8 and 6, 1H, —H in the 5-position of the pyridinio); 8.83 (d, J=8, 1H, —H in the 4-position of the pyridinio); 8.98 (d, J=6, 1H, —H in the 6-position of the pyridinio);9.48 (s, 1H, —H in the 2-position of the pyridinio); 9.64 (d, J=8, 1H, —CONH—).

The syn isomer of 2-benzhydryloxycarbonyl-7-[2-methoxyimino-2-(2-tritylaminothiazol-4-yl)-acetamido]-8-oxo-3-[2-(pyridin-3-yl)-thiazol-5-yl]-5-thia-1-azabicyclo-[4.2.0]oct-2-ene 5-oxide can be prepared in the following manner:

A 2 M solution of phosgene in toluene (32.6 cc) is added dropwise to a solution of the syn form of 2-methoxyimino-2-(2-tritylaminothiazol-4-yl)-acetic acid (25 g) in a mixture of dry methylene chloride (500 cc) and N,N-dimethylacetamide (5.25 cc), cooled to −10° C. The reaction mixture is stirred for 3 hours 30 minutes at between −5° and 0° C. and N,N-dimethylacetamide (15.8 cc) and a solution of 7-amino-2-benzhydryloxycarbonyl-8-oxo-3-[2-(pyridin-3-yl)-thiazol-5-yl]-5-thia-1-azabicyclo-[4.2.0]oct-2-ene 5-oxide (26 g) in methylene chloride (200 cc) are then added at −5° C. The reaction mixture is stirred for 1 hour 30 minutes at between 0° and +5° C. and then for 16 hours at 20° C. and is then treated with a 5% strength solution of sodium bicarbonate (500 cc) and filtered. The organic phase is washed with a semi-saturated solution of sodium chloride (500 cc), dried over magnesium sulphate and concentrated to dryness under reduced pressure (30 mm Hg; 4 kPa) at 30° C. The residue is chromatographed on a column (height=52 cm, diameter=7 cm) of silica gel (0.06–0.2 mm), ethyl acetate being used as the eluent and 1 liter fractions being collected. Fractions 6 to 13 are combined and concentrated to dryness under reduced pressure (30 mm Hg; 4 kPa) at 30° C. to give the syn isomer of 2-benzhydryloxycarbonyl-7-[2-methoxyimino-2-(2-tritylaminothiazol-4-yl)-acetamido]-8-oxo-3-[2-(pyridin-3-yl)-thiazol-5-yl]-5-thia-1-azabicyclo[4.2.0]-oct-2-ene 5-oxide (20.2 g) in the form of a cream solid (by taking up the resulting hard foam in methylene chloride (80 cc) and precipitating the product with isopropyl ether (300 cc)).

Infra-red spectrum (KBr, characteristic bands in cm$^{-1}$): 1800, 1730, 1685, 1495, 1450, 1420, 1220, 1050, 55, 700.

Proton NMR spectrum (250 MHz, CDCl$_3$, δ in ppm, J in Hz): 3.38 and 3.99 (d broad and d, J=19, 2H, —SCH$_2$—); 4.09 (S, 3H, =N—O—CH$_3$); 4.67 (d broad, J=5, 1H, —H in the 6-position); 6.26 (dd, J=10 and 5, 1H, —H in the 7 position); 6.74 (s, 1H, —H in the 5-position of the thiazole); 6.96 (s, 1H, —COO—CH(C$_6$H$_5$)$_2$); 6.95 to 7.45 (b, aromatic protons and —NH—C(C$_6$H$_5$)$_3$); 7.37 (dd, J=8 and 5, —H in the 5-position of the pyridine); 7.58 (d, J=10, 1H, —CO—NH—); 7.60 (s, 1H, —H in the 4-position of the thiazole); 8.02 (ddd, J=8, 2 and 1.5, —H in the 4-position of the pyridine); 8.67 (dd, J=5 and 1.5, 1H, —H in the 6-position of the pyridine); 8.93 (d, J=2, 1H, —H in the 2-position of the pyridine).

EXAMPLE 2

A solution of the syn isomer of 2-benzhydryloxycarbonyl-7-[2-t-butoxycarbonylmethoxyimino-2-(2-tritylaminothiazol-4-yl)-acetamido]-8-oxo-3-[2-(pyridin-3-yl)-thiazol-5-yl]-5-thia-1-azabicyclo[4.2.0]oct-2-ene 5-oxide (3.5 g) and methyl iodide (0.23 cc) is left for 16 hours at 25° C., with protection from the light, and then poured into a mixture of ethyl acetate (100 cc) and isopropyl ether (150 cc). The precipitate is filtered off, washed with isopropyl ether (3×30 cc), taken up in methylene chloride (30 cc) and reprecipitated with a mixture of ethyl acetate and ethyl ether to give the syn isomer of 2-benzhydryloxycarbonyl-7-[2-t-butoxycarbonylmethoxyimino-2-(2-tritylaminothiazol-4-yl)-acetamido]-3-[2-(1-methyl-3-pyridinio)-thiazol-5-yl]-8-oxo-5-thia-1-azabicy clo[4.2.0]oct-2-ene 5-oxide iodide (3.7 g) in the form of a yellow solid.

Infra-red spectrum (KBr, characteristic bands in cm$^{-1}$): 3410, 1800, 1730, 1680, 1515, 1495, 1450, 1370, 1225, 1155, 750, 700, 670.

Proton NMR spectrum (250 MHz, DMSO-$d_6$, δ in ppm, J in Hz): 1.44 (s, 9H, —C(CH$_3$)$_3$); 3.88 and 4.41 (2d, J=19, 2H, —S—CH$_2$—); 4.47

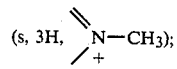
(s, 3H, N—CH$_3$);

4.56 (s, 2H, =N—O—CH$_2$—); 5.13 (d, J=5, 1H, —H in the 6-position); 6.03 (dd, J=8 and 5, 1H, —H in the 7-position); 6.88 (s, 1H, —H in the 5-position of the thiazole); 6.96 (s, 1H, —COO—CH(C₆H₅)₂); 6.9 to 7.4 (b, 25H, aromatic protons); 8.05 (s, 1H, —H in the 4-position of the thiazole); 8.22 (dd, J=8 and 6, 1H, —H in the 5-position of the pyridinio); 8.73 (d broad, J=8, 1H, —H in the 4-position of the pyridinio); 8 84 (s, 1H, —NH—C(C₆H₅)₃); 8.95 (d, J=8, 1H, —CO—NH—); 9.05 (d, J=6, 1H, —H in the 6-position of the pyridinio); 9.42 (s broad, 1H, —H in the 2-position of the pyridinio).

This product is redissolved in a mixture of methylene chloride (50 cc) and N,N-dimethylacetamide (1.15 cc), cooled to −10° C., to which phosphorus trichloride (0.54 cc) is added. After 30 minutes at −5° C., the reaction solution is poured into ethyl acetate (300 cc). The precipitate is filtered off and washed with ethyl acetate (4×30 cc) and then with isopropyl ether (50 cc) to give the syn isomer of 2-benzhydryloxycarbonyl-7-[2-t-butoxycarbonylmethoxyimino-2-(2-tritylaminothiazol-4-yl)-acetamido]-3-[2-(1-methyl-3-pyridinio)- thiazol-5-yl]-8-oxo-5 -thia-1-azabicyclo[4.2.0]oct-2-ene iodide (3.6 g) in the form of a yellow solid.

Infra-red spectrum (KBr, characteristic bands in cm⁻¹): 3420, 1790, 1730, 1690, 1520, 1500, 1450, 1230, 1160, 760, 705, 670.

Proton NMR spectrum (250 MHz, DMSO-d₆, δ in ppm, J in Hz): 1.46 (s, 9H, —C(CH₃)₃); 3.89 and 4.05 (2d, J=19, 2H, —S—CH₂—); 4.48

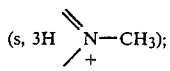
(s, 3H, ＼N—CH₃);
       ／+

4.56 (s, 2H, =N-OCH₂—); 5.32 (d, J=5, 1H, —H in the 6-position); 5.94 (dd, J=8 and 5, 1H, —H in the 7-position); 6.81 (s, 1H, —H in the 5-position of the thiazole); 6.93 (s, 1H, —COO—CH(C₆H₅)₂); 6.90 to 7.4 (mt, 25H, aromatic protons); 8.06 (s, 1H, —H in the 4-position of the thiazole); 8.23 (dd, J=8 and 6, 1H, —H in the 5-position of the pyridinio); 8.74 (d broad, J=8, 1H, —H in the 4-position of the pyridinio); 9.04 (s, 1H, —NH—C(C₆H₅)₃); 9.06 (d, J=6, 1H, —H in the 6-position of the pyridinio); 9.40 (s, 1H, —H in the 2-position of the pyridinio); 9.68 (d, J=8, 1H, —CO—NH—).

A solution of the syn isomer of 2-benzhydryloxycarbonyl-7-[2-t-butoxycarbonylmethoxyimino-2-(2-tritylaminothiazol-4-yl)-acetamido]-3-[2-(1-methyl-3-pyridinio)-thiazol-5-yl]-8 1 -oxo-5-thia-1-azabicyclo[4.2.0]oct-2-ene iodide (3.6 g) in a mixture of formic acid (50 cc) and anisole (6 cc) is stirred for 30 minutes at 50° C. and then for a further 15 minutes at the same temperature after the addition of distilled water (15 cc). After concentration to dryness under reduced pressure (0.1 mm Hg; 13 Pa) at 40° C., the residue is taken up in absolute ethanol (50 cc) which is evaporated off under reduced pressure (30 mm Hg; 4 kPa) at 40° C. This operation is repeated a further 2 times and the residue is then solidified with ethanol (30 cc). The precipitate is washed again with ethanol (3×10 cc), acetone (3×10 cc) and ethyl ether (3×10 cc) and then dried to give the crude syn isomer of 7-{2-(2-aminothiazol-4-yl)-2-carboxymethoxyiminoacetamido}-2-carboxylato-3-[2-(1-methyl-3-pyridinio)-thiazol-5-yl]-5-thia-1-azabicyclo[4.2.0]oct-2-ene hydroiodide (2.6 g) in the form of a yellow solid. The crude product obtained is taken up in a mixture of ethyl acetate (100 cc) and distilled water (250 cc) by stirring for 20 minutes at 20° C.; after filtration and decantation of the aqueous phase, the latter is washed again with ethyl acetate (100 cc) and then treated with basic IR 45 resin (30 cc) until the pH reaches a value of 3.5. The resin is removed by filtration and the solution is lyophilised. The solid obtained is rendered more solid with water (10 cc) and the product is filtered off and washed with water (2×1 cc) to give the syn isomer of 7-[2-(2-aminothiazol-4-yl)-2-carboxymethoxyiminoacetamido]-2-carboxylato-3-[2-(1-methyl-3-pyridinio)-thiazol-5-yl]-5-thia-1-azabicyclo[4.2.-0]oct-2-ene (0.64 g) in the form of a yellow solid.

Infra-red spectrum (KBr, characteristic bands in cm⁻¹): 3600–2000, 1770, 1675, 1615, 1530, 1360, 1040, 670.

Proton NMR spectrum (350 MHz, DMSO-d₆, δ in ppm, J in Hz): 3.63 and 3.76 (2d, J=19, 2H, —S—CH₂—); 4.43

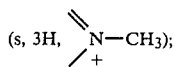
(s, 3H, ＼N—CH₃);
       ／+

4.56 (s, 2H, =N—O—CH₂—); 5.15 (d, J=5, 1H, —H in the 6-position); 5.78 (dd, J=9 and 5, 1H, —H in the 7-position); 6.83 (s, 1H, —H in the 5-position of the thiazole); 7.25 (b, 2H, —NH₂); 7.97 (S, 1H, —H in the 4-position of the thiazole); 8.08 (dd, J=7.5 and 5, 1H, —H in the 5-position of the pyridinio); 8.78 (d, J=7.5, 1H, —H in the 4-position of the pyridinio); 9.09 (d, J=5, 1H, —H in the 6-position of the pyridinio); 9.43 (s, 1H, —H in the 2-position of the pyridinio); 10.19 (b, 1H, —CO—NH—).

The syn isomer of 2-benzhydryloxycarbonyl-7-[2-t-butoxycarbonylmethoxyimino-2-(2-tritylaminothiazol-4-yl)-acetamido]-8-oxo-3-[2-(pyridin-3-yl)-thiazol-5-yl]-5-thia-1- azabicyclo[4.2.0]oct-2-ene 5-oxide can be obtained in the following manner:

A solution of 2-benzhydryloxycarbonyl-7-t-butoxycarbonylamino-8-oxo-3-[2-(pyridin-3-yl)-thiazol-5-yl]-5-thia-1-azabicyclo[4.2.0]oct-2-ene 5-oxide (6 g) in acetonitrile (60 cc) containing methanesulphonic acid (6 cc) is stirred for 6 minutes at 20° C. The reaction mixture is poured into a saturated solution of sodium bicarbonate (800 cc) and extracted with ethyl acetate (400 cc). The organic phase is washed with a saturated solution of sodium chloride (400 cc), dried over sodium sulphate and concentrated to dryness under reduced pressure (30 mm Hg; 4 kPa) at 40° C. to give crude 7-amino-2-benzhydryloxycarbonyl-8-oxo-3-[2-(pyridin-3-yl)-thiazol-5-yl]-5-thia-1-azabicyclo[4.2.0]oct-2-ene 5-oxide (4.2 g) in the form of a beige solid (Rf=0.5, silica gel chromatography plate eluted with a 90/10 by volume mixture of methylene chloride and ethanol). This product is taken up in methylene chloride (120 cc) to which the syn isomer of 2-t-butoxycarbonylmethoxyimino-2-(2-tritylaminothiazol-4-yl)-acetic acid (5.15 g) is added, followed by N,N-dimethylformamide (30 cc) and 4-dimethylaminopyridine (0.06 g). The solution is cooled to +5° C. and N,N'-dicyclohexylcarbodiimide (1.96 g) is then added. The mixture is stirred for 1½ hours at 5° C., then for 1½ hours at 20° C. and then for a further 5 minutes at 20° C. after the addition of acetic acid (0.2 cc). The methylene chloride is evaporated off under reduced pressure (30 mm Hg; 4 kPa) at 30° C. and the residue is taken up in ethyl acetate (100 cc). After filtration and washing successively with water (200 cc), a 5% strength solution of sodium bicarbonate (200 cc) and a saturated solution of sodium chloride (200 cc), the organic phase is dried over sodium sulphate and concentrated to dryness under reduced pressure (30 mm Hg; 4 kPa) at 30° C. The residue is chromatographed on a column of diameter 4 cm containing silica (0.06–0.2 mm) (400 cc), elution being carried out successively with the following mixtures (by volume) of cyclohexane and ethyl acetate: 50/50 mixture (4 liters), 40/60 mixture (1 liter), 30/70 mixture (1 liter) and 20/80 mixture (1 liter), and then with ethyl acetate (3 liters), and 250 cc fractions being collected. Fractions 29 to 38 are combined and concentrated to dryness under reduced pressure (30 mm Hg; 4 kPa) at 40° C. The hard foam obtained is solidified with ethyl ether to give the syn isomer of 2-benzhydryloxycarbonyl-7-[2-t-butoxycarbonylmethoxyimino-2-(2-tritylaminothiazol-4-yl)-acetamido]-8-oxo-3-[2-(pyridin-3-yl)-thiazol-5-yl]-5-thia-1-azabicyclo[4.2.0 ]-oct-2-ene 5-oxide (3.6 g) in the form of a cream solid.

Infra-red spectrum (KBr, characteristic bands in cm$^{-1}$): 3400, 1805, 1730, 1690, 1520, 1500, 1450, 1370, 1230, 1160, 755, 705.

Proton NMR spectrum (250 MHz, DMSO-d$_6$, $\delta$ in ppm, J in Hz): 1.45 (s, 9H, —C(CH$_3$)$_3$); 3.85 and 4.40 (2d, J=19, 2H, —S—CH$_2$—); 4.57 (s, 2H, =N—OCH$_2$—); 5.13 (d, J=4.5, 1H, —H in the 6-position); 6.03 (dd, J=7.5 and 4.5, 1H, —H in the 7-position); 6.92 (s, 1H, —H in the 5-position of the thiazole); 6.99 (s, 1H, —COO—CH(C$_6$H$_5$)$_2$); 6.95 to 7.45 (mt, 25H, aromatic protons); 7.57 (ddd, J=8.5 and 0.5, 1H, —H in the 5-position of the pyridine); 7.95 (s, 1H, —H in the 4-position of the thiazole); 8.1 (ddd, J=8, 2 and 1.5, 1H, H in the 4-position of the pyridine); 8.71 (dd, J=5 and 1.5, 1H, —H in the 6-position of the pyridine); 8.89 (s, 1H, —NH—C(C$_6$H$_5$)$_3$); 8.93 (dd, J=2 and 0.5, 1H, H in the 2-position of the pyridine); 8.99 (d, J=7.5, 1H, —CONH—).

The 2-benzhydryloxycarbonyl-7-t-butoxycarbonylamino-8-oxo-3-[2-(pyridin-3-yl)-thiazol-5-yl]-5-thia-1-azabicyclo[4.2.0]oct-2-ene 5-oxide can be prepared in the following manner:

A solution of meta-chloroperbenzoic acid (8.65 g) in methylene chloride (300 cc) is added in the course of 40 minutes to a solution, cooled to −10° C., of 2-benzhydryloxycarbonyl-7-t-butoxycarbonylamino-8-oxo-3-[2-(pyridin-3-yl)-thiazol-5-yl]-5-thia-1-azabicyclo[4 2.0]oct-2-en e (31.3 g) in methylene chloride (300 cc). A 5% strength solution of sodium bicarbonate (500 cc) is added. The organic phase is washed with a saturated solution of sodium chloride (500 cc), dried over magnesium sulphate and concentrated to dryness under reduced pressure (30 mm Hg; 4 kPa) at 30° C. The residue is solidified with ethyl ether to give 2-benzhydryloxycarbonyl-7-t-butoxycarbonylamino-8-oxo-3-[2-(pyridin-3-yl)-thiazol-5-yl]-5-thia-1-azabicyclo[4.2.0]oct-2-ene 5-oxide (27.7 g) in the form of a cream solid.

Infra-red spectrum (CHBr$_3$, characteristic bands in cm$^{-1}$): 3410, 1800, 1720, 1505, 1370, 1235, 1050, 760, 745.

Proton NMR spectrum (250 MHz, CDCl$_3$, $\delta$ in ppm, J in Hz): 1.5 (s, 9H, —C(CH$_3$)$_3$); 3.35 and 4.02 (dd and d, J=19 and 1 and J=19, 2H, —S—CH$_2$—); 4.58 (d broad, J=5, 1H, —H in the 6-position); 5.85 (d, J=10, 1H, —CO—NH—); 5.94 (dd, J=10 and 5, 1H, —H in the 7-position); 6.96 (s, 1H, —COO—CH(C$_6$H$_5$)$_2$). 6.90 to 7.40 (mt, aromatic protons); 7.36 (dd, $\overline{J}$=8 and 5, 1H, —H in the 5-position of the pyridine); 7.61 (s, 1H, —H in the 4-position of the thiazole); 8.02 (ddd, J=8, 2 and 1.5, 1H, —H in the 4-position of the pyridine); 8.67 (dd, J=5 and 1.5, 1H, —H in the 6-position of the pyridine); 8.93 (d, J=2, 1H, —H in the 2-position of the pyridine).

The 2-benzhydryloxycarbonyl-7-t-butoxycarbonylamino-8-oxo-3-[2-(pyridin-3-yl)-thiazol-5-yl]-5-thia-1-azabicyclo[4.2.0]oct-2-ene can be prepared in the following manner:

Thionicotinamide (28.2 g) and pyridine (16.5 cc) are added to a solution of 2-benzhydryloxycarbonyl-3-(1-bromo-2-oxoethyl)-7-t-butoxycarbonylamino-8-oxo-5-thia-1-azabicyclo[4.2.0]oct-2-ene (mixture of the diastereoisomers) (120 g) in tetrahydrofuran (1,200 cc). The reaction mixture is stirred at 50° C. for 80 minutes. After cooling to +5° C., methanesulphonyl chloride (15.8 cc) and triethylamine (57.3 cc) are added successively in the course of 5 minutes. The reaction mixture is kept for 30 minutes at +5° C. and then reheated to 20° C. and poured into a mixture of ethyl acetate (1 liter) and a 5% strength solution of sodium bicarbonate (2 liters). The organic phase is washed with a 5% strength solution of sodium bicarbonate (2 liters) and then with a semi-saturated solution of sodium chloride (2 liters). After drying over magnesium sulphate and evaporation of the solvent to dryness under reduced pressure (4 kPa) at 30° C., the residue obtained is chromatographed on a column of diameter 9 cm containing silica gel (0.06–0.2 mm) (3.4 liters), 1 liter. fractions being collected. Elution is carried out successively with: methylene chloride (11 liters) and then the following mixtures (proportions by volume) of methylene chloride and ethyl acetate: 94/6 (16 liters), 88/12 (4 liters), 75/25 (12 liters) and 70/30 (10 liters). Fractions 32 to 52 are combined and concentrated to dryness and the residue is solidified with isopropyl ether to give 2-benzhydryloxycarbonyl-7-t-butoxycarbonylamino-8-oxo-3-[2-(pyridin-3-yl)-thiazol-5-yl]-5-thia-1-azabicyclo[4.2.0]-oct-2-ene (37.1 g) in the form of a beige solid.

Infra-red spectrum (CHBr$_3$, characteristic bands in cm$^{-1}$): 3430, 1780, 1725, 1590, 1575, 1510, 1460, 1420, 1370, 1240, 810, 765, 750.

Proton NMR spectrum (250 MHz, CDCl$_3$, $\delta$ in ppm, J in Hz): 1.49 (s, 9H, —C(CH$_3$)$_3$); 3.61 and 3.78 (2d, J=19, 2H, —SCH$_2$—); 5.1 (d, J=5, 1H, —H in the 6-position); 5.48 (d, J=10, 1H, —CO—NH—); 5.76 (dd, J=10 and 5, 1H, —H in the 7-position); 6.95 (s, 1H, —COOCHC$_6$H$_5$)$_2$); 6.90 to 7.4 (mt, aromatic protons); 7.38 (ddd, $\overline{J}$=7.5, 5 and 0.5, —H in the 5-position of the pyridine); 7.59 (s, 1H, H in the 4-position of the thiazole ; 8.04 (ddd, J=7.5, 2 and 1.5, 1H, —H in the 4-position of the pyridine); 8.67 (dd, J=5 and 1.5, 1H, —H in the 6-position of the pyridine); 8.94 (d, J=2, 1H, —H in the 2-position of the pyridine).

The 2-benzhydryloxycarbonyl-3-(1-bromo-2-oxoethyl)-7-t-butoxycarbonylamino-8-oxo-5-thia-1-azabicyclo[4.2.0]-oct-2-ene (mixture of the diastereoisomers) can be prepared in the following manner:

A solution of bromine (0.2 cc) in dry methylene chloride (2 cc) is added dropwise, in the course of 5 minutes, to a solution, cooled to −55° C., of 2-benzhydryloxycarbonyl-7-t-butoxycarbonylamino-3-(2-dimethylaminovinyl)-8-oxo-5-thia-1-azabicyclo[4.2.0]oct-2-ene (E isomer) (2 g) in dry tetrahydrofuran (11 cc). The reaction mixture is stirred for 1 hour at −60° C. and then poured into a mixture of ethyl acetate (200 cc) and iced water (200 cc). The organic layer is washed with a semi-saturated solution of sodium bicarbonate (100 cc) and then with water (100 cc) and a semi-saturated solution of sodium chloride (100 cc) and dried over sodium sulphate in the presence of decolorising charcoal. After filtration the solvent is evaporated off under reduced pressure (30 mm Hg; 4 kPa) at 30° C. The residue is taken up in isopropyl ether (50 cc), which is evaporated off under reduced pressure (30 mm Hg; 4 kPa) at 30° C. This gives 2-benzhydryloxycarbonyl-3-(1-bromo-2-oxoethyl)-7-t-butoxycarbonylamino-8-oxo-5-thia-1-azabicyclo[4.2.0]oct-2-ene (1.8 g) in the form of a light beige solid (mixture of the two epimers of the bromoaldehyde).

Infra-red spectrum (CHBr$_3$), characteristic bands (cm$^{-1}$): 3420, 1790, 1725, 1505, 1455, 1390, 1370, 1245, 1225, 760, 745.

Proton NMR spectrum (CDCl$_3$, 350 MHz, δ in ppm, J in hz):

Epimer A 1.42 (s, 9H, (CH$_3$)$_3$C—); 3.71 and 3.55 (AB type, J=17.5, 2H, —SCH$_2$—); 5.06 (d, J=4, 1H, H in the 6-position); 5.22 (d, J=9, 1H, —NH—); 5.65 (dd, J=4 and 9, 1H, H in the 7-position); 6.01 (s, 1H, —CHBr—); 6.99 (s, 1H, —CHAr$_2$); 7.3 to 7.5 (m, 10H, aromatic protons); 9.31 (s, 1H, —CHO).

Epimer B 1.42 (s, 9H, (CH$_3$)$_3$C—); 3.35 and 3.65 (AB type, J=17.5, 2H, —SCH$_2$—); 5.01 (d, J=4, 1H, H in the 6-position); 5.29 (d, J=9, 1H, —NH—); 5.72 (dd, J=4 and 9, 1H, H in the 7-position); 6.00 (s, 1H, —CHBr—); 6.92 (s, 1H, —CHAr$_2$); 7.3 to 7.5 (m, 10H, aromatic protons); 9.30 (s, 1H, —CHO).

The 2-benzhydryloxycarbonyl-7-t-butoxycarbonylamino-3-(2-dimethylaminovinyl)-8-oxo-5-thia-1-azabicyclo[4.2.0]oct-2-ene (E isomer) can be prepared as described in Belgian Patent No. 883,415.

EXAMPLE 3

A solution of the syn isomer of 2-benzhydryloxycarbonyl-7-[2-(2-t-butoxycarbonylprop-2-yl)-oxyimino-2-(2-tritylaminothiazol-4-yl)-acetamido]-8-oxo-3-[2-(pyridin-3-yl)-thiazol -5-yl]-5-thia-1-azabicyclo[4.2.0]oct-2-ene 5-oxide (8.5 g) in N,N-dimethylformamide (40 cc) containing methyl iodide (0.55 cc) is treated in accordance with the procedure described in Example 2 to give the syn isomer of 2-benzhydryloxycarbonyl-7-[2-(2-t-butoxycarbonylprop-2-yl)-oxyimino-2-(2-tritylaminothiazol-4-yl)-acetamido]-3-[2-(1-methyl-3-pyridinio)-thiazol-5-yl]-8-oxo-5-thia-1-azabicyclo[4.2.0]oct-2-ene 5-oxide iodide (8 g) in the form of a yellow solid.

Infra-red spectrum (KBr, characteristic bands in cm$^{-1}$): 3380, 1800, 1730, 1685, 1515, 1495, 1450, 1370, 1140, 755, 700, 670.

Proton NMR spectrum (350 MHz, DMSO-d$_6$, δ in ppm, J in Hz): 1.37 (s, 9H, —C(CH$_3$)$_3$); 1.46 (2s, 6H, >C(CH$_3$)$_2$); 3.91 and 4.5 (2d, J=19, 2H, —S—CH$_2$—); 4.47

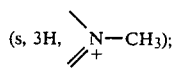
(s, 3H, >N—CH$_3$);

5.16 (d, J=4.5, 1H, —H in the 6-position); 6.07 (dd, J=8 and 5, 1H, —H in the 7-position); 6.80 (s, 1H, —H in the 5-position of the thiazole); 6.97 (s, 1H, —COO—CH(C$_6$H$_5$)$_2$); 6.90 to 7.4 (mt, aromatic protons); 8.1 (s, 1H, —H in the 4-position of the thiazole); 8.25 (dd, J=8 and 6, 1H, —H in the 5-position of the pyridinio); 8.4 (d, J=8, 1H, —CO—NH—); 8.74 (d, J=8, 1H, —H in the 4-position of the pyridinio); 8.76 (s, 1H, —NH—C(C$_6$H$_5$)$_3$); 9.06 (d, J=6, 1H, —H in the 6-position of the pyridinio); 9.42 (s, 1H, —H in the 2-position of the pyridinio).

A solution of the syn isomer of 2-benzhydryloxycarbonyl-7-[2-(2-t-butoxycarbonylprop-2-yl)-oxyimino-2-(2-tritylaminothiazol-4-yl)-acetamido]-3-[2-(1-methyl-3-pyridinio) -thia zol-5-yl]-8-oxo-5-thia-1-azabicyclo[4.2.0]oct-2-ene 5-oxide iodide (8 g) in a mixture of methylene chloride (100 cc) and N,N-dimethylacetamide (2.26 cc) is treated with phosphorus trichloride (0.96 cc) in accordance with the procedure of Example 2 to give the syn isomer of 2-benzhydryloxycarbonyl-7-[2-(2-t-butoxycarbonylprop-2-yl)-oxyimino-2-(2-tritylaminothiazol-4-yl)-acetamido]-3-[2-(1-methyl-3-pyridinio)-thiazol-5-yl]-8 - oxo-5-thia-1-azabicyclo[4.2.0]oct-2-ene (8 g) in the form of a yellow solid.

Infra-red spectrum (KBr, characteristic bands in cm$^{-1}$): 1790, 1730, 1680, 1520, 1495, 1450, 1370, 1140, 755, 700, 670.

Proton NMR spectrum (350 MHz, DMSO-d$_6$, δ in ppm, J in Hz): 1.4 (s, 9H, —C(CH$_3$)$_3$); 1.47 and 1.49 (2s, 6H, >C(CH$_3$)$_2$); 3.92 and 4.09 (2d, J=19, 2H, —S—CH$_2$—); 4.48

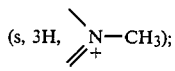
(s, 3H, >N—CH$_3$);

5.34 (d, J =5, 1H, —H in the 6-position); 5.95 (dd, J =8 and 5, 1H, —H in the 7-position); 6.80 (s, 1H, —H in the 5-position of the thiazole); 6.94 (s, 1H, —COO—CH(C$_6$H$_5$)$_2$); 6.9 to 7.4 (mt, aromatic protons); 8.10 (s, 1H, —H in the 4-position of the thiazole); 8.24 (dd, J =8 and 6, 1H, H in the 5-position of the pyridinio); 8.73 (d, J =8, 1H, —H in the 4-position of the pyridinio); 9.09 (d, J =6, 1H, —H in the 6-position of the pyridinio); 9.42 (s, 1H, —H in the 2-position of the pyridinio); 9.61 (d, J =8, 1H, —CO—NH—); 9.75 ( b, 1H, —NH—C(C$_6$H$_5$)$_3$).

A solution of the syn isomer of 2- benzhydryloxycarbonyl-7-[2(2-t-butoxycarbonylprop-2-yl)-oxyimino-2-(2-tritylaminothiazol-4-yl)-acetamido]-3-[2-(1-methyl-3-pyridinio )-thiazol-5-yl]-8-oxo-5-thia-1-azabicyclo-[4.2.0]oct-2-ene (8 g) in formic acid (160 cc) containing anisole (16 cc) is treated in accordance with the procedure described in Example 2 to give the syn isomer of 7-[2-(2-aminothiazol-4-yl)-2-(2-carboxyprop-2-yl)-oxyiminoacetamido] -2-carboxylato-3-[2-(1-methyl -3-pyridinio)-thiazol-5-yl]-8-oxo-5-thia-1-azabicyclo[4.2.0]oct-2-ene in the form of the crude hydroiodide (4.5 g). The crude product obtained is treated with basic IR 45 resin in accordance with the procedure of Example 2 to give the syn isomer of 7-[2-(2-aminothiazol-4-yl)-2-(2-carboxyprop-2-yl)-oxyiminoacetamido]-2-carboxylato-3-[2-(1-methyl-3-pyridinio)thiazol-5-yl]-8-oxo-5-thia-1-azabicyclo[4.2.0]oct-2-ene (1.4 g) in the form of a yellow solid.

Infra-red spectrum (KBr, characteristic bands in cm$^{-1}$): 3380, 3250, 3100–2300, 1770, 1680, 1610, 1520, 1360, 1160, 670.

Proton NMR spectrum (250 MHz, DMSO-d$_6$, δ in ppm, J in Hz): 1.47 and 1.52 (2s, 6H, >C(CH$_3$)$_2$); 3.60 to 3.90 (mt, —S—CH$_2$—); 4.4

(s, 3H, 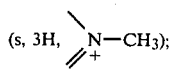

5.16 (d, J =5, 1H, —H in the 6-position); 5.79 (dd, J =9 and 5, 1H, —H in the 7-position); 6.76 (s, 1H, —H in the 5-position of the thiazole); 7.32 (b, 2H, —NH₂); 7.98 (s, 1H, —H in the 4-position of the thiazole); 8.07 (mt, 1H, —H in the 5-position of the pyridinio); 8.75 (d, J =7.5, 1H, —H in the 4-position of the pyridinio):9.06 (mt, 1H, —H in the 6-position of the pyridinio):9.39 (s broad, 1H, —H in the 2-position of the pyridinio); 9.89 (b, 1H, —CO—NH—).

The syn isomer of 2-benzhydryloxycarbonyl-7-[2-(2-t-butoxycarbonylprop-2-yl)-oxyimino-2-(2-tritylamino-thiazol-4-yl)-acetamido]-8-oxo-3-[2-(pyridin-3-yl)-thiazol-5-yl]-5-thia-1-azabicyclo[4.2.0]oct-2-ene 5-oxide can be prepared in the following manner:

A solution of 7-amino-2-benzhydryloxycarbonyl-8-oxo-3-[2-(pyridin-3-yl)-thiazol-5-yl]-5-thia-1-azabicyclo[4.2.0]oct-2-ene 5-oxide (1.08 g) in methylene chloride (20 cc) is added slowly to a solution of the syn isomer of 2-(2-t-butoxycarbonylprop-2-yl)-oxyimino-2-(2-tritylaminothiazol-4-yl)-acetyl chloride (prepared from the corresponding acid and phosphorus pentachloride in accordance with the procedure described in Belgian Patent No. 876,538) (2.2 mmol) in methylene chloride (20 cc) containing triethylamine (0.6 cc), cooled to −10° C. After 45 minutes at −5° C., the reaction mixture is poured into a saturated solution of sodium bicarbonate (100 cc) and the organic phase is washed with a semi-saturated solution of sodium bicarbonate (50 cc), 0.1 N hydrochloric acid (50 cc) and a saturated solution of sodium chloride (2×50 cc). The residue obtained after drying of the organic solution and concentration to dryness under reduced pressure (30 mm Hg; 4 kPa) at 30° C. is chromatographed on a column (diameter: 2.2 cm) containing silica gel (0.2–0.06 mm) (100 cc), ethyl acetate being used as the eluent and 50 cc fractions being collected. Fractions 7 to 12 are combined and concentrated to dryness under reduced pressure (30 mm Hg; 4 kPa) at 30° C. to give the syn isomer of 2-benzhydryloxycarbonyl-7-[2-(2-t-butoxycarbonylprop-2-yl)-oxyimino-2-(2-tritylaminothiazol-4-yl)acetamido]-8-oxo-3-[2(pyridin-3-yl)-thiazol-5-yl]-5-thia-1-azabicyclo[4.2.0]oct-2-ene 5-oxide (1.7 g) in the form of a hard yellow foam.

Infra-red spectrum (KBr, characteristic bands in cm⁻¹): 1805, 1730, 1690, 1510, 1500, 1450, 1370, 1145, 760, 700.

Proton NMR spectrum (250 MHz, CDCL₃,δ in ppm, J in Hz): 1.44 (s, 9H, —C(CH₃)₃); 1.6 and 1.63 (2s, 6H,>C(CH₃)₂); 3.37 and 3.98 (2d, J=18, 2H, —S—CH₂—); 4.71 (d broad, J =5, 1H, —H in the 6-position); 6.33 (dd, J =10 and 5, 1H, —H in the 7-position); 6.73 (s, 1H, —H in the 5-position of the thiazole); 6.98 (s, 1H, —COO—CH(C₆H₅)₂) 7 to 7.5 (mt, aromatic protons and —NH—C(C₆H₅)₃); 7.4 (dd, J =8 and 5, —H in the 5-position of the pyridine); 7.61 (s, 1H, —H in the 4-position of the thiazole); 8.01 (d, J =10, 1H, —CO—NH—); 8.05 (dt, J =8 and 1.5, 1H, —H in the 4-position of the pyridine); 8.68 (dd, J =5 and 1.5, 1H, —H in the 6-position of the pyridine); 8.94 (d, J =1.5, 1H, —H in the 2-position of the pyridine).

EXAMPLE 4

A solution of the syn isomer of 2-benzhydryloxycarbonyl-7-[2-methoxyimino-2-(2-tritylaminothiazol-4-yl)acetamido]-8-oxo-3-[2(pyridin-3-yl)-thiazol-5-yl]-5-thia-1-azabicyclo[4.2.0]oct-2-ene 5-oxide (3.1 g) and t-butyl bromoacetate (0.58 cc) in N,N-dimethylformamide (15 cc) is stirred for 48 hours at 20° C. and then for 16 hours at 35° C. and poured into ethyl acetate (300 cc). The precipitate is filtered off and washed with ethyl acetate (5×20 cc) and ethyl ether (3×20 cc) to give the syn isomer of 2-benzhydryloxycarbonyl-3-[2-(1-t-butoxycarbonylmethyl-3-pyridinio)-thiazol-5-yl]7-[2-methoxyimino-2-(2-tritylaminothiazol-4-yl) -acetamido]-8-oxo-5-thia-1-azabicyclo[4.2.0]oct-2-ene 5-oxide bromide (3.2 g) in the form of a yellow solid.

Infra-red spectrum (KBr, characteristic bands in cm⁻¹): 1800, 1740, 1685, 1515, 1495, 1450, 1375, 1155, 1040, 755, 705.

Proton NMR spectrum (250 MHz, DMSO-d₆,δ in ppm, J in Hz): 1.52 (s, 9H, —C(CH₃)₃); 3.87 (s, 3H, =NOCH₃); 3. 90 and 4.41 (2d, J =19, 2H, —S—CH₂—; 5.14 (d, J =5, 1H, H in the 6-position); 5.72

(s, 2H 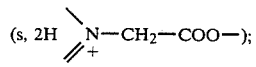

5.97 (dd, J =8 and 5, 1H, H in the 7-position); 6.82 (s, 1H, H in the 5-position of the thiazole); 6.95 (s, 1H, —COO—CH(C₆H₅)₂); 6.9 to 7.45 (mt, 25H, aromatic protons); 8.05 (s, 1H, H in the 4-position of the thiazole); 8.35 (dd, J =8.5 and 6, 1H, H in the 5-position of the pyridinio); 8.81 (s, 1H, —NH—C (C₆H₅)₃); 8.86 (d, J =8.5, 1H, H in the 4-position of the pyridinio ; 9.16 (d, J =6, 1H, H in the 6-position of the pyridinio); 9.23 (d, J =8, 1H, —CO—NH—); 9.63 (s, 1H, H in the 2-position of the pyridinio).

A solution of the syn isomer of 2-benzhydryloxycarbonyl-3-[2-(1-t-butoxycarbonylmethy-3-pyridinio)-thiazol-5-yl]-7-[2-methoxyimino-2-(2-tritylaminothiazol-4-yl)-acetamido]-8-oxo-5-thia-1-azabicyclo[4.2.-0]oct-2-ene 5-oxide bromide (3.1 g) in a mixture of methylene chloride (25 cc) and N,N-dimethylacetamide (1.06 cc) is cooled to −5° C. and treated with phosphorus trichloride (0.47 cc) and then treated in accordance with the procedure of Example 1 to give the syn isomer of 2-benzhydryloxycarbonyl-3-[2-(1-t-butoxycarbonylmethyl-3-pyridinio)thiazol-5-yl]-7-[2-methoxyimino-2-(2-tritylaminothiazol-4-yl)-acetamido]-8-oxo-5-thia-1-azabicyclo[4.2.0]oct-2-ene bromide (3 g) in the form of a yellow solid.

Infra-red spectrum (KBr, characteristic bands in cm⁻¹): 1790, 1740, 1680, 1520, 1500, 1450, 1375, 1155, 1045, 750, 705.

Proton NMR spectrum (250 MHz, DMSO-d₆,δ in ppm, J in Hz : 1.52 (s, 9H, —C(CH₃)₃); 3.91 and 4.07 (2d, J =17.5, 2H, —S—CH₂—); 3.93 (s, 3H, =N—O—CH₃); 5.34 (d, J =5, 1H, H in the 6-position); 5.75

(s, 2H, 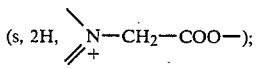

5.94 (dd, J =8 and 5, 1H, H in the 7-postion); 6.85 (s, 1H, —H in the 5-position of the thiazole); 6.93 (s, 1H, —COO—CH(C₆H₅)₂); 6.9 to 7.45 (mt, 25H, aromatic protons ; 8.09 (s, 1H, H in the 4-position of the thiazole); 8.36 (dd, J =8 and 6, 1H, H in the 5-position of the pyridinio); 8.87 (d, J =8, 1H, H in the 4-position of the pyridinio); 9.19 (d, J =6, 1H, H in the 6-position of the pyridinio); 9.63 (s, 1H, H in the 2-position of the pyridinio); 9.83 (d, J =8, 1H, —CO—NH—); 9.90 ( b, 1H, —NH—C(C₆H₅)₃).

A solution of the syn isomer of 2-benzhydryloxycarbonyl-3-[2-(1-t-butoxycarbonylmethyl-3-pyridinio)-thiazol- 5-yl]-7[2-methoxyimino-2-(2-tritylaminothiazol-4-yl)-acetamido]-8-oxo-5-thia-1-azabicyclo[4.2.-0]oct-2-ene bromide (3.1 g) in a mixture of formic acid (50 cc) and anisole (5 cc) is treated in accordance with the procedure of Example 8 to give the crude synisomer of 7-[2-(2-aminothiazol-4-yl)-2-methoxyiminoacetamido]-2-carboxylato-3-[2-(1-carboxymethyl-3-pyridinio -thiazol-5-yl]8-oxo-5-thia-1-azabicyclo[4.2.0]oct-2-ene hydrobromide (1.55 g) in the form of a yellow solid. The crude product obtained is taken up in a mixture of distilled water (200 cc) and ethyl acetate (100 cc). The insoluble material is filtered off and washed with distilled water (4×25 cc), the filtrates are combined and decanted and the aqueous phase is washed with ethyl acetate (100 cc) and then stirred with basic IR 45 resin (30 cc) until a pH of 3.8 is reached. The resin is removed by filtration and washed with distilled water (4× 10 cc). The combined filtrates are lyophilised to give the syn isomer of 7-[2-(2-aminothiazol-4-yl)-2-methoxyiminoacetamido]-2-carboxylato-3-[2-(1-carboxymethyl-3-pyridinio)-thiazol-5-yl]-8-oxo-5-thia-1-azabicyclo[4.2.0]oct-2-ene (0.85 g) in the form of an orange lyophilisate.

Infra-red spectrum (KBr, characteristic bands in cm⁻¹): 3400, 1770, 1670, 1640, 1620, 1530, 1360, 1040.

Proton NMR spectrum (250 MHz, DMSO-d₆, δ in ppm, J in Hz): 3.80 to 4 (mt, 5H, =N—O—CH₃ and —S—CH₂—); 5.24 (d, J =5 and b, 3H, H in the 6-position and

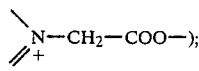
(s broad, 2H, ＞N—CH₂—COO—);

5.81 (dd, J =8 and 5, 1H, H in the 7-position); 6.77 (s, 1H, H in the 5-position of the thiazole); 7.27 ( b, 2H, —NH₂); 8.05 to 8.15 (s and mt, 2H, H in the 4-position of the thiazole and H in the 5-position of the pyridinio); 8.85 (d, J =8, 1H, H in the 4-position of the pyridinio); 8.94 ( b, 1H, H in the 6-position of the pyridinio); 9.46 (s broad, 1H H in the 2-position of the pyridinio); 9.69 (d, J =8, 1H, —CO—NH—).

EXAMPLE 5

A solution of the syn isomer of 2-benzhydryloxycarbonyl-7-[2-methoxyimino-2-(2-tritylaminothiazol-4-yl)acetamido]-8-oxo-3-[2-(pyridin-3-yl)-thiazol-5-yl]-5-thia-1-azabicyclo[4.2.0]oct-2-ene 5-oxide (3.0 g) and iodoacetamide (0.74 g) in N,N-dimethylformamide (15 cc) is stirred for 48 hours at 20° C. and then for 16 hours at 35° C. and then poured into ethyl acetate (300 cc). The precipitate is filtered off and washed with ethyl acetate (5×20 cc) and ethyl ether (3×20 cc) to give the syn isomer of 2-benzhydryloxycarbonyl-3-[2-(1-carbamoylmethyl-3-pyridinio)-thiazol-5-yl]-7-[2-methox- yimino-2-(2-tritylaminothiazol-4-yl)-acetamido]-8-oxo-5-thia-1-azabicyclo[4.2.0]oct-2-ene 5-oxide iodide (3.2 g) in the form of a yellow solid.

Infra-red spectrum (KBr, characteristic bands in cm⁻¹): 3380, 1800, 1730, 1695, 1520, 1495, 1040, 760, 705.

Proton NMR spectrum (250 MHz, DMSO-d₆, δ in ppm, J in Hz): 3.87 (s, 3H, =NOCH₃); 3.88 and 4.40 (2d, J =18, 2H, —S—CH₂—); 5.13 (d, J =4.5, 1H, H in the 6-position); 5.54

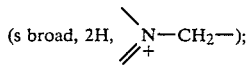
(s broad, 2H, ＞N—CH₂—);

5.97 (dd, J =8 and 4.5, 1H, H in the 7-position); 6.81 (s, 1H, H in the 5-position of the thiazole); 6.95 (s, 1H, —COO—CH(C₆H₅)₂); 6.90 to 7.4 (mt, 25N, aromatic protons); 7.80 and 8.09 (2s broad, 2H, —CO—NH₂); 8.03 (s, 1H, H in the 4-position of the thiazole); 8.28 (dd, J =7.5 and 6, 1H, H in the 5-position of the pyridinio); 8.79 (s broad, 1H, —NH—); 8.81 (d, J =7.5, 1H, H in the 4-position of the pyridiniol; 9.05 (d, J =6, 1H, H in the 6-position of the pyridinio); 9.21 (d, J =8, 1H, —CO—NH—); 9.47 (s, 1H, H in the 2-position of the pyridinio).

A solution of the syn isomer of 2-benzhydryloxycarbonyl-3- 2-(1-carbamoylmethyl-3-pyridinio)-thiazol-5-yl]-7-[2-methoxyimino-2-(2-tritylaminothiazol-4-yl)-acetamido]-8-oxo-5-thia-1-azabicyclo[4.2.0]oct-2-ene 5-oxide iodide (3.2 g) in a mixture of methylene chloride (30 cc) and N,N-dimethylacetamide (6 cc) is cooled to —5° C. and treated with phosphorus trichloride (0.5 cc) then treated in accordance with the procedure of Example 1 to give the syn isomer of 2-benzhydryloxycarbonyl-3-[2-(1-carbamoylmethyl-3-pyridinio -thiazol-5-yl ]-7-[2-methoxyimino-2-(2-tritylaminothiazol-4-yl)-acetamido]-8-oxo-5-thia-1-azabicyclo[4.2.0]oct-2-ene iodide (3.2 g) in the form of a yellow solid.

Proton NMR spectrum (250 MHz, DMSO-d₆, δ in ppm, J in Hz): 3.9 (s, 3H, =N—OCH₃); 3.90 and 4 (2d, J =18, 2H, —S—CH₂—) ; 5.33 (d, J =5, 1H, H in the 6-position); 5.61

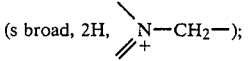
(s broad, 2H, ＞N—CH₂—);

5.94 (dd, J =8 and 5, 1H, H in the 7-position); 6.82 (s, 1H, H in the 5-position of the thiazole); 6.93 (s, 1H, —COO—CH(C₆H₅)₂); 6.9 to 7.50 (mt, 25H, aromatic protons ; 7.82 and 8.26 (2s broad, 2H, —CONH₂); 8.09 (s, 1H, H in the 4-position of the thiazole); 8.29 (mt, 1H, H in the 5-position of the pyridinio); 8.82 (d, J =8, 1H, H in the 4-position of the pyridinio); 9.10 (d, J =6, 1H, H in the 6-position of the pyridinio); 9.50 (s, 1H, H in the 2-position of the pyridinio); 9.67 ( b, 1H, —NH—); 9.82 (d, J =8, 1H, —CONH—).

A solution of the syn isomer of 2-benzhydryloxycarbonyl-3-[2-(1-carbamoylmethyl -3-pyridinio)-thiazol-5-yl]-7-[2-methoxyimino-2-(2-tritylaminothiazol-4-yl)-acetamido]-8-oxo-5-thia-1-azabicyclo[4.2.0]oct-2-ene iodide (3.3 g) in a mixture of formic acid (50 cc) and anisole (5 cc) is treated in accordance with the procedure of Example 8 to give the crude syn isomer of 7-[2-

(2-aminothiazol-4-yl)-2-methoxyiminoacetamido]-2-carboxylato-3-[2-(1-carbamoylmethyl -3-pyridinio)-thiazol-5-yl]-8-oxo-5thia-1-azabicyclo[4.2.0]oct-2-ene hydroiodide (2.35 g) in the form of an orange solid. The crude solid is taken up in a mixture of distilled water (200 cc) and ethyl acetate (100 cc). The organic phase is washed with distilled water (100 cc); the aqueous phases are decanted and combined, then washed with ethyl acetate (100 cc) and then stirred with basic IR 45 resin (30 cc) until a pH of 3 is reached. The resin is removed by filtration and washed with distilled water (4×10 cc). The combined filtrates are lyophilised to give the syn isomer of 7-[2-(2-aminothiazol-4-yl)-2-methoxyiminoacetamido]-2-carboxylato-3-[2-(1- carbamoylmethyl-3-pyridinio)-thiazol-5-yl]-8-oxo-5thia-1-azabicyclo[4.2.0]oct-2-ene (1.22 g) in the form of an orange lyophilisate.

Proton NMR spectrum (250 MHz, DMSO-$d_6$, δ in ppm, J in Hz): 3.76 and 3.89 (2d, J =18, 2H, —S—$CH_2$—); 3.88 (s, 3H, =N—O—$CH_3$); 5.18 d, J =5, 1H, H in the 6-position); 5.54

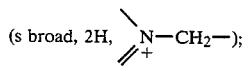
(s broad, 2H, 5.68 (dd, J =8 and 5, 1H, H in the 7-position); 6.76 (s, 1H, H in the 5-position of the thiazole); 7.25 ( b, 2H, —$NH_2$); 7.74 and 8.28 (2s broad, 2H, —CO—$NH_2$); 8.10 (s, 1H, H in the 4-position of the thiazole); 8.19 (mt, 1H, H in the 5-position of the pyridine); 8.96 (mt, 2H, H in the 4-position and H in the 6-position of the pyridine); 9.54 (s, 1H, H in the 2-position of the pyridine); 9.65 (d, J =8, 1H, —CONH—).

EXAMPLE 6

A solution of the syn isomer of 2-benzhydryloxycarbonylamino-7-[2-(2-t-butoxycarbonylprop-2-yl-oxyimino)-2-(2-tritylaminothiazol-4-yl)-acetamido]-8-oxo-3-[2-(pyridin-3-yl)-thiazol-5-yl]-5-thia-1-azabicyclo[4.2.0]oct-2-ene 5-oxide (3.3 g) in N,N-dimethylformamide (10 cc) is treated in accordance with the procedure described in Example 3, the methyl iodide being replaced by a mixture of benzyl bromide (0.475 cc) and sodium iodide (0.05 g), to give the syn isomer of 2-benzhydryloxycarbonyl-3-[2-(1-benzyl-3-pyridinio)-thiazol-5-yl]-7-[2-(2-t-butoxycarbonylprop-2-yl-oxyimino)-2-(2-tritylaminothiazol-4-yl)acetamido ]-8-oxo-5-thia-1-azabicycle[4.2.0]oct-2-ene 5-oxide bromide (3.8 g) in the form of a yellow solid.

Proton NMR spectrum (250 MHz, DMSO-$d_6$, δ in ppm, J in Hz): 1.36 (s, 9H, —C($CH_3$)$_3$); 1.45 (s, 6H, —C($CH_3$)$_2$—); 3.92 and 4.49 (2d, J =17.5, 2H —SO$CH_2$—); 5.17 (d, J =3.8, 1H, H in the 6-position); 6.0

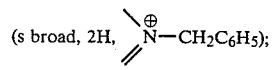
(s broad, 2H, 6.08 (dd, J =3.8 and 10, 1H, H in the 7-position); 6.66 (t, J =6, 1H, H in the para-position of the benzyl); 6.80 (s, 1H, H in the 5-position of the thiazole); 6.88 (t, J =6, 2H, H in the meta-positions of the benzyl); 6.94 (s, 1H, —$CO_2$C$\overline{H}$$Ar_2$); 7.11 (d, J =6, 2H, H in the ortho-positions of the benzyl; 7.15 to 7.75 ( b , 25H, aromatic protons ; 8.09 (s, 1H, H in the 4-position of the thiazole); 8.28 (dd, J =6 and 8.8, 1H, H in the 5-position of the pyridinio); 8.45 (d, J =8.8, 1H, H in the 4-position of the pyridinio); 8.76 (d, J =10, 1H, —CONH—); 8.78 (s, 1H, —NH— thiazole); 9.30 (d, J =6, 1H, H in the 6-position of the pyridinio); 9.68 (s, 1H, H in the 2-position of the pyridinio).

The syn isomer of 2-benzhydryloxycarbonyl-3-[2-(1benzyl-3-pyridinio)-thiazol-5-yl]-7-[2-(2-t-butoxycarbonylprop-2-yl-oxyimino)-2-(2-tritylaminothiazol-4-yl)acetamido]-8-oxo-5-thia-1-azabicyclo[4.2.-0]oct-2-ene 5-oxide bromide (3.8 g) is reduced with phosphorus trichloride (0.52 cc) in accordance with the procedure described in Example 3 to give the crude syn isomer of 2-benzhydryloxycarbonyl-3-[2-(1-benzyl-3-pyridinio -thiazol5-yl]-7-[2-(2-t-butoxycarbonylprop-2-yl-oxyimino)-2-(2-tritylaminothiazol-4-yl)-acetamido]-8-oxo-5-thia-1-azabicyclo[4.2.0]oct-2-ene bromide (3.1 g) in the form of a yellow solid.

Proton NMR spectrum (250 MHz, DMSO-$d_6$, δ in ppm, J in Hz): 1.39 (s, 9H, —C($CH_3$)$_3$); 1.46 and 1.48 (2s, 2×3H, —C($CH_3$)$_2$—); 3.9 and 4.08 (2d, J =18, 2H, —S$CH_2$—); 5.34 (d, J =5, 1H, H in the 6-position); 5.94 (dd, J =8 and 5, 1H, H in the 7-position); 6.02

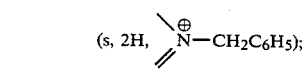
(s, 2H, 6.62 (t, J =7.5, 1H, H in the para position of the benzyl); 6.78 (s, 1H, H in the 5-position of the thiazole); 6.85 (t, J =7.5, 2H, H in the meta positions of the benzyl); 6.9 (s, 1H, $CO_2$C$\overline{H}$$Ar_2$); 7.07 (d, J =7.5, 2H, H in the ortho positions of the benzyl ; 7 to 7.75 ( b, 25H, aromatic protons ; 8.09 (s, 1H, H in the 4-position of the thiazole); 8.28 (dd, J =6 and 7.5, 1H, H in the 5-position of the pyridinio); 8.75 (d, J =7.5, 1H, H in the 4-position of the pyridinio); 9.33 (d, J =6, 1H, H in the 6-position of the pyzidinio) ; 9.59 (d, J =8, 1H, —CONH—; 9.67 (s, 1H, H in the 2-position of the pyridinio); 9.4 to 9.9 (broad signal, 1H, —NH— thiazole).

The crude syn isomer of 2-benzhydryloxycarbonyl-3 -[2-(1-benzyl-3-pyridinio)-thiazol-5-yl]-7-[2-(2-t-butoxycarbonylprop-2-yl-oxyimino)-2-(2-tritylaminothiazol-4-yl)-acetamido]-8-oxo-5-thia-1-azabicyclo[4.2.0]oct-2-ene bromide (3 g) is treated with a mixture of formic acid (30 cc) and anisole (7 cc) in accordance with the procedure described in Example 3 to give the syn isomer of 7-[2-(2-aminothiazol-4-yl)-2-(2-carboxyprop-2-yl-oxyimino)acetamido]-3-[2-(1-benzyl-3-pyridinio)-thiazol-5-yl]-2-carboxylato-8-oxo-5-thia-1-azabicyclo[4.2.0]oct-2-ene hydrobromide (1.1 g).

Proton NMR spectrum (250 MHz, DMSO-$d_6$, δ in ppm, J in Hz): 1.47 and 1.49 (2s. 2×3H, —C($CH_3$)$_2$—); 3.92 and 4.05 (2d, J =18, 2H, —S$CH_2$—); 5.33 (d, J =5, 1H, H in the 6-position); 5.98

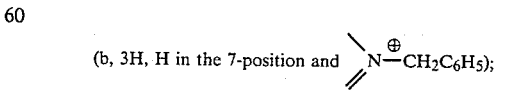
(b, 3H, H in the 7-position and 6.78 (s, 1H, H in the 5-position of the thiazole); 7.4 to 7.65 (b, 5H, aromatic protons of the benzyl +$NH_2$); 8.21 (s, 1H, H in the 4-position of the thiazole); 8.25 (dd, J =6 and 7.5, 1H, H in the 5-position of the pyridinio);

9.04 (d, J =7.5, 1H, H in the 4-position of the pyridinio); 9.21 (d, J =6, 1H, H in the 6-position of the pyridinio); 9.58 (d, J =8, 1H, —CONH—); 9.86 (s broad, 1H, H in the 2-position of the pyridinio).

EXAMPLE 7

A solution of the syn isomer of 2-benzhydryloxycarbonyl-7-[2-(2-t-butoxycarbonylprop-2-yl)-oxyimino-2-(2-tritylaminothiazol-4-yl)-acetamido]-8-oxo-3-[2-(pyridin-4-yl)-thiazol-5-yl]-5-thia-1-azabicyclo[4.2.0]oct-2-ene 5-oxide (0.95 g) in N,N-dimethylformamide (12 cc) containing methyl iodide (0.065 cc) is treated in accordance with the procedure described in Example 2 to give the syn isomer of 2-benzhydryloxycarbonyl-7-[2-(2-t-butoxycarbonylprop-2-yl)-oxyimino-2-(2-tritylaminothiazol-4-yl)acetamido]-3-[2-(1-methyl-4-pyridinio)-thiazol-5-yl]-8-oxo-5-thia-1-azabicyclo[4.2.0]oct-2-ene 5-oxide iodide (0.86 g) in the form of a yellow solid.

Infra-red spectrum (KBr, characteristic bands in cm$^{-1}$): 3400, 1800, 1730, 1685, 1640, 1520, 1495, 1450, 1370, 1145, 845, 755, 705.

Proton NMR spectrum (250 MHz, DMSO-d$_6$, δ in ppm, J in Hz): 1.37 (s, 9H, —C(CH$_3$)$_3$); 1.46 (s, 6H, >C(CH$_3$)$_2$); 3.89 and 4.5 (2d, J =18.5, 2H, —S—CH$_2$—); 4.38

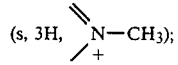

5.17 d, J =5, 1H, H in the 6-position); 6.09 (dd, J =8 and 5, 1H, H in the 7-position); 6.80 (s, 1H, H in the 5-position of the thiazole); 6.97 (s, 1H, —COO—CH(C$_6$H$_5$)$_2$); 6.95 to 7.4 (mt, 25H, aromatic protons); 8.19 (s, 1H, H in the 4-position of the thiazole); 8.33 (d, J =6, 2H, H in the 3-position and H in the 5-position of the pyridinio); 8.44 (d, J =8, 1H, —CO—NH—); 8.77 (s, 1H, —NH—C(C$_6$H$_5$)$_3$); 9.05 (d, J =6, 2H, H in the 2-position and H in the 6-position of the pyridinio).

A solution of the syn isomer of 2-benzhydryloxycarbonyl-7-[2-(2-t-butoxycarbonylprop-2-yl)-oxyimino-2-(2-tritylaminothiazol-4-yl)-acetamido]-3-[2-(1-methy-4-pyridinio)-thiazol-5-yl]-8-oxo-5-thia-1-azabicyclo[4.2.0]oct-2 -ene 5-oxide iodide (0.8g) in a mixture of methylene chloride (20 cc) and N,N-dimethylacetamide (5 cc) is treated with phosphorus trichloride (0.1 cc) in accordance with the procedure of Example 2 to give the crude syn isomer of 2-benzhydryloxy carbonyl-7-[2-(2-t-butoxycarbonylprop-2-yl)-oxyimino-2-(2-tritylaminothiazol-4-yl)-acetamido]-3-[2-(1-methyl-4-pyridinio)-thiazol-5-yl]-8-oxo-5-thia-1-azabicyclo[4.2.0]oct-2-ene (0.9 g) in the form of a yellow solid.

Infra-red spectrum (KBr, characteristic bands in cm$^{-1}$) 1790, 1730, 1685, 1640, 1520, 1495, 1450, 1370, 1145, 760, 705.

Proton NMR spectrum (250 MHz, DMSO-d$_6$, δ in ppm, J in Hz): 1.38 (s, 9H, —C(CH$_3$)$_3$); 1.43 and 1.44 (2s, 6H, >C(CH$_3$)$_2$); 3.89 and 4.09 (2d, J =18.5, 2H, —S—CH$_2$—); 4.38

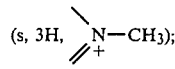

5.33 (d, J =5, 1H, H in the 6-position); 5.94 (dd, J =9 and 5, 1H, H in the 7-position); 6.74 (s, 1H, H in the 5-position of the thiazole); 6.94 (s, 1H, —COO—CH(C$_6$H$_5$)$_2$) ;6.90 to 7.4 (mt 25H, aromatic protons); 8.2 (s, 1H, H in the 4-position of the thiazole); 8.30 (d, J =6, 2H, H in the 3-position and H in the 5-position of the pyridinio); 9.05 (d, J =6 +b , 3N, H in the 2-position and H in the 6-position of the pyridinio +—NH—C(C$_6$H$_5$)$_3$); 9.58 (d, J =9, 1H, —CO—NH—).

A solution of the syn isomer of 2-benzhydryloxycarbonyl-7-[2-(2-t-butoxycarbonylprop-2-yl)-oxyimino-2-(2-tritylaminothiazol-4-yl)-acetamido]-3-[2-(1-methyl-4-pyridinio)-thiazol-5-yl]-8-oxo-5-thia-1-azabicyclo-[4.2.0]oct-2-ene (0.86 g) in formic acid (30 cc) containing anisole (2 cc) is treated in accordance with the procedure described in Example 2 to give the syn isomer of 7-[2-(2-aminothiazol-4-yl)-2-(2-carboxyprop-2-yl)-oxyiminoacetamido]-2-carboxylato-3-[2-(1-methyl-4-pyridinio)-thiazol-5-yl]-8-oxo-5-thia-1-azabicyclo[4.2.0]oct-2-ene in the form of the crude hydroiodide (0.21 g), which is treated again with basic IR 45 resin in accordance with the procedure of Example 2 to give the syn isomer of 7-[2-(2-aminothiazol-4-yl)-2-(2-carboxyprop-2-yl)-oxyiminoacetamido]-2-carboxylato-3-[2-(1-methyl-4-pyridinio)-thiazol-5-yl]-8-oxo-5-thia-1-azabicyclo[4.2.0]oct-2-ene (0.053 g) in the form of a yellow lyophilisate.

Infra-red spectrum (KBr, characteristic bands in cm$^{-1}$): 3380, 1770, 1670, 1640, 1605, 1520, 1380, 1140, 840.

Proton NMR spectrum (250 MHz, DMSO-d$_6$, δ in ppm, J in Hz): 1.4 to 1.5 ( b, >C(CH$_3$)$_2$); 3.83 ( b, 2H, —SCH$_2$—); 4.31

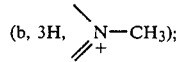

5.20 (d, J =5, 1H, H in the 6-position); 5.74 (dd, J =9 and 5, 1H, H in the 7-position); 6.73 (s, 1H, H in the 5-position of the thiazole); 7.29 ( b, 2H, —NH$_2$); 8.23 (s, 1H, H in the 4-position of the thiazole); 8.42 ( b, 2H, H in the 3-position and H in the 5-position of the pyridinio); 8.96 (b, 2H, H in the 2-position and H in the 6-position of the pyridinio); 9.48 (d, J =9, 1H, —CONH—).

The syn isomer of 2-benzhydryloxycarbonyl-7-[2-(2-t-butoxycarbonylprop-2-yl)-oxyimino-2-(2-tritylaminothiazol-4-yl)-acetamido]-8-oxo-3-[2-(pyridin-4-yl)-thiazol-5-yl]-5-thia-1-azabicyclo[4.2.0]oct-2-ene 5-oxide can be prepared in the following manner:

N-Hydroxybenzothiazole (1.015 g) and N,N'-dicyclohexylcarbodiimide (1.54 g) are added to a solution, cooled to 0° C., of the syn isomer of 2-(2-t-butoxycarbonylprop-2-yl)-oxyimino-2-(2-tritylaminothiazol-4-yl)-acetic acid (4.3 g) and 7-amino-2-benzhydryloxycarbonyl-8-oxo-3-[2-(pyridin-4-yl)-thiazol-5-yl]-5-thia-1-azabicyclo[4.2.0]oct-2-ene 5-oxide (2.7 g) in N,N-dimethylformamide (50 cc). The reaction mixture is stirred for 1 hour at 0° C. and then for 16 hours at 25° C. The precipitate is removed by filtration and washed with ethyl acetate (2×30 cc). The combined filtrates are diluted with ethyl acetate (1 liter) and washed with water (500 cc) containing a saturated solution of sodium bicarbonate (50 cc) and then with distilled water (2×500 cc) and with a saturated solution of sodium chloride (200 cc). After drying over magnesium sulphate and evaporation of the solvent to dryness under reduced pressure (30 mm Hg; 4 kPa) at 40° C., the residue is subjected to chromatography on a column (height =30 cm, diameter =5 cm) of silica gel (0.04–0.06 mm), elution being carried out with ethyl acetate under a pressure of 0.5 bar and 100 cc fractions being collected. Fractions 7 to 12 are combined and concentrated under reduced pressure (30 mm Hg; 4 kPa) at 30° C. to give the impure expected product 2 g), which is chromatographed again on a column (height =30 cm, diameter =40 cm) of silica gel (0.04–0.06 mm), elution being carried out under a pressure of 0.5 bar with a mixture of cyclohexane and ethyl acetate (10/90 by volume) and 100 cc fractions being collected. Fractions 5 to 16 are combined and concentrated to dryness under reduced pressure (30 mm Hg; 4 kPa) at 30° C. to give the syn isomer of 2-benzhydryloxycarbonyl-7-[2-(2-t-butoxycarbonylprop-2-yl)-oxyimino-2-(2-tritylaminothiazol-4-yl)-acetamido]-8-oxo-3-[2-(pyridin-4-yl)-thiazol-5-yl]-5-thia-1-azabicyclo[4.2.0]oct-2-ene 5-oxide (1.05 g) in the form of a hard beige foam.

Infra-red spectrum (KBr, characteristic bands in $cm^{-1}$): 3400, 1805, 1730, 1685, 1595, 1510, 1495, 1450, 1370, 1220, 1145, 820, 755, 700.

Proton NMR spectrum (250 MHz, $CDCL_3$, δ in ppm, J in Hz): 1.44 (s, 9H,—C(CH$_3$)$_3$); 1.59 and 1.62 (2s, 6H, >C(CH$_3$)$_2$); 3.37 and 3.96 (dd, J =18.5 and 1, and d, J =18.5, 2H, —S—CH$_2$—); 4.7 (dd, J =5 and 1, 1H, H in the 6-position); 6.31 (dd, J =10 and 5, 1H, H in the 7-position); 6.72 (s, 1H, H in the 5-position of the thiazole); 6.96 (s, 1H, —COO—CH(C$_6$H$_5$)$_2$); 6.95 to 7.4 (mt, aromatic protons); 7.59 dd, J =5 and 1, 2H, H in the 3-position and H in the 5-position of the pyridine); 7.63 (s, 1H, H in the 4-position of the thiazole); 7.97 (d, J =10, 1H, —CONH—); 8.71 dd, J =5 and 1, H in the 2-position and H in the 6-position of the pyridine).

The 7-amino-2-benzhydryloxycarbonyl-8-oxo-3-[2-(pyridin-4-yl)-thiazol-5-yl]-5-thia-1-azabicyclo[4.2.0]oct-2-ene 5-oxide can be prepared in the following manner:

2-Benzhydryloxycarbonyl-7-t-butoxycarbonylamino-8-oxo-3-[2-(pyridin-4-yl)-thiazol-5-yl]-5-thia-1-azabicyclo[4.2.0]oct-2-ene 5-oxide (6.4 g) is treated with methanesulphonic acid (6 cc) in acetonitrile (60 cc) in accordance with the procedure of Example 2 to give 7-amino-2-benzhydryloxycarbonyl-8-oxo-3-[2-(pyridin-4-yl)thiazol-5-yl]-5-thia-1-azabicyclo[4.2.0]oct-2-ene 5-oxide (2.7 g) in the form of a hard brown foam.

Rf =0.14 (silica gel chromatography plate, eluent: ethyl acetate/methanol, 85/15 by volume).

The 2-benzhydryloxycarbonyl-7-t-butoxycarbonylamino-8-oxo-3-[2-(pyridin-4-yl)-thiazol-5-yl]-5-thia-1-azabicyclo[4.2.0]oct-2-ene 5-oxide can be prepared in the following manner:

A solution of 2-benzhydryloxycarbonyl-7-t-butoxycarbonylamino-8-oxo-3-[2-(pyridin-4-yl)-thiazol-5-yl]-5-thia-1-azabicyclo[4.2.0]oct-2-ene (24 g) in methylene chloride (370 cc) is oxidised with 85% pure meta-chloroperbenzoic acid (7.92 g) in accordance with the procedure described in Example 2 to give 2-benzhydryloxycarbonyl-7-t-butoxycarbonylamino-8-oxo-3-[2-(pyridin-4-yl)-thiazol-5-yl]-5-thia-1-azabicyclo[4.2.0]oct-2-ene 5-oxide (23 g) in the form of a brown-yellow solid.

Infra-red spectrum $CHBr_3$, characteristic bands in $cm^{-1}$): 3410, 1800, 1715, 1595, 1505, 1370, 1240, 1050, 820, 745.

Proton NMR spectrum (250 MHz, $CDCL_3$, δ in ppm, J in Hz): 1.5 (s, 9H, —C(CH$_3$)$_3$); 3.38 and 4.04 (dd, J =18.5 and 1, and d, J =18.5, 2H, —S—CH$_2$—); 4.61 (dd, J =5 and 1, 1H, H in the 6-position); 5.8 (d, J =10, 1H, —CONH—); 5.95 (dd, J =10 and 5, 1H, H in the 7-position); 6.94 ( s, 1H, —COO—CH(C$_6$H$_5$)$_2$); 6.95 to 7.4 (mt, aromatic protons); 7.60 (dd, J =5 and 1, 2H, H in the 3-position and H in the 5-position of the pyridine); 7.65 (s, 1H, H in the 4-position of the thiazole); 8.70 (dd, J =5 and 1, 2H, H in the 2-position and H in the 6-position of the pyridine).

The 2-benzhydryloxycarbonyl-7-t-butoxycarbonylamino-8-oxo-3-[2-(pyridin-4-yl)-thiazol-5-yl]-5-thia-1-azabicyclo[4.2.0]oct-2-ene can be prepared in the following manner:

A solution of 2-benzhydryloxycarbonyl-3-(1-bromo-2-oxoethyl)-7-t-butoxycarbonylamino-8-oxo-5-thia-1-azabicyclo[4.2.0]oct-2-ene (mixture of the diastereoisomers) (94 g) in tetrahydrofuran (250 cc) is added in the course of 1 hour 40 minutes to a solution, at 40° C., of thioisonicotinamide (44 g) in N,N-dimethylacetamide (330 cc). The reaction mixture is stirred for 90 minutes at 40°–45° C. and then cooled to −15° C. and treated with methanesulphonyl chloride (18.5 cc) and then triethylamine (53 cc). The mixture is stirred for 1 hour at about −10° C. and then for 16 hours at 25° C. and then diluted with ethyl acetate (1.5 liters) and distilled water (1 liter). The organic phase is washed successively with 0.2 N hydrochloric acid (1.2 liters) and water (2×1 liter), then with a mixture of water (500 cc) and a saturated solution of sodium bicarbonate (150 cc) and finally with water (2×1 liter) and a saturated solution of sodium chloride (200 cc). The residue obtained after evaporation of the solvent to dryness under reduced pressure (30 mm Hg, 4 kPa) at 40° C. is chromatographed on a column (height =56 cm, diameter =80 cm) containing silica gel (0.2–0.06 mm), elution being carried out with a mixture of cyclohexane and ethyl acetate (50/50 by volume) and 800 cc fractions being collected. Fractions 8 to 12 are combined and concentrated to dryness under reduced pressure (30 mm Hg; 4 kPa) at 30° C. to give 2-benzhydryloxycarbonyl-7-t-butoxycarbonylamino-8-oxo-3-[2-(pyridin-4-yl)-thiazol-5-yl]-5-thia-1-azabicyclo[4.2.0]oct-2-ene (24 g) in the form of a hard brown foam.

Rf =0.47 (silica gel chromatography plate, eluent: ethyl acetate).

EXAMPLE 8

A solution of the syn isomer of 2-benzhydryloxycarbonyl-7-[2-methoxyimino-2-(2-tritylaminothiazol-4-yl)acetamido]-8-oxo-3-[2-(pyridin-4-yl)-thiazol-5-yl]-5-thia-1-azabicyclo[4.2.0]oct-2-ene 5-oxide (1.6 g) and methyl iodide. (0.12 cc) in N,N-dimethylformamide (16 cc) is stirred for 70 hours at 20° C. and then run into ethyl acetate (250 cc). The precipitate is filtered off and washed with ethyl acetate (2×20 cc) and ethyl ether (3×20 cc) and then dried to give the syn isomer of 2-benzhydryloxycarbonyl-7-[2-methoxyimino-2-(2-tritylaminothiazol-4-yl)-acetamido]-3-[2-(1-methyl-4-pyridinio)-thiazol-5-yl]-8-oxo-5-thia-1-azabicyclo[4.2.-

0]oct-2-ene 5-oxide iodide (1.4 g) in the form of a yellow powder.

Infra-red spectrum (KBr, characteristic bands in cm$^{-1}$) 1800, 1730, 1670, 1640, 1525, 1500, 1450, 1220, 1040, 760, 705.

Proton NMR spectrum (250 MHz, DMSO-d$_6$, δ in ppm, J in Hz : 3.85 (s, 3H, =NOCH$_3$); 3.94 and 4.45 (2d, J=15, —S—CH$_2$—);

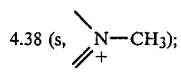
4.38 (s, 5.14 (d, J =4.5, 1H, H in the 6-position); 5.99 (dd, J =7 and 4.5, 1H, H in the 7-position); 6.83 (s, 1H, H in the 5-position of the thiazole); 6.96 (s, 1H, —COO—CH(C$_6$H$_5$)$_2$); 7 to 7.5 (mt, aromatic protons); 8.15 (s, 1H, H in the 4-position of the thiazole); 8.33 (d, J =6, 2H, H in the 3-position and H in the 5-position of the pyridinio); 8.83 (s, 1H, —NH—C(C$_6$H$_5$)$_3$); 9.05 (d, J =6, 2H, H in the 2-position and H in the 6-position of the pyridinio); 9.3 (d, J =7, 1H, —CO—NH—).

A solution of the syn isomer of 2-benzhydryloxy carbonyl-7-[2-methoxyimino-2-(2-tritylaminothiazol-4-yl)acetamido]-3-[2-(1-methyl-4-pyridinio)-thiazol-5-yl]-8-oxo-5-thia-1-azabicyclo[4.2.0]oct-2-ene 5-oxide iodide (1.3 g) in a mixture of methylene chloride (40 cc) and N,N-dimethylacetamide (10 cc), cooled to −5° C., is treated with phosphorus trichloride (0.17 cc) and then stirred at −5° C. for 40 minutes and poured into ethyl acetate (200 cc). The precipitate is filtered off, washed with ethyl acetate (3×10 cc) and ethyl ether (3×20 cc) and then taken up in methylene chloride (10 cc) and methanol (2 cc). The solution is filtered on a sintered filter packed with silica gel (0.06–0.2 mm) (5 cc) and the filtrate is then concentrated to dryness under reduced pressure (30 mm Hg; 4 kPa) at 30° C. to give the crude syn isomer of 2-benzhydryloxycarbonyl-7-[2-methoxyimino-2-(2-tritylaminothiazol-4-yl)-acetamido]-3-[2-(1-methyl-4-pyridinio)-thiazol-5-yl]-8-oxo-5-thia-1-azabicyclo[4.2.0]oct-2-ene iodide (1.14 g) in the form of a yellow solid.

Proton NMR spectrum (250 MHz, DMSO-d$_6$, δ in ppm, J in Hz): 3.87 (s, 3H, =N—OCH$_3$); 3.96 (d, J =19, 1H of the —S—CH$_2$—), from 4 to 4.20 (the other H of the —S—CH$_2$—); 4.38

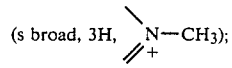
(s, 3H, 5.32 (d, J =5, 1H, H in the 6-position; 5.92 (dd, J =8 and 5, 1H, H in the 7-position); 6.78 (s, 1H, H in the 5-position of the thiazole); 6.92 (s, 1H, —COO—CH(C$_6$H$_5$)$_2$); 6.95 to 7.45 (mt, aromatic protons); 8.15 (s, 1H, H in the 4-position of the thiazole); 8.30 (d, J =6, 2H, H in the 3-position and H in the 5-position of the pyridinio); 9.05 (d, J =6, 2H, H in the 2-position and H in the 6-position of the pyridinio); 9.25 ( b, 1H, —NH—C(C$_6$H$_5$)$_3$); 9.76 (d, J =8, 1H, —CO—NH—).

A solution of the syn isomer of 2-benzhydryloxyc arbonyl-7-[2-methoxyimino-2-(2-tritylaminothiazol-4-yl)-acetamido]-3-[2-(1-methyl-4-pyridinio)-thiazol-5-yl]-8-oxo-5-thia-1-azabicyclo[4.2.0]oct-2-ene iodide (6.2 g) in a mixture of anisole (25 cc) and formic acid (30 cc) is heated for 30 minutes at 50° C. and then concentrated to dryness under reduced pressure (1 mm Hg; 0.13 kPa) at 40° C. The residue is taken up in ethanol (100 cc), which is evaporated off to dryness under reduced pressure (30 mm Hg; 4 kPa) at 40° C., this operation being repeated a further 2 times. The residue is solidified with ethanol (150 cc). The solid is filtered off, washed with ethanol (2×10 cc) and ethyl ether (3×20 cc) and dried. This gives the crude syn isomer of 7-[2-(2-aminothiazol-4-yl)-2-methoxyiminoacetamido]-2-carboxylato-3-[2-(1-methyl-4-pyridinio)thiazol-5-yl]-8-oxo-5-thia-1-azabicyclo[4.2.0]oct-2-ene hydroiodide (3.72 g) in the form of a light brown solid, which is taken up in distilled water (400 cc); after filtration, the aqueous phase is washed with ethyl acetate (2×50 cc) and treated with basic IR 45 resin until a pH of 4.8 is reached. The resin is removed by filtration and the aqueous solution is lyophilised to give the syn isomer of 7-[2-(2-aminothiazol-4-yl)-2-methoxyiminoacetamido]-2-carboxylato-3- 2-(1-methyl-4-pyridinio)thiazol-5-yl]-8-oxo-5-thia-1-azabicyclo[4.2.0]oct-2-ene (1.22 g) in the form of an orange lyophilisate.

Infra-red spectrum (KBr, characteristic bands in cm$^{-1}$): 3390, 1770, 1670, 1640, 1610, 1525, 1380, 1035.

Proton NMR spectrum (250 MHz, DMSO-d$_6$, δ in ppm, J in Hz): 3.78 and 3.88 (2d, J =18, 2H, —S—CH$_2$—); 3.86 (s, 3H, =N—O—CH$_3$); 4.30

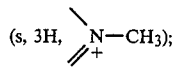
(s broad, 3H, 5.19 (d, J =5, 1H, H in the 6 position); 5.69 (dd, J =8 and 5, 1H, H in the 7-position); 6.76 (s, 1H, H in the 5-position of the thiazole); 7.25 (s broad, 2H, —NH$_2$); 8.23 (s, 1H, H in the 4-position of the thiazole); 8.41 (d, J =5.5, 2H, H in the 3-position and H in the 5-position of the pyridinio); 8.95 (d, J =5.5, 2H, H in the 2-position and H in the 6-position of the pyridinio); 9.65 (d, J =8, 1H, —CO—NH—); 14 to 10 ( b very broadened, 1H, —COOH).

The 2-benzhydryloxycarbonyl-7-[2-methoxyimino-2-(2-tritylaminothiazol-4-yl)-acetamido]-8-oxo-3-[2-(pyridin-4-yl)-thiazol-5-yl]-5-thia-1-azabicyclo[4.2.0]oct-2-ene 5-oxide can be prepared in the following manner:

The syn isomer of 2-methoxyimino-2-(2-tritylaminothiazol-4-yl)-acetic acid (12.4 g) and 4-N,N-dimethylaminopyridine (0.05 g) are added to a solution of 7-amino-2-benzhydryloxycarbonyl-8-oxo-3-[2-(pyridin-4-yl)-thiazol-5-yl]-5-thia-1-azabicyclo[4.2.0]oct-2-ene 5-oxide (15 g) in dry methylene chloride (100 cc), and a solution of N,N′-dicyclohexylcarbodiimide (6.93 g) in methylene chloride (120 cc) is then added (in the course of 30 minutes) after cooling to +5° C. The reaction mixture is then stirred for 1 hour at +5° C. and then for 4 hours at 25° C., after which it is partially concentrated, diluted again with ethyl acetate (500 cc) and filtered. The filtrate is poured into a mixture of distilled water (1 liter), ethyl acetate (1 liter) and acetic acid (10 cc). The organic phase is washed with a saturated solution of sodium bicarbonate (200 cc), distilled water (3×200 cc) and then a saturated solution of sodium chloride (200 cc), dried over sodium sulphate and then concentrated to dryness under reduced pressure (30 mm Hg; 4 kPa) at 40° C. to give the crude expected product (26.8 g) in the form of a hard brown foam, which can be purified in the following manner: the crude product (5 g) is redissolved in ethanol (120 cc) under reflux, decolorising charcoal (0.5 g) and silica (0.5 g) are added, the mixture is stirred and filtered and the filtrate is cooled in a bath of iced water. The precipitate is filtered off and washed with ethanol (2×10 cc) and then ether (2×20 cc) to give 2-benzhydryloxycarbonyl-7-[2-methoxyimino-2-(2-tritylaminothiazol-4-yl)acetamido]-8-oxo-3-[2-(pyridin-4-yl)-thiazol-5-yl]-5-thia1-azabicyclo[4.2.0]oct-2-ene 5-oxide (2 g) in the form of an ochre powder.

Infra-red spectrum (KBr, characteristic bands in cm$^{-1}$): 3390, 1805, 1690, 1605, 1515, 1500, 1450, 1220, 1050, 1040, 830, 760, 700.

Proton NMR spectrum (250 MHz, DMSO-d$_6$, δ in ppm, J in Hz): 3.8 to 3.90 ( b, 1H of the —S—CH$_2$—); 3.85 (s, =N—OCH$_3$); 4.41 (d, J =18.5, 1H of the —S—CH$_2$—); 5.1 (d, J=4.5, H in the 6-position); 5.95 (mt, H in the 7-position); 6.83 (s, H in the 5-position of the thiazole); 6.96 (s, —COO—C$\underline{H}$(C$_6$H$_5$)$_2$); 7.60 to 7.7 (mt, H in the 3-position and H in the 5-position of the pyridine); 7.96 (s, H in the 4-position of the thiazole); 8.72 (mt, H in the 2-position and H in the 6-position of the pyridine); 8.82 (b, —N$\underline{H}$—C(C$_6$H$_5$)$_3$); 9.25 (D, J=8, —CON$\underline{H}$—).

EXAMPLE 9

A solution of the syn isomer of 2-benzhydryloxycarbonyl-7-[2-methoxyimino-2-(2-tritylaminothiazol-4-yl)acetamido]-8-oxo-3-[2-(pyridin-3-yl-methyl)-thiazol-5-yl]-5-thia-1-azabicyclo[4.2.0]oct-2-ene 5-oxide (3.47 g) and methyl iodide (0.435 cc) in N,N-dimethylformamide (20 cc) is stirred at 40° C. for 2 hours. The mixture is poured into ethyl ether (200 cc) and then stirred vigorously for 15 minutes. The precipitate obtained is filtered off, washed with ethyl ether (2×20 cc) and then dried under reduced pressure (0.1 mm Hg; 0.013 kPa). This gives the syn isomer of 2-benzhydryloxycarbonyl-7-[2-methoxyimiro-2-(2-tritylaminothiazol-4-yl)-acetamido]-8-oxo-3-[2-(1-methyl-3-pyridinio-methyl)-thiazol-5-yl]-5-thia-1-azabicyclo[4.2.0]oct-2-ene 5-oxide iodide (3.9 g) in the form of a cream powder.

Infra-red spectrum (KBr, characteristic bands in cm$^{-1}$): 1795, 1730, 1665, 1570, 1450, 1220, 1040, 755, 700, 675.

Proton NMR spectrum (350 MHz, DMSO-d$_6$, δ in ppm, J in Hz): 3.80 and 4.25 (2d, J=18, 2H, —S—CH$_2$—); 3.85 (s, 3H, =N—OCH$_3$); 4.35

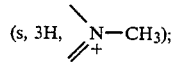
(s, 3H, \N—CH$_3$);
  //+

4.47 (s, 2H, —CH$_2$—); 5.09 (d, J=4, 1H, H in the 6-position); 5.92 (dd, J=7.5 and 4, 1H, H in the 7-position); 6.82 (s, 1H, H in the 5-Position of the thiazole); 6.91 (s, 1H, —COO—C$\underline{H}$—(C$_6$H$_5$)$_2$); 7.15 to 7.45 (mt, aromatic protons); 7.62 (s, 1H, H in the 4-position of the thiazole); 8.12 (dd, J=8 and 6, 1H, H in the 5-position of pyridinio); 8.48 (d, J=8, 1H, H in the 4-position of the pyridinio); 8.8 (s, 1H, —NH—C(C$_6$H$_5$)$_3$); 8.93 (d, J=6, 1H, H in the 6-position of the pyridinio); 9.03 (s, 1H, H in the 2-position of the pyridinio); 9.17 (d, J=7.5, 1H, —CO—NH—).

Phosphorus trichloride (0.612 cc) is added dropwise, in the course of 5 minutes, to a solution, cooled to −2° C., of the syn isomer of 2-benzhydryloxycarbonyl-7-[2-methoxyimino-2-(tritylaminothiazol-4-yl)-acetamido]-8-oxo-3-[2-(1-methyl-3-pyridinio-methyl)-thiazol-5-yl]-5-thia-1-azabicyclo[4.2.0]oct-2-ene 5-oxide iodide (3.9 g) and N,N-dimethylacetamide (1.39 cc) in methylene chloride (35 cc). The mixture is stirred at 0° C. for 25 minutes and the reaction mixture is then diluted with ethyl acetate (200 cc). The resulting mixture is stirred for 15 minutes and the precipitate obtained is filtered off and washed with ethyl acetate (4×50 cc) and then with ethyl ether (2×50 cc). The powder is dried under reduced pressure (0.1 mm Hg; 0.013 kPa) to give the syn isomer of 2-benzhydryloxycarbonyl-7-[2-methoxyimino-2-(2-tritylaminothiazol- 4-yl)-acetamido]-8-oxo-3-[2-(1-methyl-3-pyridinio -methyl)-thiazol-5-yl]-5-thia-1-azabicyclo[4.2.0]-oct-2-ene iodide (3.8 g) in the form of a yellow solid.

Infra-red spectrum (KBr, characteristic bands in cm$^{-1}$): 1785, 1730, 1680, 1510, 1450, 1220, 1040, 755, 700.

A mixture of trifluoroacetic acid (17 cc) and distilled water (1.7 cc) is run into a solution, cooled to +4° C., of the syn isomer of 2-benzhydryloxycarbonyl-7-[2-methoxyimino-2-(2-tritylaminothiazol-4-yl)-acetamido]-8-oxo-3-[2-(1-methyl-3-pyridinio-methyl)-thiazol-5-yl]-5-thia-1-azabicyclo[4.2.0]oct-2-ene iodide (3.8 g) in anisole (3.8 cc). Distilled water (3.8 cc) is then run into the stirred mixture kept at 4° C. The cooling bath is removed and the mixture is stirred for 30 minutes at 20° C. Ethyl ether (400 cc) is then added and the liquid phase is decanted. The oily residue is taken up in acetone (200 cc); a solid precipitates. The precipitate is filtered off and washed with acetone (3×20 cc). This gives the syn isomer of 7-[2-(2-aminothiazol-4-yl)-2-methoxyiminoacetamido]-2-carboxy-3-[2-(1-methyl-3-pyridinio-methyl)-thiazol-5-yl]-8-oxo-5-thia-1-azabicyclo[4.2.0]oct-2-ene iodide (2.11 g) in the form of a yellow powder.

Infra-red spectrum (KBr, characteristic bands in cm$^{-1}$): 3490, 3050, 1780, 1670, 1630, 1365, 1200, 1180, 1045, 985, 680, 600.

Proton NMR spectrum (250 MHz, DMSO-d$_6$, δ in ppm, J in Hz): 3.88 (s, —S—CH$_2$—); 3.96 (s, =N—OCH$_3$);

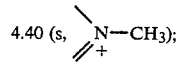
4.40 (s, \N—CH$_3$;
         //+

4.65 (s, —CH$_2$—); 5.29 (d, J=5, 1H, H in the 6-position); 5.87 (dd, J=9 and 5, H in the 7-position); 6.95 (s, 1H, H in the 5-position of the thiazole); 7.8 (s, 1H, H in the 4-position of the thiazole); 6.90 to 7.70 (b, —NH$_2$); 8.16 (mt, H in the 5-position of the pyridinio); 8.59 (d, J=7.5, H in the 4-position of the pyridinio); 9.01 (b, 1H, H in the 6-position of the pyridinio); 9.18 (s broad, 1H, H in the 2-position of the pyridino); 9.92 (d, J=9, 1H, —CONH—).

A solution of the syn isomer of 7-[2-(2-aminothiazol-4-yl)-2-methoxyiminoacetamido]-2-carboxy-3-[2-(1-methyl-3-pyridinio-methyl)-thiazol-5-yl]-8-oxo-5-thia-1-azabicyclo[4.2.0]oct-2-ene iodide (1.35 g) in distilled water (60 cc) is washed with ethyl acetate (2×10 cc). The aqueous phase is decanted and concentrated to a residual volume of 50 cc under reduced pressure (30 mm Hg; 4 kPa). The residue is filtered and basic Amberlite IR 45 resin (28 cc) is added to the solution. The change in the acidity of the mixture is followed with a pH meter. The resin is filtered off at pH 4.4 and the filtrate is lyophilised. This gives the syn isomer of 7-[2-(2-aminothiazol-4-yl)-2-methoxyiminoacetamido]-2-carboxylato-3-[2-(1-methyl-3-pyridinio-methyl)-thiazol-5-yl]-8-oxo-5-thia-1-azabicyclo[4.2.0]oct-2-ene (0.65 g) in the form of a brown-yellow lyophilisate.

Infra-red spectrum (KBr, characteristic bands in cm$^{-1}$): 3500, 3000, 1770, 1670, 1610, 1385, 1335, 1040, 680.

Proton NMR spectrum (250 MHz, DMSO-d$_6$, δ in ppm, J in Hz): 3.63 and 3.75 (2d, J=17.5, —S—CH$_2$—); 3.86 (s, =N—OCH$_3$); 4.38

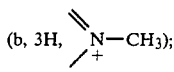
(b, 3H, $\overset{\diagdown}{\underset{\diagup^+}{N}}$—CH$_3$);

4.55 (b, 2H, —CH$_2$—); 5.11 (d, J=4, 1H, H in the 6-position); 5.63 (dd, J=8 and 4, 1H, H in the 7-position); 6.75, (s, 1H, H in the 5-position of the thiazole); 7.25 (s broad, —NH$_2$); 7.74 (s, 1H, H in the 4-position of the thiazole); 8.1 (b, 1H, H in the 5-position of the pyridinio); 8.55 (b, 1H, H in the 4-position of the pyridinio); 8.95 (b, 1H, H in the 6-position of the pyridinio); 9.14 (b, 1H, H in the 2-position of the pyridinio); 9.59 (d, J=8, 1H, —CONH—).

The syn isomer of 2-benzhydryloxycarbonyl-7-[2-methoxyimino-2-(2-tritylaminothiazol-4-yl)-acetamido]-8-oxo-3-[2-(pyridin-3-yl-methyl)-thiazol-5-yl]-5-thia-1-azabicyclo[4.2.0]oct-2-ene 5-oxide can be prepared in the following manner:

A solution of m-chloroperbenzoic acid (1.46 g) in methylene chloride (30 cc) is added dropwise, in the course of 15 minutes, to a solution, cooled to 3° C., of the syn isomer of 2-benzhydryloxycarbonyl-7-[2-methoxyimino-2-(2-tritylaminothiazol-4-yl)-acetamido]-8-oxo-3-[2-(pyridin-3-yl-methyl)-thiazol-5-yl]-5-thia-1-azabicyclo[4.2.0]oct-2-ene (8.30 g) in methylene chloride (85 cc). The mixture is stirred at 3° C. for 4 hours 30 minutes and then diluted with methylene chloride (100 cc). The organic phase is washed successively with a semi-saturated solution of sodium bicarbonate (150 cc), distilled water (100 cc) and then a saturated solution of sodium chloride (100 cc). It is then dried over anhydrous sodium sulphate; the mixture is filtered and the filtrate is concentrated to dryness under reduced pressure (30 mm Hg; 4 kPa) at 30° C. The residue is purified by chromatography on a column (height=30 cm, diameter=2.5 cm) containing silica gel (0.05-0.2 mm), elution being carried out with ethyl acetate (1.2 liters) and then with a mixture of ethyl acetate and methanol (95/5 by volume) (0.8 liter) and 60 cc fractions being collected. Fractions 19 to 33, containing the pure product, are combined and concentrated under reduced pressure (30 mm Hg; 4 kPa) at 30° C. to give the syn isomer of 2-benzhydryloxycarbonyl-7-[2-methoxyimino-2-(2-tritylaminothiazol-4-yl)-acetamido]-8-oxo-3-[2-(pyridin-3-yl-methyl)-thiazol-5-yl]-5-thia-1-azabicyclo[4.2.0]oct-2-ene 5-oxide (5 g) in the form of a hard yellow foam.

Infra-red spectrum (CHCl$_3$, characteristic bands in cm$^{-1}$): 3400, 1805, 1730, 1685, 1515, 1450, 1375, 1050.

Proton NMR spectrum (250 MHz, CDCl$_3$, δ in ppm, J in Hz): 3.27 and 3.85 (2d, J=18, 2H, —S—CH$_2$—); 4 to 4.2 (mt, 5H, =N—O—CH$_3$ and —CH$_2$—); 4.57 (d, J=5, 1H, H in the 6-position); 6.18 (dd, J=10 and 5, 1H, H in the 7-position); 6.71 (s, 1H, H in the 5-position of the thiazole); 6.88 (s, 1H, —COO—CH(C$_6$H$_5$)$_2$); 7.15 (b, —NH—C(C$_6$H$_5$)$_3$); 7.25 (mt, H in the 5-position of the pyridine); 7.05 to 7.35 (mt, aromatic protons); 7.4 (s, 1H, H in the 4-position of the thiazole); 7.52 (ddd, J=7.5-2 and 1.5, 1H, H in the 4-position of the pyridine); 7 62 (d, J=10, —CONH—); 8.48 (s broad, 1H, H in the 2-position of the pyridine); 8.50 (dd, J=5 and 1.5, 1H, H in the 6-position of the pyridine).

The syn isomer of 2-benzhydryloxycarbonyl-7-[2-methoxyimino-2-(2-tritylaminothiazol-4-yl)-acetamido]-8-oxo-3-[2-(pyridin-3-yl-methyl)-thiazol-5-yl]-5-thia-1-azabicyclo[4.2.0]oct-2-ene can be prepared in the following manner:

The syn isomer of 2-methoxyimino-2-(2-tritylaminothiazol-4-yl)-acetic acid (5.32 g), 3-hydroxybenzotriazole (1.62 g) and N,N-dicyclohexylcarbodiimide (2.47 g) are added to a solution, cooled to +5° C., of 7-amino-2-benzhydryloxycarbonyl-8-oxo-3-[2-(pyridin-3-yl-methyl)-thiazol-5-yl]-5-thia-1-azabicyclo[4.2.0]oct-2-ene (5.4 g) in N,N-dimethylformamide (100 cc). The mixture is stirred for 1 hour at 5° C., the temperature is then allowed to rise and the mixture is stirred for 4 hours at 23° C. Acetic acid (0.5 cc) is added, the mixture is stirred for 5 minutes and the suspension is filtered. The filtrate is poured into a 50/50 (by volume) mixture of water and ethyl acetate (500 cc). The organic phase is decanted and then washed successively with a 0.1 N solution of hydrochloric acid (100 cc), a saturated solution of sodium bicarbonate (100 cc), distilled water (100 cc) and a saturated solution of sodium chloride (100 cc). It is dried over anhydrous sodium sulphate and filtered and the filtrate is concentrated to dryness under reduced pressure (20 mm Hg; 2.7 kPa) at 30° C. The residue is purified by chromatography on silica gel (0.05-0.2 mm) (height of silica: 77 cm, diameter of the column: 3.5 cm), elution being carried out with a 20/80 (by volume) mixture of cyclohexane and ethyl acetate (1 liter) and then with a 10/90 (by volume) mixture of cyclohexane and ethyl acetate (3.8 liters) and 60 cc fractions being collected. Fractions 39 to 80 are combined and concentrated to dryness under reduced pressure (20 mm Hg; 2.7 kPa). This gives the syn isomer of 2-benzhydryloxycarbonyl-7-[2-methoxyimino-2-(2-tritylaminothiazol-4-yl)-acetamido]-8-oxo-3-[2-(pyridin-3-yl-methyl)thiazol-5-yl]-5-thia-1-azabicyclo[4.2.0]oct-2-ene (5.43 g) in the form of a hard yellow foam.

Infra-red spectrum (CHBr$_3$, characteristic bands in cm$^{-1}$): 3390, 1785, 1725, 1680, 1510, 1445, 1220, 1040, 750.

Proton NMR spectrum (250 MHz, CDCl$_3$, δ in ppm, J in Hz): 3.45 and 3.65 (2d, J≃18, 2H, —S—CH$_2$—); 4.05 (limiting AB spectrum, 2H, —CH$_2$—); 4.11 (s, 3H, =N—O—CH$_3$); 5.11 (d, J≃5, 1H, H in the 6-position); 6 (dd, J≃9 and 5, 1H, H in the 7-position; 6.72 (s, 1H, H in the 5-position of the thiazole); 6.90 (s, 1H, —COO—CH—(C$_6$H$_5$)$_2$); 7 to 7.35 (mt, aromatic protons, H in the 5-position of the pyridine, —CONH—, —NH—); 7.38 (s, 1H, H in the 4-position of the thiazole); 7.52 (d broad, J≃8, H in the 4-position of the pyridine); 8.50 (mt, 1H, H in the 2-position of the pyridine); 8.51 (dd, J≃5 and 1, 1H, H in the 6-position of the pyridine).

The 7-amino-2-benzhydryloxycarbonyl-8-oxo-3-[2-(pyridin-3-yl-methyl)-thiazol-5-yl]-5-thia-1-azabicyclo-[4.2.0]oct-2-ene can be prepared in the following manner:

A solution of methanesulphonic acid (10 cc) is added to a solution of 2-benzhydryloxycarbonyl-7-t-butoxycarbonylamino-8-oxo-3-[2-(pyridin-3-yl-methyl)-thiazol-5-yl]-5-thia-1-azabicyclo[4.2.0]oct-2-ene (10 g) in acetonitrile (100 cc). The mixture is stirred for 5 minutes and poured into a 50/50 (by volume) mixture of a saturated solution of sodium bicarbonate and ethyl acetate (500 cc). The organic phase is decanted and then washed successively with distilled water (200 cc) and then a saturated solution of sodium chloride (200 cc). It is dried over anhydrous magnesium sulphate and filtered and the filtrate is concentrated to dryness under reduced pressure (30 mm Hg; 4 kPa) at 30° C. This gives 7-amino-2-benzhydryloxycarbonyl-8-oxo-3-[2-(pyridin-3-yl-methyl)thiazol-5-yl]-5-thia-1-azabicyclo[4.2.0]oct-2-ene (6.36 g) in the form of a hard brown foam.

Infra-red spectrum (CHBr$_3$), characteristic bands in (cm$^{-1}$): 3400, 3340, 1780, 1725, 1620, 1495, 1480, 1450, 1425, 1220, 760.

Proton NMR spectrum (250 MHz, DMSO-d$_6$, δ in ppm, J in Hz): 3.72 and 3.83 (2d, J=18, 2H, —S—CH$_2$—); 4.13 and 4.23 (2d, J=16, 2H, —CH$_2$—); 4.89 (d, J=5, 1H, H in the 7-position); 5.08 (d, J=5, 1H, H in the 6-position); 6.8 (s, 1H, —COO—CH(C$_6$H$_5$)$_2$); 7.05 to 7.4 (mt, aromatic protons, —NH$_2$ and H in the 5-position of the pyridine); 7.53 (s, 1H, H of the thiazole); 7.64 (ddd, J=8 - 2.5 and 1, 1H, H in the 4-position of the pyridine); 8.47 (dd, J=5 and 1, 1H, H in the 6-position of the pyridine); 8.49 (d, J=2, 1H, H in the 2-position of the pyridine).

The 2-benzhydryloxycarbonyl-7-t-butoxycarbonylamino-8-oxo-3-[2-(pyridin-3-yl-methyl)-thiazol-5-yl]-5-thia-1-azabicyclo[4.2.0]oct-2-ene can be prepared in the following manner:

A solution of 2-benzhydryloxycarbonyl-3-(1-bromo-2-oxoethyl)-7-t-butoxycarbonylamino-8-oxo-5-thia-1-azabicyclo[4.2.0]oct-2-ene (mixture of the epimeric bromoaldehydes) (88.1 g) in anhydrous tetrahydrofuran (150 cc) is added to a solution of pyridin-3-yl-thioformamide (25 g) in N,N-dimethylacetamide (200 cc). The mixture is stirred for 6 hours at 20° C. and then run into a 50/50 (by volume) mixture of water and ethyl acetate (2 liters). The organic phase is decanted and then washed successively with a saturated solution of sodium bicarbonate (500 cc), water (250 cc) and a saturated solution of sodium chloride (250 cc). It is dried over anhydrous magnesium sulphate and filtered and the filtrate is concentrated to dryness under reduced pressure (30 mm Hg; 4 kPa). The residue is purified by chromatography on a column (height: 60 cm, diameter: 6 cm) containing silica gel (0.05–0.2 mm), elution being carried out with ethyl acetate (7 liters) and 120 cc fractions being collected. The contents of fractions 18 to 56 are concentrated to dryness under reduced pressure (30 mm Hg; 4 kPa) at 30° C. to give 2-benzhydryloxycarbonyl-7-t-butoxycarbonylamino-8-oxo-3-[2-(pyridin-3-yl-methyl)-thiazol-5-yl]-5-thia-1-azabicyclo[4.2.0]oct-2ene (26.74 g) in the form of a hard cream foam.

Infra-red spectrum (CHBr$_3$), characteristic bands in (cm$^{-1}$): 3420, 1785, 1720, 1500, 1455, 1425, 1390, 1240, 760.

Proton NMR spectrum (250 MHz, CDCl$_3$, δ in ppm, J in Hz): 1.47 (s, 9H, —C(CH$_3$)$_3$); 3.48 and 3.67 (2d, J=18, 2H, —S—CH$_2$—); 4.1 (limiting AB spectrum, J=16, 2H, —CH$_2$—); 5.04 (d, J=5, 1H, H in the 6-position); 5.41

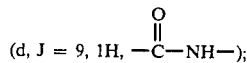

(d, J = 9, 1H, —C—NH—);

5.71 (dd, J=5 and 9, 1H, H in the 7-position); 6.9 (s, 1H, —COO—CH(C$_6$H$_5$)$_2$); 7.05 to 7.4 (mt, aromatic protons and H in the 5-position of the pyridine); 7.39 (s, 1H, H of the thiazole); 7.53 (ddd, J=8-2.5 and 1, 1H, H in the 4-position of the pyridine); 8.50 (d, J=2.5, 1H, H in the 2-position of the pyridine); 8.53 (dd, J=5 and 1, 1H, H in the 6-position of the pyridine).

The pyridin-3-yl-thioacetamide can be prepared in the following manner:

A stream of hydrogen sulphide is bubbled for 6 hours into a solution of pyridin-3-yl-acetonitrile (50 g) and triethylamine (54 cc) in absolute ethanol (500 cc). The mixture is left to stand for 48 hours and a stream of nitrogen is then passed in. The mixture is concentrated to dryness under reduced pressure (30 mm Hg; 4 kPa) and the residual oil is taken up in ethanol (150 cc). The mixture is heated under reflux and filtered and crystallisation takes place on cooling. The crystals are filtered off, washed with ethanol (10 cc) and then dried under reduced pressure (0.1 mm Hg; 0.013 kPa). This gives pyridin-3-yl-thioacetamide (52 g) in the form of a white crystalline powder.

M.p. inst. 135°–136° C. (Kofler).

Proton NMR spectrum (60 MHz, DMSO-d$_6$, δ in ppm, J in Hz): 3.9 (s, 2H, —CH$_2$—); 7.38 (q, J=8 and 5, 1H, H in the 5-position); 7.75 (dd, J=8 and 2, 1H, H in the 4-position); 8.50 (dd, J=5 and 2, 1H, H in the 6-position); 8.60 (d, J=2, 1H, H in the 2-position); 9.50 (s broad, 2H, —NH$_2$—).

EXAMPLE 10

A solution of the syn isomer of 2-benzhydryloxycarbonyl-7-[2-methoxyimino-2-(2-tritylaminothiazol-4-yl)acetamido]-3-[2-(pyridin-3-yl-amino)-thiazol-5-yl]-8-oxo-5-thia-1-azabicyclo[4.2.0]oct-2-ene (13.06 g) and methyl iodide (2.11 g) in N,N-dimethylformamide (135 cc) is stirred for 24 hours at 23° C. The reaction mixture is diluted with isopropyl ether (270 cc) and ethyl ether (540 cc). The supernatant liquor is decanted and the oily residue is taken up in ethyl ether (500 cc). The product precipitates. The precipitate is filtered off and dried under reduced pressure (0.1 mm Hg; 0.013 kPa) at 20° C. This gives the syn isomer of 2-benzhydryloxycarbonyl-7-[2-methoxyimino-2-(2-tritylaminothiazol-4-yl)acetamido]-3-[2-(1-methyl-3-pyridino-amino)-thiazol-5-yl]-8-oxo-5-thia-1-azabicyclo[4.2.0]oct-2-ene iodide (11.55 g) in the form of a yellow powder.

Infra-red spectrum (KBr); characteristic bands (cm$^{-1}$): 3120, 2500, 1785, 1730, 1665, 1600, 1530, 1505, 1450, 1035, 755, 700, 670.

Proton NMR spectrum (350 MHz, DMSO d$_6$, δ in ppm J in Hz): 3.85 (limiting AB spectrum, J=18, 2H, —S—CH$_2$—); 3 87 (s, 3H, =N—OCH$_3$); 4.42

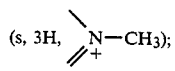

(s, 3H, N—CH$_3$);

5.28 (d, J=5, 1H, H in the 6-position); 5.84 (dd, J=9 and 5, 1H, H in the 7-position); 6.76 (s, 1H, H in the 5-position of the thiazole); 6.92 (s, 1H, —COOCH(C$_6$H$_5$)$_2$); 7 to 7.5 (mt, aromatic protons and H in the 4-position of the thiazole); 8.06 (dd, J=9 and 6, 1H, H in the 5-position of the pyrioinio); 8.43 (d broad, J=9, 1H, H in the 4-position of the pyridinio); 8.62 (d, J=6, 1H, H in the 6-position of the pyridinio); 8.85 (s, 1H, —NH—C(C$_6$H$_5$)$_3$); 9.2 (s broad, 1H, H in the 2-position of the pyridinio); 9.67 (d, J=9, 1H, —CO—NH—); 11.30 (s, 1H, —NH—).

Trifluoroacetic acid (4.6 cc) and distilled water (0.46 cc) are added to a solution, cooled to 5° C., of the syn isomer of 2-benzhydryloxycarbonyl-7-[2-methoxyimino-2-(2-tritylaminothiazol-4-yl)-acetamido]-3-[2-(1-methyl-3-pyridinio-amino)-thiazol-5-yl]-8-oxo-5-thia-1-azabicyclo[4,2,0]oct-2-ene iodide (0.78 g) in anisole (0.7 cc). The mixture is stirred at 5° C. for 5 minutes and then at 23° C. for 1.hour 15 minutes. The solution is diluted successively with acetone (3 cc) and ether (20 cc). The heterogeneous mixture is stirred for 15 minutes and then filtered and the precipitate which is collected is dried under reduced pressure (0.1 mm Hg; 0.013 kPa). This gives the syn isomer of 7-[2-(2-aminothiazol-4-yl)-2-methoxyiminoacetamido]-2-carboxy-3-[2-(1-methyl-3-pyridinioamino)-thiazol-5-yl]-8-oxo-5-thia-1-azabicyclo[4.2.0]oct-2-ene ditrifluoroacetate (0.51 g) in the form of a yellowochre powder.

Infra-red spectrum (KBr), characteristic bands in (cm$^{-1}$): 3400, 2200, 1775, 1675, 1530, 1510, 1200, 1140, 1050, 800, 725, 670.

Proton NMR spectrum (350 MHz, DMSO d$_6$, δ in ppm, J in Hz): 3.83 and 3.93 (2d, J=18 2H, —S—CH$_2$—); 3.92 (s, 3H, =NOCH$_3$); 4.38

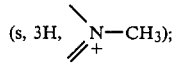
(s, 3H, N—CH$_3$);

5.27 (d, J=5, 1H, H in the 6-position); 5.87 (dd, J=8 and 5, 1H, H in the 7-position); 6.83 (s, 1H, H in the 5-position of the thiazole); 7.52 (s, 1H, H in the 4-position of the thiazole); 8.02 (dd, J=8.5 and 5, 1H, H in the 5-position of the pyridinio); 8.47 (d, J=8.5, 1H, H in the 4-position of the pyridinio); 8.57 (d, J=5, 1H, H in the 6-position of the pyridino); 8.5 to 5 (b, very broadened, —NH$_2$ and —COOH); 9.39 (s, 1H, H in the 2-position of the pyridine); 9.76 (d, J=8, 1H, —CO—NH—); 11.6 (b, 1H, —NH—).

A solution of Amberlite LA-2 resin (0.9 cc) in methyl isobutyl ketone (2.6 cc) is added to a suspension of the syn isomer of 7-[2-(2-aminothiazol-4-yl)-2-methoxyiminoacetamido]-2-carboxy-3-[2-(1-methyl-3-pyridinioamino)-thiazol-5-yl]-8-oxo-5-thia-1-azabicyclo[4.2.0]oct-2ene ditrifluoroacetate (0.35 g) in distilled water (7 cc). The change in the acidity of the mixture is followed with a pH meter. At neutrality (pH=6.8), the suspension is filtered and the precipitate obtained is washed successively with methyl isobutyl ketone (2×2 cc), distilled water (2×2 cc), ethanol (3×2 cc), acetone (3×2 cc) and ethyl ether (3×10 cc). The solid is dried under reduced pressure (0.1 mm Hg; 0.013 kPa) to give the syn isomer of 7-[2-(2-aminothiazol-4-yl)-2-methoxyiminoacetamido]-2-carboxylato-3-[2-(1-methyl-3-pyridinio-amino)-thiazol-5-yl]-8-oxo-5-thia-1-azabicyclo-[4.2.0]oct-2-ene (0.2 g) in the form of a yellow powder.

Infra-red spectrum (KBr; characteristic bands in cm$^{-1}$): 3500, 2000, 1760, 1670, 1530, 1030, 670.

Proton NMR spectrum (250 MHz, DMSO d$_6$+1 drop of CF$_3$COOD, δ in ppm, J in Hz): 3.83 and 3.93 (2d, J=18, 2H, —S—CH$_2$—); 3.94 (s, 3H, =N—OCH$_3$); 4.37

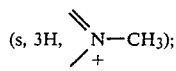
(s, 3H, N—CH$_3$);

5.27 (d, J=5, 1H, H in the 6-position); 5.87 (dd, J=8 and 5, 1H, H in the 7-position); 6.91 (s, 1H, H in the 5-position of the thiazole); 7.53 (s, 1H, H in the 4-position of the thiazole); 8.02 (dd, J=6 and 8, 1H, H in the 5-position of the pyridinio); 8.47 (d broad, J=8, 1H, H in the 4-position of the pyridino); 8.57 (d, J=6, 1H, H in the 6-position of the pyridinio); 9.38 (s broad, 1H, H in the 2-position of the pyridinio); 9.82 (d, J=8, 1H, —CO—NH—).

The syn isomer of 2-benzhydryloxycarbonyl-7-[2-methoxyimino-2-(2-tritylaminothiazol-4-yl)-acetamido]-3-[2-(pyridin-3-yl-amino)-thiazol-5-yl]-8-oxo-5-thia-1-azabicyclo[4.2.0]oct-2-ene can be prepared in the following manner:

1-Hydroxybenzothiazole (3.24 g) and N,N'-dicyclohexylcarbodiimide (4.95 g) are added to a solution, cooled to 5° C., of 7-amino-2-benzhydryloxycarbonyl-3-[2-(pyridin-3-yl-amino)-thiazol-5-yl]-8-oxo-5-thia-1-azabicyclo-[4.2.0]oct-2-ene (10.83 g) and the syn isomer of 2-methoxyimino-2-(2-tritylaminothiazol-4-yl)-acetic acid (10.65 g) in dry N,N-dimethylformamide (200 cc). The mixture is stirred for 30 minutes at +5° C. and then for 4 hours at 20° C. Acetic acid (1 cc) is added to the reaction mixture and the precipitate is then filtered off. The filtrate is diluted with ethyl acetate (900 cc) and the organic phase is washed successively with distilled water (2×500 cc), a decinormal solution of hydrochloric acid (500 cc), a semi-saturated solution of sodium bicarbonate (500 cc), distilled water (2×500 cc) and a semi-saturated solution of sodium chloride (500 cc). After the organic phase has been dried over magnesium sulphate and filtered and the filtrate concentrated under reduced pressure (30 mm Hg; 4 kPa), a hard yellow foam is obtained which is purified by chromatography on a column (height 61 cm, diameter 4.8 cm) containing silica gel (0.06–0.20 mm), elution being carried out with a 25/75 (by volume) mixture of cyclohexane and ethyl acetate (2 liters) and ethyl acetate (500 cc) and 250 cc fractions being collected. Fractions 5 to 14 are combined and concentrated to dryness under reduced pressure (30 mm Hg; 4 kPa) at 30° C. This gives the syn isomer of 2-benzhydryloxycarbonyl-7-[2-methoxyimino-2-(2-tritylaminothiazol-4-yl)-acetamido]-3-[2-pyridin-3-yl-amino)-thiazol-5-yl]-8-oxo-5-thia-1-azabicyclo[4.2.0]oct-2-ene (14.6 g) in the form of a hard, bright yellow foam.

Infra-red spectrum (KBr, characteristic bands in cm$^{-1}$): 3380,3180,1785, 1730, 1680,1530, 1490, 1040, 755, 700.

Proton NMR spectrum (350 MHz, DMSO d$_6$, δ in ppm, J in Hz): 3.84 (limiting AB spectrum, J=18, 2H, —S—CH$_2$—); 3.85 (s, 3H, =N—OCH$_3$); 5.26 (d, J=5, 1H, H in the 6-position); 5.81 (dd, J=8 and 5, 1H, H in the 7-position); 6.76 (s, 1H, H in the 5-position of the thiazole); 6.89 (s, 1H, —COO—CH(C$_6$H$_5$)$_2$); 7 to 7.50 (mt, aromatic protons, H in the 4-position of the thiazole and H in the 5-position of the pyridine); 8.07 (ddd, J=8, 2 and 1.5, 1H, H in the 4-position of the pyridine); 8.19 (dd, J=6 and 1.5, 1H, H in the 6-position of the pyridine); 8.70 (d, J=2, 1H, H in the 2-position of the pyridine); 8.85 (s, 1H, —NH—C(C<sub>6</sub>H<sub>5</sub>)<sub>3</sub>); 9.68 (d, J=8, 1H, —CONH—); 10.46 (s broad, 1H, —NH—).

The 7-amino-2-benzhydryloxycarbonyl-3-[2-(pyridin-3-yl-amino)-thiazol-5-yl]-8-oxo-5-thia-1-azabicyclo-[4.2.0]oct-2-ene can be prepared in the following manner:

Methanesulphonic acid (37.7 cc) is added in the course of 5 minutes to a solution of 2-benzhydryloxycarbonyl-7-t-butoxycarbonylamino-3-[2-(pyridin-3-yl-amino)thiazol-5-yl]-8-oxo-5-thia-1-azabicyclo[4.2.0]oct-2-ene (37.22 g) in acetonitrile (372 cc). The mixture is stirred for 5 minutes and the reaction solution is then added to a mixture of a saturated solution of sodium bicarbonate (870 cc), distilled water (1,740 cc) and methylene chloride (580 cc). The mixture is stirred for 10 minutes and the precipitate is filtered off and washed with distilled water (4×100 cc). The product is dried to give 7-amino-2-benzhydryloxycarbonyl-3-[2-(pyridin-3-yl-amino)thiazol-5-yl]-8-oxo-5-thia-1-azabicyclo-[4.2.0]oct-2-ene (27.66 g) in the form of a pale yellow crystalline powder.

Infra-red spectrum (KBr, characteristic bands in cm$^{-1}$): 3380, 3150, 2000, 1780, 1730, 1670, 1590, 1550, 1530, 1490, 1225, 800, 760, 750, 700.

Proton NMR spectrum (250 MHz, DMSO d<sub>6</sub>, δ in ppm, J in Hz): 2.4 (b, 2H, —NH<sub>2</sub>); 3.78 (limiting AB spectrum, J=18, 2H, —S—CH<sub>2</sub>—); 4.88 (d broad, J=5, 1H, H in the 7-position); 5.1 (d, J=5, 1H, —H in the 6-position); 6.85 (s, 1H, —COO—CH(C<sub>6</sub>H<sub>5</sub>)<sub>2</sub>); 7 to 7.35 (mt, 11H, aromatic protons and —H of the thiazole); 7.34 (mt, 1H, —H in the 5-position of the pyridine); 8.06 (ddd, J=8-2.5 and 1, 1H, —H in the 4-position of the pyridine); 8.17 (dd, J=5 and 1, 1H, —H in the 6-position of the pyridine); 8.68 (d, J=2.5, 1H, —H in the 2-position of the pyridine); 10.38 (b, 1H, —NH—).

The 2-benzhydryloxycarbonyl-7-t-butoxycarbonylamino-3-[2-(pyridin-3-yl-amino)-thiazol-5-yl]-8-oxo-5-thia-1-azabicyclo[4.2.0]oct-2-ene can be prepared in the following manner:

A solution of bromine (35.96 g) in dry methylene chloride (40 cc) is added dropwise to a solution, cooled to −75° C. of the E form of 2-benzhydryloxycarbonyl-7-t-butoxycarbonylamino-3-(2-dimethylaminovinyl)-8-oxo-5-thia-1-azabicyclo[4.2.0]oct-2-ene (107.1 g) in dry tetrahydrofuran (600 cc). The mixture is stirred at this temperature for 10 minutes and a solution of pyridin-3-yl-thiourea (30.64 g) in a mixture of water and tetrahydrofuran (50/50 by volume) (400 cc) is then added. The cooling bath is removed and the mixture is stirred at 20° C. for 17 hours. The brown solution is diluted with ethyl acetate (1.5 liters) and then washed successively with distilled water (1 liter), a semi-saturated solution of sodium bicarbonate (1 Liter), distilled water (1 liter) and a saturated solution of sodium chloride (500 cc). The organic phase is dried over anhydrous magnesium sulphate. After evaporation of the solvent under reduced pressure (30 mm Hg; 4 kPa) at 30° C., the residue is chromatographed on a column (height: 46 cm, diameter: 8.1 cm) containing silica gel (0.06–0.20 mm), elution being carried out successively with a mixture of cyclohexane and ethyl acetate (50/50 by volume) (5 liters), a mixture of cyclohexane and ethyl acetate (25/75 by volume) (5 liters) and ethyl acetate (7 liters) and 1 liter fractions being collected. Fractions 8 to 17, containing the pure product, are combined and concentrated to a residual volume of 250 cc. This gives a yellow suspension, which is kept at 5° C. for 12 hours. The solid is filtered off, washed with ethyl ether (3×100 cc) and dried under reduced pressure (1 mm Hg; 0.13 kPa). This gives 2-benzhydryloxycarbonyl-7-t-butoxycarbonylamino-3-[2-(pyridin-3-yl-amino)-thiazol-5-yl]-8-oxo-5-thia-1-azabicyclo[4.2.0]oct-2-ene (14.5 g) in the form of a yellow powder.

Infra-red spectrum (KBr, characteristic bands in cm$^{-1}$): 3330, 3100, 2500, 1790, 1720, 1590, 1530, 1500, 1370, 1160, 760, 745, 705.

Proton NMR spectrum (250 MHz, DMSO d<sub>6</sub>, δ in ppm, J in Hz): 1.45 (s, 9H, —C(CH<sub>3</sub>)<sub>3</sub>); 3.76 and 3.88 (2d, J=18, 2H, —S—CH<sub>2</sub>—); 5.18 (d, J=5, 1H, —H in the 6-position); 5.59 (dd, J=9 and 5, 1H, —H in the 7-position); 6.88 (s, 1H, —COO—CH(C<sub>6</sub>H<sub>5</sub>)<sub>2</sub>); 7 to 7.4 (mt, 11H, aromatic protons and —H of the thiazole); 7.34 (mt, 1H, —H in the 5-position of the pyridine); 8.07 (ddd, J=8–2.5 and 1, 1H, —H in the 4-position of the pyridine); 8.11 (d, J=9, 1H, —CONH—); 8.19 (dd, J=5 and 1, 1H, —H in the 6-position of the pyridine); 8.69 (d, J=2, 1H, —H in the 2-position of the pyridine); 10.45 (s, 1H, =N—H).

EXAMPLE 11

A solution of the syn isomer of 2-benzhydryloxycarbonyl-7-{2-[(2-t-butoxycarbonylprop-2-yl)-oxyimino]-2-(2-tritylaminothiazol-4-yl)-acetamido}-8-oxo-3-[2-(pyridin-3-yl-amino)-thiazol-5-yl]-5-thia-1-azabicyclo[4.2.0]oct-2-ene 5-oxide (1.67 g) and methyl iodide (0.10 cc) in N,N-dimethylformamide (15 cc) is stirred for 24 hours. The mixture is diluted by adding isopropyl ether (30 cc). The supernatant liquors are decanted and the residue is stirred with ethyl ether (50 cc). The precipitate is filtered off and dried under reduced pressure (0.1 mm Hg; 0.013 kPa) at 20° C. This gives the syn isomer of 2-benzhydryloxycarbonyl-7-{2-[(2-t-butoxycarbonylprop-2-yl)-oxyimino]-2-(2-tritylaminothiazol-4-yl)-acetamido}-3-[2-(1-methyl-3-pyridinioamino)-thiazol-5-yl]-8-oxo-5-thia-1-azabicyclo[4.2.-0]oct-2-ene 5-oxide iodide (1.53 g).

Infra-red spectrum (CHBr<sub>3</sub>, characteristic bands in cm$^{-1}$): 3380, 3100, 2500, 1806, 1730, 1675, 1600, 1505, 1450, 1370, 1145, 755, 700, 675.

Proton NMR spectrum (250 MHz, DMSO d<sub>6</sub>, δ in ppm, J in Hz): 1.36 (s, 9H, —C(CH<sub>3</sub>)<sub>3</sub>); 1.44 and 1.45 (2s, 6H, >C(CH<sub>3</sub>)<sub>2</sub>); 3.83 and 4.37 (2d, J=18.5, 2H, —SCH<sub>2</sub>—);

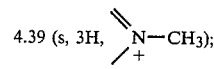

4.39 (s, 3H, >N—CH<sub>3</sub>);

5.12 (d, J=5, 1H, —H in the 6-position); 6.08 (dd, J=9 and 5, 1H, —H in the 7-position); 6.80 (s, 1H, —H in the 5-position of the thiazole); 6.95 (s, 1H, —COO—CH(C<sub>6</sub>H<sub>5</sub>)<sub>2</sub>); 7 to 7.4 (mt, aromatic protons and —H in the 4-position of the thiazole); 8.05 (dd, J=8 and 6, 1H, —H in the 5-position of the pyridine); 8.35 (d, J=9, 1H, —CO—NH—); 8.41 (d broad, J=8, 1H, —H in the 4-position of the pyridine); 8.6 (d, J=6, 1H, —H in the 6-position of the pyridine); 8.78 (s, 1H, —NHC(C<sub>6</sub>H<sub>5</sub>)<sub>3</sub>); 9.19 (s broad, 1H, —H in the 2-position of the pyridine); 11.33 (b, 1H, >NH).

Trifluoroacetic acid (6.5 cc) and distilled water (0.65 cc) are added to a solution, cooled to 5° C., of the syn isomer of 2-benzhydryloxycarbonyl-7-{2-[(2-t-butoxycarbonylprop-2-yl)-oxyimino]-2-(2-tritylaminothiazol-4-yl)acetamido}-3-[2-(1-methyl-3-pyridinio-amino)-thiazol-5-yl]-8-oxo-5-thia-1-azabicyclo[4.2.0]oct-2-ene 5-oxide (1.25 g) in anisole (1 cc). This mixture is stirred for 10 minutes at this temperature and then for 1 hour 15 minutes at 22° C. The reaction mixture is then diluted with acetone (4.3 cc) and then ethyl ether (40 cc). It is stirred for 5 minutes and filtered and the precipitate is washed with ethyl ether (5×10 cc). This gives the syn isomer of 7-{2-(2-aminothiazol-4-yl)-2-[(2-carboxyprop-2-yl)-oxyimino]-acetamido}-2-carboxy-3-[2-(1- methyl-3-pyridinio-amino)-thiazol-5-yl]-8-oxo-5-thia-1-azabicyclo[4.2.0]oct-2-ene 5-oxide ditrifluoroacetate (0.78 g) in the form of a greenish-brown powder.

Infra-red spectrum (KBr, characteristic bands in cm$^{-1}$): 3700, 2200, 1790, 1675, 1635, 1525, 1510, 1200, 1145, 800, 720, 670.

Proton NMR spectrum (250 MHz, DMSO d$_6$, δ in ppm, J in Hz): 1.51 and 1.52 (2s, 6H, >C(CH$_3$)$_2$); 3.8 and 4.41 (2d, J=18.5, 2H, —S—CH$_2$—); 4.36

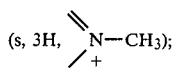

(s, 3H, N—CH$_3$);

5.11 (d, J=5, 1H, —H in the 6-position); 6.08 (dd, J=8 and 5, 1H, —H in the 7-position); 6.86 (s, 1H, —H in the 5-position of the thiazole); 7.10 to 7.8 (b, 3H, —NH$_3$); 7.54 (s, 1H, —H in the 4-position of the thiazole); 8.01 (dd, J=8.5 and 5, 1H, —H in the 5-position of the pyridino); 8.44 (d broad, J=8.5, 1H, —H in the 4-position of the pyridinio); 8.56 (d, J=5, 1H, —H in the 6-position of the pyridinio); 8.63 (d, J=8, 1H, —CONH—); 9.35 (s broad, 1H, —H in the 2-position of the pyridine); 11.6 (b, 1H >N—H); 14 to 11 (b broadened, —COOH).

A solution of Amberlite LA-2 resin (1.75 cc) in methyl isobutyl ketone (5.35 cc) is added to a suspension of the syn isomer of 7-{2-(2-aminothiazol-4-yl)-2-[(2-carboxyprop-2-yl)-oxyimino]-acetamido}-2-carboxy-3-[2-(1-methyl-3-pyridinio-amino)-thiazol-5-yl]-8-oxo-5-thia-1-azabicyclo[4.2.0]oct-2-ene 5-oxide ditrifluoroacetate (0.71 g) in distilled water (21.3 cc). The mixture is stirred until the pH reaches 6.2, the liquid phase is then filtered and the filtrate is lyophilised. The lyophilisate is stirred for 2 hours in anhydrous ether (25 cc), filtered off, washed with ether (2×10 cc) and dried under reduced pressure (0.1 mm Hg; 0.013 kPa) to give the syn isomer of 7-{2-(2-aminothiazol-4-yl)-2-[(2-carboxyprop-2-yl)-oxyimino]-acetamido}-2-carboxylato-3-[2-(1-methyl-3-pyridinio-amino)-thiazol-5-yl]-8-oxo-5-thia-1-azabicyclo[4.2.0]oct-2-ene 5-oxide (0.12 g) in the form of a yellow powder.

Infra-red spectrum (KBr, characteristic bands in cm$^{-1}$): 1780, 1670, 1610, 1530, 1395, 1040, 675.

Proton NMR spectrum (250 MHz, DMSO d$_6$, δ in ppm, J in Hz): about 1.51 ppm (b, >C(CH$_3$)$_2$); 3.78 and 4.25 (2d, J=18.5, 2H, —S—CH$_2$—); 4.31

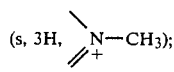

(s, 3H, N—CH$_3$);

5.05 (d, J=4, 1H, —H in the 6-position); 5.9 (b, 1H, —H in the 7-position); 6.81 (s, 1H, —H in the 5-position of the thiazole); 7.23 (b, 2H, —NH$_2$); 7.49 (s, 1H, —H in the 4-position of the thiazole); 7.87 (b, 1H, —H in the 5position of the pyrdinio); 8.42 (b, 1H, —H in the 6-position of the pyridinio); 9.05 (b, 1H, H in the 4-position of the pyridinio); 5.20 (b, 1H, —H in the 2-position of the pyridinio).

The syn isomer of 2-benzhydryloxycarbonyl--7-{2-[(2-t-butoxycarbonylprop-2-yl)-oxyimino]-2-(2-tritylaminothiazol-4-yl)-acetamido}-8-oxo-3-[2-(pyridin-3-yl-amino)thiazol-5-yl]-5-thia-1-azabicyclo[4.2.0]oct-2-ene 5-oxide can be prepared in the following manner:

A solution of m-chloroperbenzoic acid (2.59 g) in methylene chloride (52 cc) is run, in the course of 30 minutes, into a solution, cooled to 0° C., of the syn isomer of 2-benzhydryloxycarbonyl-7-{2-[(2-t-butoxycarbonylprop-2-yl)-oxyimino]-2-(2-tritylaminothiazol-4-yl)acetamido}-8-oxo-3-[2-(pyridin-3-yl-amino)-thiazol-5-yl]-5-thia-1-azabicyclo[4.2.0]oct-2-ene (13.46 g) in methylene chloride (123 cc). The mixture is stirred for 15 minutes at 0° C. and the reaction solution is then diluted with methylene chloride (200 cc). The mixture is washed successively with a semi-saturated solution of sodium bicarbonate (200 cc) and distilled water (2×200 cc). The organic phase is then dried over anhydrous magnesium sulphate and filtered and the filtrate is then concentrated under reduced pressure (100 mm Hg; 13.3 kPa) at 30° C. The residue is purified by chromatography on a column (height=29 cm, diameter=5.8 cm) containing silica gel (0.04–0.06 mm), elution being carried out under a pressure of 0.4 bar with a mixture of cyclohexane and ethyl acetate (10/90 by volume) (2 liters) and 125 cc fractions being collected. Fractions 11 to 15 are combined and concentrated to dryness under reduced pressure (30 mm Hg; 4 kPa) at 30° C. to give the syn isomer of 2-benzhydryloxycarbonyl--7-{2-[(2-t-butoxycarbonylprop-2-yl)-oxyimino]-2-(2-tritylaminothiazol-4-yl)-acetamido}-8-oxo-3-[2-(pyridin-3-yl-amino)-thiazol-5-yl]-5-thia-1-azabicyclo[4.2.0]oct-2-ene 5-oxide (0.70 g) in the form of a hard yellow foam.

Infra-red spectrum (CHBr$_3$, characteristic bands in cm$^-$): 3390, 1800, 1725, 1680, 1530, 1495, 1450, 370, 1050, 700.

Proton NMR spectrum (250 MHz, CDCl$_3$, δ in ppm, J in Hz): 1.41 (s, 9H, —C(CH$_3$)$_3$); 1.56 and 1.58 (2s, 6H, >C(CH$_3$)$_2$); 3.25 and 3.84 (2d, J=18.5, 2H, —S—CH$_2$—); 4.56 d, J =5, 1H, —H in the 6-position); 6.19 (dd, J=9.5 and 5, 1H, —H in the 7-position); 6.72 (s, 1H, —H in the 5-position of the thiazole); 6.92 (s, 1H, —COO—CH—(C$_6$H$_5$)$_2$); 7.01 (s, 1H, —H in the 4-position of the thiazole); 7.11 (dd , J=5 and 7.5, —H in the 5-position of the pyridine); 7.05 to 7.45 (mt, aromatic protons); 7.9 (ddd, J =7.5, 2 and 1.5, 1H, —H in the 4-position of the pyridine); 8.0 (d, J =9.5, 1H, —CONH—); 8.21 (dd, J =5 and 1.5, 1H, —H in the 6-position of the pyridine); 8.6 (d, J=2, 1H, —H in the 2-position of the pyridine); 8.73 b, 1H, —NHC(C$_6$H$_5$)$_3$).

The syn isomer of 2-benzhydryloxycarbonyl-7-{2-[2-t-butoxycarbonylprop-2-yl-oxyimino]-2-(2-tritylamino-thiazol-4-yl)-acetamido }-8-oxo-3-[2-(pyridin-3-yl-amino)-thiazol-5-yl]-5-thia-1-azabicyclo[4.2.0]oct-2-ene can be prepared in the following manner:

1-Hydroxybenzotriazole (3.24 g) and N,N'-dicyclohexylcarbodiimide (4.95 g) are added to a solution, cooled to +5° C., of 7-amino-2-benzhydryloxycarbonyl-8-oxo-3-[2-(pyridin-3-yl-amino)-thiazol-5-yl]-5-thia-1-azabicyclo[ 4.2.0]oct-2-ene (10.83 g) and the syn isomer of 2-(2-tritylaminothiazol-4-yl)-2-[(2-t-butoxycarbonylprop-2-yl)-oxyimino]-acetic acid (13.72 g) in anhydrous N,N-dimethylformamide (200 cc). The mixture is stirred for 30 minutes at 5° C. and for 3 hours 30 minutes at 22° C. Acetic acid (1 cc) is added, the mixture is then filtered, the precipitate is washed with dimethylformamide (20 cc) and the filtrate is diluted with ethyl acetate (900 cc). The organic phase is washed with distilled water (2×500 cc), a 0.1 N aqueous solution of hydrochloric acid (500 cc), a semi-saturated solution of sodium bicarbonate (500 cc), distilled water (2×500 cc) and a saturated solution of sodium chloride (500 cc). It is dried over anhydrous magnesium sulphate; the mixture is filtered and the filtrate is concentrated to dryness under reduced pressure (30 mm Hg; 4 kPa) at 30° C. The residue is purified by chromatography on a column (height=63 cm, diameter=4.8 cm), containing silica gel (0.06–0.20 mm), elution being carried out under a pressure of 0.4 bar with a mixture of cyclohexane and ethyl acetate (50/50 by Volume) (4 liters) and 250 cc fractions being collected. Fractions 8 to 14, containing the pure product, are combined and concentrated under reduced pressure (30 mm Hg; 4 kPa) at 30° C. to give the syn isomer of 2-benzhydryloxycarbonyl-7-{2-[(2-t-butoxycarbonylprop-2-yl)-oxyimino]-2-(2-tritylaminothiazol-4-yl)-acetamido}-8-oxo-3-[2-(pyridin-3-yl-amino)-thiazol-5-yl]-5-thia-1-azabicyclo[4.2.0] oct-2-ene (4.65 g) in the form of a hard yellow foam.

Infra-red spectrum (CHBr3, characteristic bands in cm$^{-1}$): 3400, 1790, 1725, 1680, 1525, 1495, 1450 1370, 750, 740.

Proton NMR spectrum (250 MHz, DMSO d6, δ in ppm, J in Hz): 1.37 (s, 9H, —C(CH3)3); 1.43 (s, 6H, >C(CH3)2); 3.77 and 3.89 (2d, J=17.5, 2H, —S—CH2—); 5.28 (d, J=5, 1H, —H in the 6-position); 5.83 (dd, J=8 and 5, 1H, —H in the 7-position); 6.72 (s, 1H, —H in the 5-position of the thiazole); 6.89 (s, 1H, —COO—CH(C6H5)2); 7 to 7.4 (mt, aromatic protons, —H in the 4-position of the thiazole and —H in the 5-position of the pyridine); 8.07 ( d broad, J=7.5, 1H, —H in the 4-position of the pyridine ; 8.19 (d broad, J=5, 1H, —H in the 6-position of the pyridine); 8.68 (d, J=2, 1H, —H in the 2-position of the pyridine); 8.83 (s, 1H, —NH—C(C6H5)3); 9.48 (d, J=8, 1H, —CO—NH—); 10.44 (s, 1H, >N—H).

EXAMPLE 12

The syn isomer of 2-benzhydryloxycarbonyl-7-[2-(2-t-butoxycarbonylprop-2-yl)-oxyimino -2-(2-tritylaminothiazol-4-yl)-acetamido]-3-[2-(1-methyl-3-pyridinio-amino)-thiazol-5-yl]-8-oxo-5-thia-1-azabicyclo[4.2.-0]oct-2-ene 5-oxide iodide, obtained as in Example 11, can be treated in the following manner:

N,N-dimethylacetamide (2.4 cc) and then phosphorus trichloride (1.06 cc) are added to a solution, cooled to 0° C., of the syn isomer of 2-benzhydryloxycarbonyl-7-[2-(2-t-butoxycarbonylprop-    2-yl)-oxyimino    -2-(2-tritylaminothiazol-4-yl)-acetamido]-3-[2-(1-methyl-3-pyridinio-amino)-thiazol-5-yl]-8-oxo-5-thia-1-azabicyclo[4.2.0]oct-2-ene 5-oxide iodide (3.76 g) in methylene chloride (30 cc). The reaction mixture is stirred for 45 minutes at 0° C. and then diluted with ethyl acetate (120 cc). A product precipitates and the precipitate is filtered off and washed with ethyl acetate (3×25 cc) and ethyl ether (2×25 cc). The product is dissolved in methylene chloride (100 cc) and then treated with 3S charcoal. The filtrate is concentrated to dryness under reduced pressure (100 mm Hg; 13.3 kPa) and the residue is taken up in ethyl ether (50 cc). The heterogeneous mixture is filtered and the solid is washed with ethyl ether (3×15 cc). It is dried under reduced pressure (0.1 mm Hg; 0.013 kPa) to give the syn isomer of 2-benzhydryloxycarbonyl-7-[2-(2-t-butoxycarbonylprop-2-yl)-oxyimino-2-(2-tritylaminothiazol-4-yl)-acetamido]-3-[2-(1-methyl-3-pyridinio-amino)-thiazol-5-yl]-8-oxo-5-thia-1-aza-bicyclo[4.2.0]oct-2-ene iodide (2.95 g).

Infra-red spectrum (KEr, characteristic bands in cm$^{-1}$): 2980, 2940, 1790, 1728, 1698, 1595, 1575, 1530, 1510, 1450, 1375, 1225, 1142, 1003, 760, 705.

Proton NMR spectrum (250 MHz, DMSO d6, δ in ppm, J in Hz): 1.38 (s, 9H, —COO—C(CH3)3); 1.42 (s, 6H, >C(CH3)2); 3.79 and 3.94 (2d, J=17.5, 2H, —S—CH2—); 4.38

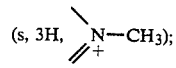

(s, 3H, >N⁺—CH3);

5.27 (d, J=5, 1H, —H in the 6-position); 5.85 (dd, J=8 and 5, 1H, —H in the 7-position); 6.72 (s, 1H, —H in the 5-position of the thiazole); 6.90 (s, 1H, —COO—CH(C6H5)2); 6.95 to 7.4 (mt, aromatic protons +H in the 4-position of the thiazole); 8.05 (dd, J=8 and 5.5, 1H, —H in the 5-position of the pyridinio); 8.39 (d, J=8, 1H, —H in the 4-position of the pyridinio); 8.59 (d, J=5.5, 1H, —H in the 6-position of the pyridinio); 8.83 (s, 1N, —NH—C(C6H5)3); 9.16 (s broad, 1H, —H in the 2-position of the pyridinio); 9.48 (d, J=8, 1H, —CO—NH—); 11.29 (b, 1H, —NH—).

A solution of the syn isomer of 2-benzhydryloxycarbonyl-7-[2-(2-t-butoxycarbonylprop-2-yl)-oxyimino-2-(2-tritylaminothiazol-4-yl)-acetamido]-3-[2-(1-methyl-3-pyridinio-amino)-thiazol-5-yl]-8-oxo-5-thia-1-aza-bicyclo[4.2.0]oct-2-ene iodide (2.85 g) in formic acid (42.8 cc) and anisole (4.3 cc) is heated at 50° C. for 30 minutes. The mixture is then diluted with distilled water (14.3 cc) and stirred at 50° C. for 15 minutes. The reaction solution is concentrated to dryness under reduced pressure (0.1 mm Hg; 0.013 kPa) at 40° C. The residue is taken up in ethanol (100 cc) which is evaporated off under reduced pressure (0.1 mm Hg; 0.013 kPa) to a residual volume of about 40 cc. The operation is repeated and the product is filtered off and washed with ethanol (2×25 cc), ethyl acetate (2×25 cc) and ethyl ether (2×25 cc). The product (0.95 g) is dried under reduced pressure (0.1 mm Hg; 0.013 kPa). A portion of this (0.58 g) is taken and dissolved in anisole (0.75 cc). This gives a brown solution, which is cooled to about 5° C. A cold solution of trifluoroacetic acid (4.90 cc) and distilled water (0.49 cc) is added. The mixture is stirred for 15 minutes at 5° C. and then for 1 hour 15 minutes at 25° C. The reaction mixture is diluted with acetone (3.2 cc), and ethyl ether (13 cc) is then run in. The mixture is stirred for 10 minutes and filtered and the precipitate is washed with ethyl ether (2×10 cc) and dried under reduced pressure (0.1 mm Hg; 0.013 kPa). This gives the syn isomer of 7-{(2-(2-aminothiazol-4-yl)-2-[(2-carboxyprop-2-yl)-oxyimino]-acetamido}-2-carboxy-3-[2-(1-methyl-3-pyridinio-amino)-thiazol-5-yl]-8-oxo-5-thia-1-azabicyclo[4.2.-0]oct-2-ene ditrifluoroacetate (0.60 g) in the form of a light brown powder.

Amberlite IR 45 resin (OH) (12 cc) is added to the syn isomer of 7-{2-(2-aminothiazol-4-yl)-2-[(2-carboxyprop-2-yl)-oxyimino]-acetamido}-2-carboxy-3-[2-(1-methyl-3-pyridinio-amino)-thiazol-5-yl]-8-oxo-5-thia-1-azabicyclo[4.2.0]oct-2-ene ditrifluoroacetate (0.62 g) in distilled water (62 cc). The mixture is stirred for 40 minutes, the resin is filtered off and the filtrate is extracted with ethyl acetate (25 cc). The aqueous phase is concentrated on a rotary evaporator under reduced pressure (30 mm Hg; 4 kPa) to a residual volume of 50 cc. It is then lyophilised to give a pale yellow lyophilisate of the syn isomer of 7-{2-(2-aminothiazol-4-yl)-2-[(2-carboxyprop-2-yl)-oxyimino]-acetamido}-2-carboxylato-3-[2-(1-methyl-3-pyridinio-amino)-thiazol-5-yl]-8-oxo-5-thia-1-azabicyclo[4.2.0]oct-2-ene (0.15 g).

Infra-red spectrum (KBr, characteristic bands in cm$^{-1}$): 3420, 3100, 2985, 1765, 1670, 1600, 1575, 1525, 1470, 1390, 1360, 1335, 1290, 1220, 1150, 1075, 1030, 980, 910, 830, 810, 765, 670, 610, 570, 530, 430, 375.

Proton NMR spectrum (250 MHz, DMSO d$_6$, δ in ppm, J in Hz); 1.47 and 1.50 (2s, 6H, >C(CH$_3$)$_2$); 3.75 and 3.90 (2d, J=17.5, 2H, —S—CH$_2$—); 4.30

(s broad, 3H, \NCH$_3$); 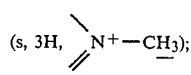

5.23 (d, J=4, 1H, —H in the 6-position); 5.78 (dd, J=4 and 8, 1H, —H in the 7-position); 6.76 (s, 1H, —H in the 5-position of the thiazole); 7.26 (s broad, 2H, —NH$_2$); 7.50 (s, 1H, —H in the 5-position of the thiazole); 7.83 (b, 1H, H in the 5-position of the pyridine); 8.35 (d, 1H, H in the 6-position of the pyridine); 9.02 (d, 1N, H in the 4-position of the pyridine); 9.17 (s broad, 1H, —H in the 2-position of the pyridine).

EXAMPLE 13

The syn isomer of 2-benzhydryloxycarbonyl-7-[2-methoxyimino-2-(2-tritylaminothiazol-4-yl)-acetamido]-8-oxo-3-(2-nicotinoylaminothiazol-5-yl)-5-thia-1-azabicyclo[4.2.0]oct-2-ene 5-oxide (3.03 g) is treated with methyl iodide (0.25 cc) in dimethylformamide (10 cc) in accordance with the procedure described in Example 8 to give the syn isomer of 2-benzhydryloxycarbonyl-7-[2-methoxyimino-2-(2-tritylaminothiazol-4-yl)-acetamido]-3-[2-(1-methyl-3-pyridinio-carbonylamino)-thiazol-5-yl]-8-oxo-5-thia-1-azabicyclo[4.2.0]oct-2-ene 5-oxide iodide (3 g) in the form of a cream solid.

Infra-red spectrum (KBr, characteristic bands in cm$^{-1}$): 1800, 1730, 1670, 1510, 1450, 1035, 755, 700, 670.

Proton NMR spectrum (350 MHz, DMSO d$_6$, in ppm, J in Hz): 3.80 and 4.25 (2d, J=18.5, 2H, —SOCH$_2$—); 3.86 (s, 3H, =NOCH$_3$); 4.47

(s, 3H, \N$^+$—CH$_3$);

5.08 (d, J=3.5, 1H, —H in the 6-position); 5.91 (dd, J=3.5 and 9, 1H, —H in the 7-position); 6.79 (s, 1H, —H in the 5-position of the thiazole); 6.89 (s, 1H, —COOCHAr$_2$); 7.05 to 7.45 (b, 25H, aromatic protons); 7.49 (s, 1H, —H in the 4-position of the thiazole); 8.30 (dd, J=6 and 7, 1H, —H in the 5-position of the pyridinio); 8.73 (s, 1H, —NHC(C$_6$H$_5$)$_3$); 9.06 (d, J=7, 1H, —H in the 4-position of the pyridinio); 9.10 (d, J=9, —CONH—C$_7$); 9.17 (d, J=6, 1H, —H in the 6-position of the pyridinio); 9.57 (s, 1H, —H in the 2-position of the pyridinio).

The syn isomer of 2-benzhydryloxycarbonyl-7-[2-methoxyimino-2-(2-tritylaminothiazol-4-yl)-acetamido]-3-[2-(1methyl-3-pyridinio-carbonylamino)-thiazol-5-yl]-8-oxo-5-thia-1-azabicyclo[4.2.0]oct-2-ene 5-oxide iodide (3 g) is reduced with phosphorus trichloride (0.5 cc) in a mixture of methylene chloride (50 cc) and N,N-dimethylacetamide (5 cc) in accordance with the procedure described in Example 1 to give the crude syn isomer of 2-benzhydryloxycarbonyl-7-[2-methoxyimino-2-(2-tritylaminothiazo[-4-yl)-acetamido]-3-[ 2-1-methyl-3-pyridinio-carbonylamino)-thiazol-5-yl]-8-oxo-5-thia-1-azabicyclo[4.2.0]oct-2-ene iodide (3 g) in the form of a cream-yellow solid.

Proton NMR spectrum (350 MHz, DMSO d$_6$, δ in ppm. J in Hz: 3.90 (b, 5H, =NOCH$_3$ and —SCH$_2$—); 4.48

(s, 3H, \N$^+$—CH$_3$); 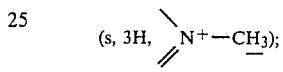

5.27 (d, J=4, 1H, —H in the 6-position); 5.85 (dd, J=4 and 7, 1H, —H in the 7-position); 6.81 (s, 1H, —H in the 5-position of the thiazole); 6.85 (s, 1H, —COO—CHAr$_2$); 7.05 to 7.50 (b, 25H, aromatic protons); 7.52 (s, 1H, —H in the 4-position of the thiazole); 8.3 (dd, J=5 and 8, —H in the 5-position of the pyridinio); 9.09 (d, J=8, 1H, —H in the 4-position of the pyridinio); 9.21 (d, J=5, 1H, —H in the 6-position of the pyridinio); 9.60 (s, 1H, —H in the 2-position of the pyridinio); 9.75 (d, J=7, 1H, —CONH—C$_7$).

The crude syn isomer of 2-benzhydryloxycarbony l-7-[2-methoxyimino-2-(2-tritylaminothiazol-4-yl)-acetamido]-3-[2-(1-methyl-3-pyridinio-carbonylamino)-thiazol-5-yl]-8-oxo-5-thia-1-azabicyclo[4.2.0]oct-2-ene iodide (3 g) is treated with a mixture of formic acid (60 cc) and anisole (7 cc) in accordance with the procedure described in Example 8 to give the crude syn isomer of 7-[2-(2-aminothiazol-4-yl)-2-methoxyiminoacetamido]-2-carboxylato-3-[2-(1-methyl-3-pyridinio-carbonylamino)-thiazol-5-yl]-8-oxo-5-thia-1-azabicyclo[4.2.0]oct-2-ene hydroiodide (2.1 g) in the form of a cream solid, which is taken up in a mixture of distilled water (210 cc) and ethyl acetate (100 cc); after the insoluble material has been filtered off and washed with water (4×25 cc), the aqueous phase is decanted and treated with IR 45 resin (basic) (40 cc) until a pH of 4.6 is reached, and it is then filtered and lyophilised to give the syn isomer of 7-[2-(2-aminothiazol-4-yl)-2-methoxyiminoacetamido]-2-carboxylato-3-[2-(1-methyl-3-pyridinio-oarbonylamino)-thiazol-5-yl]-8-oxo-5-thia-1-azabicyclo[4.2.0]oct-2-ene (0.7 g) in the form of a yellow lyophilisate.

Infra-red spectrum (KBr, characteristic bands in cm$^{-1}$): 3600–2400, 1765, 1670, 1610, 1530, 1390, 1040, 675.

Proton NMR spectrum (250 MHz, DMSO d$_6$, δ in ppm, J in Hz): 3.85 (s, 3H, =NOCH$_3$); 4.42

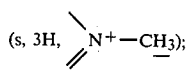
(s, 3H, $>$N$^+$—CH$_3$);

5.17 (d, J=4, 1H, —H in the 6-position); 5.74 (dd, J=4 and 7.5, 1H, —H in the 7-position); 6.75 (s, 1H, —H in the 5-position of the thiazole); 7.24 (s broad, 2H, —NH$_2$); 7.51 (s, 1H, —H in the 4-position of the thiazole); 8.12 (b, 1H); 9.01 (b, 2H ; and 9.50 (s, H): protons of the pyridinio; 9.64 (d, J=7.5, 1H, —CONH—C$_7$).

The syn isomer of 2-benzhydryloxycarbonyl-7-[2-methoxyimino-2-(2-tritylaminothiazol-4-yl)-acetamido]-8-oxo-3-(2-nicotinoylaminothiazol-5-yl)-5-thia-1-azabicyclo-[4.2.0]oct-2-ene 5-oxide can be prepared in the following manner:

N,N'-Dicyclohexylcarbodiimide (1.24 g) is added to a solution, cooled to +5° C., of 7-amino-2-benzhydryloxycarbonyl-8-oxo-3-(2-nicotinoylaminothiazol-5-yl)-5-thia- 1-azabicyclo[4.2.0]oct-2-ene 5-oxide (2.8g), the syn isomer of 2-methoxyimino-2-(2-tritylaminothiazol-4-yl)-acetic acid (2.66 g) and 1-hydroxybenzotriazole (0.82 g) in N,N-dimethylformamide (20 cc), and the reaction mixture is then stirred for 1 hour at +5° C. and then for 64 hours at 20° C; after filtration, the reaction mixture is diluted with chloroform (200 cc) and washed with a 5% strength solution of sodium bicarbonate (100 cc), water (100 cc) and then a saturated solution of sodium chloride (100 cc). After drying over magnesium sulphate, the organic phase is concentrated to dryness under reduced pressure (30 mm Hg; 4 kPa) at 30° C. to give the crude product (5 g). This crude product (10 g) is chromatographed on a column containing silica gel (0.2–0.06 mm) (250 cc), elution being carried out successively with a mixture of methylene chloride and ethyl acetate (75/25 by volume) (1 liter), then a mixture of methylene chloride and ethyl acetate (50/50 by volume) (1 liter) and then ethyl acetate (2 liters) and a mixture of ethyl acetate and methanol (80/20 by volume) (1 liter) and 100 cc fractions being collected. Fractions 19 to 33 are combined and concentrated to dryness under reduced pressure (30 mm Hg; 4 kPa) at 30° C. to give the syn isomer of 2-benzhydryLoxycarbonyl-7-[2-methoxyimino-2-(2-tritylaminothiazol-4-yl)-acetamido]-8-oxo-3-(2-nicotinoylaminothiazol-5-yl)-5-thia-1-azabicyclo[4.2.0]oct-2-ene 5-oxide (6.2 g) in the form of an orange solid.

Infra-red spectrum (KBr, characteristic bands in cm$^{-1}$): 3250, 1800, 1730, 1675, 1590, 1540, 1515, 1450, 1040, 755, 740, 700.

Proton NMR spectrum (350 MHz, DMSO d$_6$, δ in ppm, J in Hz): 3.79 and 4.23 (2d, J=19, 2H, —SOCH$_2$—); 3.86 (s, 3H, =NOCH$_3$); 5.07 (d, J=4, 1H, H in the 6-position); 5.89 (dd, J=4 and 9, 1H, H in the 7-position); 6.79 (s, 1H, H in the 5-position of the thiazole); 6.88 (s, 1H, —CO$_2$CHAr$_2$); 7.0 to 7.50 (b, 25H, aromatic protons); 7.42 (s, 1H, H in the 4-position of the thiazole); 7.57 (dd, J=5 and 8, 1H, H in the 5-position of the pyridine); 8.40 (m, 1H, H in the 4-position of the pyridine); 8.72 (s, 1H, —NH—C(C$_6$H$_5$)$_3$); 8.79 (dd, J=1 and 5, H in the 6-position of the pyridine); 9.04 (d, J=9, CONH—C$_7$); 9.19 (d, J=1, 1H, H in the 2-position of the pyridine); 12.87 (s broad, 1H, —NHCO—).

The 7-amino-2-benzhydryloxycarbonyl-8-oxo-3-(2-nicotinoylaminothiazol-5-yl)-5-thia-1-azabicyclo[4.2.0]oct-2-ene 5-oxide can be prepared in the following manner:

A solution of 2-benzhydryloxycarbonyl-7-t-butoxycarbonylamino-8-oxo-3-(2-nicotinoylaminothiazol-5-yl)-5-thia-1-azabicyclo[4.2.0]oct-2-ene 5-oxide (9 g) in acetonitrile (90 cc) is treated with methanesulphonic acid (9 cc) for 8 minutes at 25oC and then poured into a 5% strength solution of sodium bicarbonate (300 cc). The precipitate is filtered off, washed with distilled water (5×20 cc) and then with ethyl ether (3×20 cc) and dried. This gives 7-amino-2-benzhydryloxycarbonyl-8-oxo-3-(2-nicotinoylaminothiazol-5-yl)-5-thia-1-azabicyclo[4.2.0]oct-2-ene 5-oxide (6.55 g) in the form of a cream solid.

Infra-red spectrum (KBr, characteristic bands in cm$^{-1}$): 3410, 1780, 1730, 1670, 1590, 1550, 1020, 895, 705.

Proton NMR spectrum (250 MHz, DMSO d$_6$, δ in ppm, J in Hz): 3.76 and 4.30 (2d, J=17.5, 2H, —SOCH$_2$—); 4.87 and 4.96 (2d, J=4, 2×1H, —H in the 6-position and 7-position); 6.89 (s, 1H, —CO$_2$CHAr$_2$); 7.0 to 7.4 (b, 10H, aromatic protons); 7.46 (s, 1H, —H in the 4-position of the thiazole); 7.6 (dd, J=9 and 5, 1H, —H in the 5-position of the pyridine); 8.42 (d, J=9, 1H, —H in the 4-position of the pyridine); 8.80 (dd, J=5 and 1, 1H, —H in the 6-position of the pyridine); 9.21 (d, J=1, 1H, —H in the 2-position of the pyridine).

The 2-benzhydryloxycarbonyl-7-t-butoxycarbonylamino-8-oxo-3-(2-nicotinoylaminothiazol-5-yl)-5-thia-1-azabicyclo[4.2.0]oct-2-ene 5-oxide can be prepared in the following manner:

2-Benzhydryloxycarbonyl-7-t-butoxy-carbonylamino-8-oxo-3-(2-nicotinoylaminothiazol-5-yl)-5-thia-1-azabicyclo[4.2.0]oct-2-ene 5-oxide (18.5 g) is obtained by oxidation of the corresponding sulphide (18.4 g) by reaction, at −10° C., with 85% pure metachloroperbenzoic acid (5.6 g) in a mixture of methanol (250 cc) and chloroform (870 cc) for 10 minutes, followed by washing of the reaction mixture with a mixture of distilled water (250 cc) and a saturated solution of sodium bicarbonate (500 cc) and then with distilled water (500 cc), and finally concentration of the organic phase to dryness under reduced pressure (30 mm Hg: 4 kPa) at 30° C. and solidification of the resulting residue with ethyl ether.

Proton NMR spectrum (250 MHz, DMSO d$_6$, δ in ppm, J in Hz): 1.44 (s, 9H, (CH$_3$)$_3$C—); 3.82 and 4.47 (2d, J=18, 2H, —SOCH$_2$—); 5.07 (d, J=5, 1H, —H in the 6-position); 5.86 (dd, J=5 and 10, 1H, H in the 7-position); 6.47 (d, J=10, 1H, —CONHC$_7$); 6.90 (s, 1H, -CO$_2$CHAr$_2$); 7.05 to 7.4 (b, 10H, aromatic protons); 7.51 (s, 1H, —H of the thiazole); 7.62 (dd, J=5 and 8, 1H, —H in the 5-position of the pyridine); 8.42 (ddd, J=8, 2 and 1.5, 1H, H in the 4-position of the pyridine); 8.81 (dd, J=5 and 1.5, 1H, —H in the 6-position of the pyridine); 9.2 (d, J=2, 1H, —H in the 2-position of the pyridine); 12.92 (s broad, 1H, —NHCO—).

The 2-benzhydryloxycarbonyl-7-t-butoxycarbonylamino-3-(2-nicotinoylaminothiazol-5-yl)-8-oxo-5-thia-1-azabicyclo[4.2.0]oct-2-ene can be prepared in the following manner:

Nicotinoyl chloride hydrochloride (7.12 g) is added to a solution of 3-(2-aminothiazol-5-yl)-2-benzhydryloxycarbonyl-7-t-butoxycarbonylamino-8-oxo-5-thia-1-azabicyclo[4.2.0]oct-2-ene (11.3 g) in tetrahydrofuran (300 cc), cooled to 3° C., and triethylamine (11.12 cc) is then added in the course of 10 minutes. The mixture is stirred for 1 hour at 3° C. and then for 2 hours while allowing the temperature to rise to 20° C. The reaction mixture is poured into ethyl acetate (400 cc) and washed with distilled water (3×120 cc) and a saturated solution of sodium chloride (100 cc). The organic phase is dried and concentrated to dryness under reduced pressure (30 mm Hg; 4 kPa) at 40° C. The residue is crystallised from ethyl acetate (20 cc) to give 2-benzhydryloxycarbonyl-7-t-butoxycarbonylamino-3-(2-nicotinoylaminothiazol-5-yl)-8-oxo-5-thia-1-azabicyclo[4.2.0]oct-2-ene (7.4 g) in the form of a yellow solid.

Rf=0.24 (silica gel chromatography plate, eluent: 20/80 by volume mixture of cyclohexane and ethyl acetate).

EXAMPLE 14

A solution of 2-(2-t-butoxycarbonylprop-2-yl-oxyimino)-2-(2-tritylaminothiazol-4-yl)-acetyl chloride in methylene chloride (this solution being prepared in accordance with the procedure described in Belgian Pat. No. 876,538 from the corresponding acid (3.44 g)) is added in the course of 10 minutes to a suspension, cooled to −10° C., of the syn isomer of 7-amino-2-carboxylato-3-[2-(1-methyl-3-pyridinio)-thiazol-5-yl]-8-oxo-5-thia-1-azabicyclo[4.2.0]oct-2-ene hydrochloride (2.46 g) in a mixture of acetonitrile (30 cc) and N,N-dimethylacetamide (30 cc) containing triethylamine (3.9 cc). The reaction mixture is stirred for 1 hour at between 0° and −10° C. and then for 1 hour at 20° C. Methanol (1 cc) is added and the methylene chloride is then evaporated off under reduced pressure (30 mm Hg; 4 kPa) at 30° C. The residual solution is diluted with water (300 cc). The precipitate is filtered off, washed with distilled water (50 cc) and then with ether (2×50 cc) and redissolved in ethyl acetate (80 cc). The solution is filtered and the filtrate is diluted with ethyl ether (400 cc). The precipitate is filtered off, washed with ethyl ether (2×50 cc) and dried to give the syn isomer of 7-[2-(2-t-butoxycarbonylprop-2-yl-oxyimino)-2-(2-tritylaminothiazol-4-yl)-acetamido]-2-carboxylato-3-[2-(1-methyl-3-pyridinio)-thiazol-5-yl]-8-oxo-5-thia-1-azabicyclo-[4.2.0]-oct-2-ene hydrochloride (3.1 g) in the form of a yellow solid.

Infra-red spectrum (KBr), characteristic bands in (cm$^{-1}$): 1775, 1730, 1680, 1615, 1580, 1150.

Proton NMR spectrum (350 MHz, DMSO-d$_6$, δ in ppm, J in Hz): 1.42 (b, 16H, —C(CH$_3$)$_2$CO$_2$C(CH$_3$)$_3$); 3.80 (AB type, 2H, —SCH$_2$—); 4.43

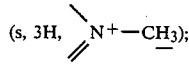

5.16 (d, J=5, 1H, —H in the 6-position); 5.63 (dd, J=5 and 8, 1H, —H in the 7-position); 6.78 (s, 1H, —H in the 4-position of the thiazole ; 7.10 to 7.50 (b, 15H, aromatic protons); 8.13 (b, 2H, —H in the 5-position of the thiazole and —H in the 5-position of the pyridinio); 8.79 (s, 1H, —NH—thiazole); 8.88 (d, J=7, 1H, —H in the 4-position of the pyridinio); 8.97 (b, 1H, —H in the 6-position of the pyridinio); 9.35 (d, J=8, 1H, —CONH—); 9.51 (s, 1H, —H in the 2-position of the pyridinio).

The syn isomer of 7-[2-(2-t-butoxycarbonylprop-2-yl-oxyimino)-2-(2-tritylaminothiazol-4-yl)-acetamido]-2-carboxylato-3-[2-(1-methy 3-pyridinio)-thiazol-5-yl]-8-oxo-5-thia-1-azabicyclo[4.2.0]-oct-2-ene hydrochloride (3 g) is stirred for 1 hour at 25° C. with formic acid (20 cc) containing concentrated hydrochloric acid (1.2 cc). The insoluble material is removed by filtration and washed with formic acid (2×0.5 cc). The combined filtrates are concentrated to dryness under reduced pressure (0.3 mm Hg; 0.04 kpa) at 30° C. The residue is taken up in ethanol (40 cc), which is evaporated off to dryness under reduced pressure (30 mm Hg; 4 kpa) at 30° C. This operation is repeated once more and the residue is then taken up in ethanol (50 cc). The solid is filtered off, washed with ethanol (4×20 cc), acetone (2×20 cc) and ethyl ether (2×40 cc) and dried to give the syn isomer of 7-[2-(2-amino-thiazol-4-yl)-2-(2-carboxyprop-2-yl-oxyimino)-acetamido]-2-carboxylato-3 2-(1-methyl-3-pyridinio)-thiazol-5-yl]-8-oxo-5-thia-1-azabicyclo[4.2.0]-oct-2-ene hydrochloride (1.4 g) in the form of a yellow solid, the characteristics of which are similar to those of the product described in Example 2.

The 7-amino-2-carboxylato-3-[2-(1-methyl-3-pyridinio)-thiazol-5-yl]-8-oxo-5-thia-1-azabicyclo[4.2.0]-oct-2-ene hydrochloride can be obtained in the following manner:

2-Benzhydryloxycarbonyl-7-t-butoxycarbonylamino-3-[2-(1-methyl-3-pyridinio)-thiazol-5-yl]-8-oxo-5-thia-1-azabicyclo[4.2.0]-oct-2-ene iodide (54 g) is treated with trifluoroacetic acid (500 cc) at 25° C. for 40 minutes. The reaction mixture is concentrated to dryness under reduced pressure (2 mm Hg; 0.27 kpa) at 35° C. The residue is taken up in ethanol (100 cc), which is evaporated off under reduced pressure (30 mm Hg; 4 kpa) at 35° C. This operation is repeated a further 2 times and the product is then solidified with ethanol (100 cc), filtered off, washed with ethyl ether (4×50 cc) and then taken up in normal hydrochloric acid (100 cc) at 35° C. The solution is filtered and the filtrate is diluted with isopropanol (100 cc) and kept at 4° C. for 16 hours. The crystals formed are filtered off and washed with isopropanol (20 cc) and then with ethyl ether (3×50 cc) to give 7-amino-2-carboxylato-3-2-(1-methyl-3-pyridinio)-thiazol-5-yl-8-oxo-5-thia-1-azabicyclo[4.2.0]-oct-2-ene hydrochloride (12 g) in the form of yellow crystals.

Proton NMR spectrum (250 MHz, DMSO-d$_6$, δ in ppm, J in Hz) 3.88 and 4.0 (2d, J=18, 2H, —SCH$_2$—); 4.43

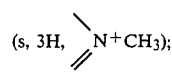

4.9 4.97 (d, J=5, 1H, —H in the 7-position); 5.17 (d, J=5, 1H, —H in the 6-position); 8.17 (s, 1H, H of the thiazole); 8.21 (dd, J=8 and 6, 1H, —H in the 5-position of the pyridinio); 8.99 (d, J=8, 1H, —H in the 4-position of pyridinio); 9.04 (d, J=5, —H in the 6-position of the pyridinio); 9.6 (s, 1H, —H in the 2-position of pyridinio).

The 2-benzhydryloxycarbonyl-7-t-butoxycarbonylamino-3-[2-(1-methyl-3-pyridinio)-thiazol-5-yl]-8-oxo-5-thia-1-azabicyclo[4.2.0]-oct-2-ene iodide can be obtained in the following manner:

A solution of 2-benzhydryloxycarbonyl-7-t-butoxycarbonylamino-8-oxo-3-[2-(pyridin-3-yl)-thiazol-5-yl]-5-thia-1-azabicyclo[4.2.0]-oct-2-ene (50 g) in N,N-dimethylformamide (200 cc) is treated with methyl iodide (6.5 cc) in accordance with the procedure described in Example 2 to give 2-benzhydryloxycarbonyl-7-t-butoxycarbonylamino-3-[2-(1-methyl-3-pyridinio)-thiazol-5- yl]-8-oxo-5-thia-1-azabicyclo[4.2.0]-oct-2-ene iodide (54.7 g) in the form of an orange-yellow solid.

Proton NMR spectrum (250 MHz, DMSO-$d_6$, δ in ppm, J in Hz) 1.46 (s, 9H, (CH$_3$)$_3$C—); 3.43 and 4.08 (2d, J=17.5, 2H, —SCH$_2$—); 4.50

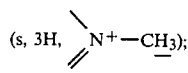 (s, 3H, $\diagdown$N$^+$—CH$_3$);

5.27 (d, J=5, 1H, —H in the 6-position); 5.72 (dd, J=5 and 9, 1H, —H in the 7-position); 6.93 (s, 1H, —CO$_2$CHAr$_2$); 6.95 to 7.5 (b, 10H, aromatic protons); 8.1 (s, 1H, —H of the thiazole); 8.16 (d, J=9, 1H, —CONH—); 8.26 (2d, J=6 and 8, 1H, H in the 5-position of the pyridinio); 8.74 (d, J=8, 1H, H in the 4-position of the pyridinio); 9.08 (d, J=6, 1H, H in the 6-position of the pyridinio); 9.42 (s, 1H, —H in the 2-position of the pyridinio).

The present invention also provides pharmaceutical compositions which comprise, as active ingredient, a cephalosporin derivative of general formula I, or a pharmaceutically acceptable addition salt thereof with an acid, metal salt or addition salt with a nitrogen-containing base, in association with a pharmaceutically acceptable carrier or coating. These medicaments can be administered orally, parenterally (in particular intramuscularly or intravenously) or rectally.

Tablets, pills, powders (generally presented in capsules, e.g. gelatine capsules) or granules can be used as solid compositions for oral administration. In these compositions, the active product according to the invention is mixed with one or more inert diluents or adjuvants such as sucrose, lactose or starch. These compositions can also comprise substances other than diluents, e.g. a lubricant such as magnesium stearate.

Solutions, suspensions, syrups and elixirs containing inert diluents such as water or paraffin oil, and pharmaceutically acceptable emulsions, can be used as liquid compositions for oral administration. These compositions can also comprise substances other than diluents, e.g. wetting, sweetening or flavouring products.

The compositions for parenteral administration can be suspensions, emulsions or aqueous or non-aqueous sterile solutions. Propylene glycol, a polyethylene glycol, vegetable oils, in particular olive oil, and injectable organic esters, e.g. ethyl oleate, can be employed as the solvent or vehicle. These compositions can also contain adjuvants, in particular wetting, emulsifying or dispersing agents. Sterilisation can be carried out in several ways, e.g. using a bacteriological filter, by incorporating sterilising agents into the composition, by irradiation or by heating. The compositions can also be prepared in the form of sterile solid compositions which are to be dissolved in sterile water or any other injectable sterile medium at the time of use.

The compositions for rectal administration are suppositories which can contain, in addition to the active product, excipients such as cacao butter or semi-synthetic glycerides.

In human therapy, the medicaments according to the present invention are particularly useful in the treatment of infections of bacterial origin.

In general, the doctor will determine the dosage which he considers to be most appropriate as a function of the age, the weight, the degree of infection and the other factors peculiar to the subject to be treated. In general, the adult daily doses are between 1 and 10 g of active product, administered intramuscularly.

The examples which follow, which are given without implying a limitation, illustrate a composition according to the present invention.

EXAMPLE A

An isotonic aqueous solution (100 cc) is prepared which contains sodium bicarbonate (1.40 g) and, as the active product, the syn isomer of 7-[2-(2-aminothiazol-4-yl)-2-methoxyiminoacetamido]-2-carboxylato-3-[2-(1-carboxymethyl-3-pyridinio)-thiazol-5-yl]-8-oxo-5-thia-1-azabicyclo[4.2.0]-oct-2-ene (10 g). After filtration on a bacteriological filter, this solution is divided up under aseptic conditions into ampoules (at a rate of 10 cc per ampoule) and lyophilised and the ampoules are sealed.

Each ampoule contains the equivalent of 1 g of the active product in the form of its sodium salt.

EXAMPLE B

An isotonic aqueous solution (100 cc) is prepared which contains sodium bicarbonate (1.33 g) and, as the active product, the syn isomer of 7-[2-(2-aminothiazol-4-yl)-2-(2-carboxyprop-2-yl-oxyimino)-acetamido]-2-carboxylato-3-[2-(1-methyl-3-pyridinio-amino)-thiazol-5-yl]-8-oxo-5-thia-1-azabicyclo[4.2.0]-oct-2-ene (10 g). After filtration of a bacteriological filter, this solution is divided under aseptic conditions into ampoules (at a rate of 10 cc per ampoule) and lyophilised and the ampoules are sealed.

Each ampoule contains the equivalent of 1 g of the active product in the form of its sodium salt.

We claim:

1. A cephalosporin derivative of the formula:

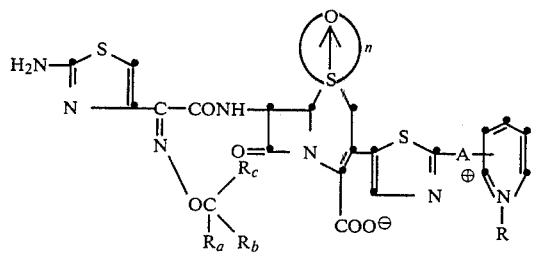

in which the symbol A represents a single bond or a divalent radical chosen from —CH$_2$—, —NH— or —NHCO—, attached to the 3-position or 4-position of the pyridinio radical, the symbol R represents a methyl, carboxymethyl, carbamoylmethyl, benzyl or allyl radical, and either the symbols R$_a$, R$_b$ and R$_c$ each represent a hydrogen atom, or the symbol R$_a$ represents a carboxyl radical and the symbols R$_b$ and R$_c$, which are identical or different, represent hydrogen atoms or alkyl radicals having 1 to 4 carbon atoms, or together form an alkylene radical containing 2 to 5 carbon atoms, and n is equal to 0 or 1, the group —OCR$_a$R$_b$R$_c$ being in the syn position, and if appropriate the isomeric forms of the said cephalosporin derivative and mixtures thereof, or an addition salt thereof with an acid, or, if appropriate, a metal salt thereof or an addition salt thereof with a nitrogen-containing base.

2. A cephalosporin according to claim 1, in which the symbol A represents a single bond or a divalent radical chosen from amongst —CH$_2$—, —NH— or —NHCO—, attached to the 3-position or 4-position of the pyridinio radical, the symbol R represents a methyl, carboxymethyl, carbamoylmethyl or benzyl radical, and either the symbols $R_a$, $R_b$ and $R_c$ each represent a hydrogen atom, or the symbol $R_a$ represents a carboxyl radical and the symbols $R_b$ and $R_c$ represent hydrogen atoms or methyl radicals, and n is equal to 0 or 1, or an addition salt thereof with an acid, or, if appropriate, a metal salt thereof, or an addition salt thereof with a nitrogen-containing base.

3. A cephalosporin according to claim 1, in which the symbol A is a single bond or a radical —NH—, attached to the 3-position of the pyridinio radical, the symbol R represents a methyl, carboxymethyl or carbamoylmethyl radical, and either the symbols $R_a$, $R_b$ and $R_c$ represent hydrogen atoms, or the symbol $R_a$ represents a carboxyl radical and the symbols $R_b$ and $R_c$ represent hydrogen atoms or methyl radicals, and n equals 0, or an addition salt thereof with an acid, or, if appropriate, a metal salt thereof or an addition salt thereof with a nitrogen-containing base.

4. A compound according to claim 1 which is the syn isomer of 7-[2-(2-aminothiazol-4-yl)-2-methoxyiminoacetamido]-2-carboxylato-3-[2-(1-methyl-3-pyridinio)-thiazol-5-yl]-8-oxo-5-thia-1-azabicyclo[4.2.0]oct-2-ene or a pharmaceutically acceptable addition salt thereof with an acid.

5. A compound according to claim 1 which is the syn isomer of 7-[2-(2-aminothiazol-4-yl)-2-carboxymethoxyiminoacetamido]-2-carboxylato-3-[2-(1-methyl-3-pyridinio)-thiazol-5-yl]-5-thia-1-azabicyclo[4.2.0]oct-2-ene or a pharmaceutically acceptable addition salt thereof with an acid, metal salt or addition salt thereof with a nitrogen-containing base.

6. A compound according to claim 1 which is the syn isomer of 7-[2-(2-aminothiazol-4-yl)-2-(2-carboxyprop-2-yl)-oxyiminoacetamido]-2-carboxylato-3-[2-(1-methyl-3-pyridinio)-thiazol-5'-yl]-8-oxo-5-thia-1-azabicyclo-[4.2.0]oct-2-ene or a pharmaceutically acceptable addition salt thereof with an acid, metal salt or addition salt thereof with a nitrogen-containing base.

7. A compound according to claim 1 which is the syn isomer of 7-[2-(2-aminothiazol-4-yl)-2-methoxyiminoacetamido]-2-carboxylato-3-[2-(1-carboxymethyl-3-pyridinio)-thiazol-5-yl]8-oxo-5-thia-1-azabicyclo[4.2.0]oct-2-ene or a pharmaceutically acceptable addition salt thereof with an acid, metal salt or addition salt thereof with a nitrogei-containing base.

8. A compound according to claim 1 which is the syn isomer of 7-[2-(2-aminothiazol-4-yl)-2-methoxyiminoacetamido]-2-carboxylato-3[2-(1-carbamoyl-3-pyridinio)-thiazol-5-yl]-8-oxo-5-thia-1-azabicyclo[4.2.0]oct-2-ene or a pharmaceutically acceptable addition salt thereof with an acid.

9. A compound according to claim 1 which is the syn isomer of 7-[2-(2-aminothiazol-4-yl)-2-(2-carboxyprop-2-yl-oxyimino)-acetamido]-3-[2-(1-benzyl-3-pyridinio)-thiazol-5-yl]2-carboxylato-8-oxo-5-thia-1-azabicyclo [4.2.0]oct-2-ene or a pharmaceutically acceptable addition salt thereof with an acid.

10. A compound according to claim 1 which is the syn-isomer of 7-[2-(2-aminothiazol-4-yl)-2-(2-carboxyprop-2-yl)-oxyiminoacetamido]2-carboxylato-3[2-(1-methyl-4-pyridinio)-thiazol-5-yl]-8-oxo-5-thia-1-azabicyclo[4.2.0]-oct-2-ene, or a pharmaceutically acceptable addition salt thereof with an acid metal salt or addition salt thereof with a nitrogen-containing base.

11. A compound according to claim 1 which is the syn-isomer of 7-[2-(2-aminothiazol-4-yl)-2-methoxyimino-acetamido]-2-carboxylato-3-[2-(1-methyl-4-pyridinio)-thiazol-5-yl]-8-oxo-5-thia-1-azabicyclo[4.2.0]oct-2-ene or a pharmaceutically acceptable addition salt with an acid.

12. A compound according to claim 1 which is the syn-isomer of 7-[2-(2-aminothiazol-4-yl)-2-methoxyimino-acetamido. 2-carboxylato-3-2-(1-methyl-3-pyridinio-methyl)-thiazol-5-yl]-8-oxo-5-thia-1-azabicyclo[4.2.0]oct-2-ene or a pharmaceutically acceptable addition salt with an acid.

13. A compound according to claim 1 which is the syn isomer of 7-[2-(2-aminothiazol-4-yl)-2-methoxyimino-acetamido]-2-carboxylato-3[2-(1-methyl-3-pyridinio-amino)-thiazol-5-yl]-8-oxo-5-thia-1-azabicyclo[4.2.0]oct-2-ene or a pharmaceutically acceptable addition salt thereof with an acid.

14. A compound according to claim 1 which is the syn isomer of 7-{2-(2-aminothiazol-4-yl)-2-[(2-carboxyprop-2-yl)-oxyimino]-acetamido}-b 2-carboxylato-3-[2-(1-methyl-3-pyridinio-amino)-thiazol-5-yl]-8-oxo-5-thia-1-azabicyclo-[4.2.0]oct-2-ene 5-oxide or a pharmaceutically acceptable addition salt thereof with an acid, metal salt, or addition salt thereof with a nitrogen-containing base.

15. A compound according to claim 1 which is the syn isomer of 7-{2-(2-aminothiazol-4-yl)-2[(2-carboxyprop-2-yl)-oxyimino]-acetamido}-2-carboxylato-3-[2-(1-methyl-3-pyridinio-amino)-thiazol-5-yl]-8-oxo-5-thia-1-azabicyclo-[4.2.0]oct-2-ene or a pharmaceutically acceptable addition salt thereof with an acid, metal salt, or addition salt thereof with a nitrogen-containing base.

16. A compound according to claim 1 which is the syn isomer of 7[2-(2-aminothiazol-4-yl)-2-methoxyimino-acetamido]-2-carboxylato-3-[2-(1-methyl-3-pyridinio-carbonylamino)-thiazol-5-yl]-8-oxo-5-thia-1-azabicyclo-[4.2.0]oct-2-ene, or a pharmaceutically acceptable addition salt thereof with an acid.

17. A pharmaceutical composition which comprises, as active ingredient, a cephalosporin as claimed in claim 1 or an addition salt thereof with an acid, or a metal salt thereof, or an addition salt thereof with a nitrogen-containing base, in association with a pharmaceutically acceptable carrier or coating.

* * * * *